United States Patent [19]

Watson et al.

[11] Patent Number: 5,120,848
[45] Date of Patent: Jun. 9, 1992

[54] IMIDAZOLE DERIVATIVES

[75] Inventors: Nigel S. Watson, Chalfont St Giles; Chuen Chan, Ickenham; Barry C. Ross, Luton, all of England

[73] Assignee: Glaxo Group Limited, London, England

[21] Appl. No.: 639,184

[22] Filed: Jan. 9, 1991

Related U.S. Application Data

[62] Division of Ser. No. 415,917, Oct. 2, 1989, Pat. No. 5,013,749.

[30] Foreign Application Priority Data

Oct. 3, 1988 [GB] United Kingdom ............ 8823191
Oct. 3, 1988 [GB] United Kingdom ............ 8823192
Feb. 9, 1989 [GB] United Kingdom ............ 8902847

[51] Int. Cl.⁵ .................. C07D 413/14; C07D 233/60
[52] U.S. Cl. .................. 546/278; 546/277; 548/225; 548/341; 548/342
[58] Field of Search .............. 548/225, 341, 342; 546/277, 278

[56] References Cited

U.S. PATENT DOCUMENTS 4,231,938  11/1980  Monaghan et al. ............ 514/341
4,647,576  3/1987   Hoefle et al. ................. 514/341

Primary Examiner—Johann Richter
Attorney, Agent, or Firm—Bacon & Thomas

[57] ABSTRACT

This invention relates to imidazole derivatives having hypocholesterolemic and hypolipidemic activity, to processes for their preparation, to pharmaceutical compositions containing them and to their use in medicine, particularly in the treatment and/or prevention of atherosclerosis and coronary heart disease.

2 Claims, No Drawings

IMIDAZOLE DERIVATIVES

This application is a division of application Ser. No. 07/415,917, filed Oct. 2, 1989, now U.S. Pat. No. 5,013,749.

This invention relates to imidazole derivatives having hypocholesterolemic and hypolipidemic activity, to processes for their preparation, to pharmaceutical compositions containing them and to their use in medicine, particularly in the treatment and/or prevention of atherosclerosis and coronary heart disease.

High levels of blood cholesterol and blood lipids are conditions which are involved in the onset of vessel wall disease. 3-Hydroxy-3-methylglutaryl-coenzyme A (HMG-CoA) reductase is the rate-limiting enzyme in cholesterol biosynthesis and it is well known that inhibitors of this enzyme are effective in lowering the level of blood plasma cholesterol, especially low density lipoprotein cholesterol (LDL-C). It has now been established that lowering LDL-C levels affords protection from coronary heart disease.

Derivatives of mevalonic acid and the corresponding lactones are known to inhibit HMG-CoA reductase, for example Monaghan et al reported (U.S. Pat. No. 4,231,938) the formation of the mevalonolactone analogue mevinolin (now known as lovastatin) by the cultivation of a microfungus of the genus Aspergillus and that this product was a potent inhibitor of cholesterol biosynthesis.

More recently, PCT Patent Specification No. WO 8607054 discloses C-linked imidazole derivatives useful for treating hyperlipoproteinaemia and atherosclerosis, which have the following formula:

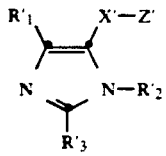

where X' represents a $C_{1-3}$ saturated or unsaturated alkylene chain; Z' represents inter alia a group of formula (a) —CH(OH)—CH$_2$—C(R$_{13}$')(OH)—CH$_2$—CO$_2$R$_{14}$' or (b)

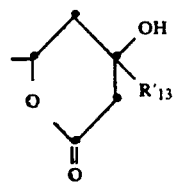

where R$_{13}$' is hydrogen or $C_{1-3}$alkyl and R$_{14}$' is hydrogen, an ester group or a cation; and R$_1$', R$_2$' and R$_3$' represent inter alia $C_{1-6}$alkyl or optionally substituted phenyl.

U.S. Pat. No. 4,647,576 discloses N-substituted pyrroles, useful as hypolipidaemic and hypocholesterolaemic agents, which have the formula

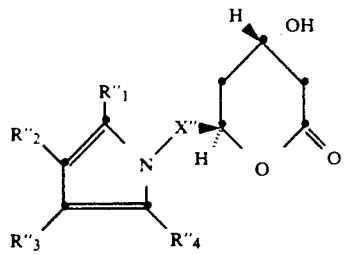

and the corresponding dihydroxy acids thereof where X" represents —CH$_2$—, —CH$_2$CH$_2$— or —CH(CH$_3$)—CH$_2$; R$_1$" represents inter alia $C_{1-4}$alkyl, optionally substituted phenyl or a pyridyl ring or N-oxide thereof; R$_2$" and R$_3$" represent inter alia hydrogen atoms, CF$_3$, $C_{1-4}$alkyl or a phenyl ring; and R$_4$" represents inter alia $C_{1-4}$alkyl or CF$_3$.

Similarly, EP0221025 discloses inter alia C-substitued pyrroles for use as hypolipoproteinemic and antiatherosclerotic agents which have the formulae

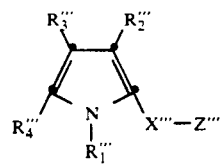

or

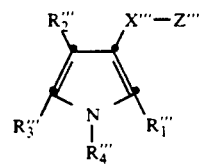

where R$_1$''', R$_2$''', R$_3$''' and R$_4$''' are independently $C_{1-4}$alkyl not containing an asymmetric carbon atom, $C_{3-7}$cycloalkyl or a ring

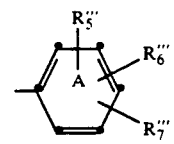

or in the case of R$_3$''' and R$_4$''' additionally hydrogen; each R$_5$''', R$_6$''' and R$_7$''' are independently inter alia hydrogen or halogen atoms, alkyl, alkoxy or trifluoromethyl groups; X''' is (CH$_2$)$_m$ or (CH$_2$)$_q$CH=CH(CH$_2$)$_q$, m is 0,1,2 or 3 and both q's are 0 or one is 0 and the other is 1;

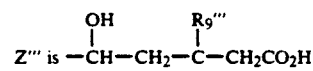

wherein R$_9$''' is hydrogen or $C_{1-3}$alkyl, in free acid form or in the form of an ester, lactone or salt as appropriate.

We have now found certain novel substituted N-vinyl imidazole derivatives which are potent inhibitors of cholesterol biosynthesis by virtue of their ability to inhibit the enzyme HMG-CoA reductase.

Thus, the invention provides compounds of the general formula (I):

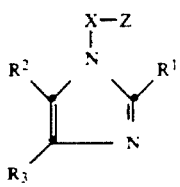

in which
one of the groups $R^1$ or $R^2$ represents a $C_{1-6}$alkyl group optionally substituted by one to three halogen atoms and the other represents a phenyl or pyridyl ring or N-oxide thereof optionally substituted by one or more substituents selected from halogen atoms and hydroxyl, $C_{1-3}$alkyl, $C_{1-3}$alkoxy and trifluoromethyl groups;

$R^3$ represents a phenyl or pyridyl ring or N-oxide thereof optionally substituted by one or more substituents selected from halogen atoms and hydroxyl, $C_{1-3}$alkyl, $C_{1-3}$alkoxy and trifluoromethyl groups with the proviso that only one of the groups $R^1$, $R^2$ or $R^3$ represents an optionally substituted pyridyl ring;

X represents —CH=CH—; and
Z represents

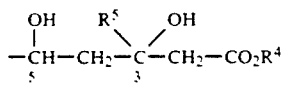

or

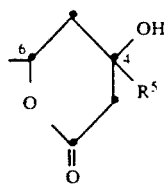

where $R^4$ represents a hydrogen atom, a carboxyl protecting group or a physiologically acceptable cation; and $R^5$ represents a hydrogen atom or a $C_{1-3}$alkyl group; and solvates thereof.

It will be appreciated that salts formed with cations other than the physiologically acceptable cations referred to above may find use, for example, in the preparation of compounds of formula (I) and the physiologically acceptable solvates thereof, and such salts also form part of the invention.

The compounds of formula (I) except those wherein $R^4$ represents a cation may be converted into physiologically acceptable acid addition salts. Such acid addition salts are included within the scope of the present invention.

It will be appreciated that compounds of formula (I) possess at least two asymmetric carbon atoms namely the two carbon atoms (numbered 3 and 5) bearing the hydroxy groups in formula (a) and the carbon atom (numbered 4) bearing the group $R^5$ and the carbon atom (numbered 6) attached to X in formula (b) above.

In addition, in the compounds of formula (I) X may be

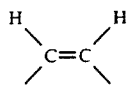

i.e. in the (Z) configuration, or X may be

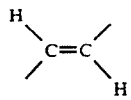

i.e. in the (E) configuration.

The compounds according to the invention thus include all stereoisomers and mixtures thereof, including the racemates.

In the compounds of formula (I) where Z represents a group of formula (a) the two diastereoisomeric pairs resulting from the two centres of asymmetry are hereinafter referred to as the threo and erythro isomers, threo and erythro referring to the relative configuration of the two hydroxy groups in the 3- and 5-positions.

In the compounds of formula (I) where Z represents a group of formula (b) the two diastereoisomeric pairs resulting from the two centres of asymmetry are hereinafter referred to as the cis and trans isomers, cis and trans referring to the relative configuration of the hydrogen atom and the group $R^5$ in the 6- and 4-positions respectively.

in the threo and cis isomers of the compounds of the invention the two asymmetric carbon atoms each have the same absolute configuration and thus the term threo and/or cis includes the R,R and S,S enantiomers and mixtures thereof including the racemates.

In the erythro and trans isomers of the compounds of the invention the two asymmetric carbon atoms have different absolute configurations and thus the term erythro and/or trans includes the R,S and S,R enantiomers and mixtures thereof including the racemates.

In the general formula (I) the groups $R^1$, $R^2$ and $R^3$ may represent a phenyl group or a pyridyl ring or N-oxide thereof. When $R^1$, $R^2$ or $R^3$ represents a pyridyl ring or N-oxide thereof this may be attached to the rest of the molecule at the 2-, 3- or 4-position. The phenyl and pyridyl groups represented by $R^1$, $R^2$ and $R^3$ may for example contain one or more substituents, which may be present at any vacant positions on the phenyl or pyridyl rings. Examples of suitable phenyl and pyridyl substituents include fluorine, chlorine, bromine or iodine atoms or methyl, ethyl, n-propyl, isopropyl, methoxy, ethoxy, n-propoxy, isopropoxy, trifluoromethyl or hydroxy groups. The terms "alkyl" and "alkoxy" when referred to hereinafter as suitable substituents contained within the definitions of $R^1$, $R^2$ and $R^3$ relate to $C_{1-3}$alkyl and $C_{1-3}$alkoxy groups respectively.

Thus, for example, when $R^1$, $R^2$ or $R^3$ represents a monosubstituted phenyl group this may be a 2-halo, a 3-halo (e.g. 3-bromo or 3-chloro), a 4-halo (e.g. 4-chloro or 4-fluoro), a 2-alkyl, a 3-alkyl, a 4-alkyl (e.g. 4-methyl), a 2-alkoxy, a 3-alkoxy (e.g. 3-methoxy), a 4-alkoxy (e.g. 4-methoxy), a trifluoromethyl such as a 3-trifluoromethyl or 4-trifluoromethyl, or a hydroxy such as a 3-hydroxy or 4-hydroxy substituted phenyl group.

When $R^1$, $R^2$ or $R^3$ represents a disubstituted phenyl group this may be for example a dihalo such as a 2,3- dihalo, a 2,4-dihalo, a 2,5-dihalo, a 2,6-dihalo, a 3,4-dihalo or a 3,5-dihalo (e.g. 3,5-dibromo or 3,5-dichloro), a dialkyl such as a 2,3-dialkyl a 2,4-dialkyl, a 2,5-dialkyl, a 3,4-dialkyl, a 3,5-dialkyl (e.g. 3,5-dimethyl), or an alkyl-halo such as a methyl-fluoro (e.g. 4-fluoro-2-methyl) or methyl-chloro (e.g. 5-chloro-2-methyl) substituted phenyl group.

When $R^1$, $R^2$ or $R^3$ represents a trisubstituted phenyl group this may be for example a dialkyl-halo such as a dimethyl-halo (e.g. 4-chloro-3,5-dimethyl or 3,5-dimethyl-4-fluoro) or diethyl-halo (e.g. 3,5-diethyl-4-fluoro) substituted phenyl group.

In the compounds of formula (I) $R^1$ or $R^2$ may represent a $C_{1-6}$alkyl group such as a methyl, ethyl, n-propyl, isopropyl, n-butyl, isobutyl, tertbutyl, n-pentyl or n-hexyl group. $R^1$ or $R^2$ may also represent a $C_{1-6}$alkyl group as defined above optionally substituted by one, two or three fluorine, chlorine, bromine or iodine atoms. For example $R^1$ or $R^2$ may represent a $C_{1-4}$alkyl (e.g. methyl or more particularly a branched $C_{3-4}$alkyl) group or a trifluoromethyl group.

In the compounds of formula (I) where Z represents a group of formula (a) and $R^4$ represents a physiologically acceptable cation this may include alkali metal (e.g. sodium or potassium) and alkaline earth metal (e.g. calcium or magnesium) cations.

Suitable physiologically acceptable acid addition salts of the compounds of formula (I) include salts formed with inorganic or organic acids (for example hydrochlorides, hydrobromides, sulphates, phosphates, p-toluenesulphonates and methanesulphonates).

Where $R^4$ represents a carboxyl protecting group this may include for example the residue of an ester-forming aliphatic or araliphatic alcohol. Such esters may find use in the preparation of other compounds of formula (I). In addition, compounds where $R^4$ represents an optically active ester group may find use in the separation of enantiomeric mixtures.

Where a compound of general formula (I) is to be used in medicine and $R^4$ represents a carboxyl protecting ester group this group should be physiologically acceptable and metabolically labile. Examples of such groups include lower alkyl groups such as $C_{1-4}$ alkyl (e.g. methyl, ethyl, n-propyl, isopropyl, n-butyl, isobutyl, tertbutyl) groups and aralkyl (e.g. benzyl) groups.

$R^5$ in the general formula (I) may represent a hydrogen atom or a methyl, ethyl, n-propyl or isopropyl group.

As indicated above, the compounds of the invention are active inhibitors of the enzyme HMG-CoA reductase and/or are of use as intermediates for the preparation of other active compounds. In general, when the compounds of the invention are to be used as intermediates the group $R^4$ will often be a carboxyl protecting group. Compounds wherein $R^4$ represents a physiologically acceptable ester group may serve as either intermediates or active compounds.

A preferred group of compounds of formula (I) are those wherein $R^5$ represents a methyl group or more particularly a hydrogen atom.

When in the compounds of formula (I) Z represents the group (a) this is preferably in the erythro configuration as defined above, and when Z represents the group (b) then this is preferably in the trans configuration as defined above.

A preferred group of compounds of formula (I) wherein Z represents a group (a) are the erythro enantiomers having the 3R,5S configuration and mixtures containing said enantiomers including the racemates.

A preferred group of compounds of formula (I) wherein Z represents a group (b) are the trans enantiomers having the 4R,6S configuration and mixtures containing said enantiomers including the racemates.

A particularly preferred group of compounds of formula (I) are the 3R,5S enantiomers where Z represents a group (a) substantially free of the corresponding 3S,5R enantiomers and the 4R,6S enantiomers where Z represents a group (b) substantially free of the corresponding 4S,6R enantiomers.

Compounds of formula (I) wherein X is in the (E) configuration as defined above are preferred.

A preferred group of compounds of formula (I) are those wherein $R^1$ represents a $C_{1-6}$alkyl group optionally substituted by one to three halogen atoms for example a trifluoromethyl or a $C_{1-4}$alkyl group, more particularly a $C_{3-4}$ branched alkyl group. Within this class of compounds a preferred group includes those compounds wherein $R^2$ is an optionally substituted phenyl group and $R^3$ is a pyridyl group or N-oxide thereof or an optionally substituted phenyl group.

When $R_3$ and/or $R_2$ represent a substituted phenyl group then these preferably contain from 1 to 3 substituents. Examples of suitable substituents include halogen atoms e.g. fluorine, bromine, chlorine, methoxy, methyl, ethyl, hydroxy or trifluoromethyl groups.

Preferred substituted phenyl groups include halophenyl such as 4-fluorophenyl, 4-chlorophenyl, 3-chlorophenyl, 3-bromophenyl, 3,5-dibromophenyl, 3,5-dichlorophenyl, alkyl-halophenyl such as 5-chloro-2-methylphenyl, 4-fluoro-2-methylphenyl, 3,5-dimethyl-4-fluorophenyl, 4-chloro-3,5-dimethylphenyl and 3,5-diethyl-4-fluorophenyl, alkylphenyl such as 4-methylphenyl, 3,5-dimethylphenyl, hydroxyphenyl, methoxyphenyl or trifluoromethylphenyl.

A particularly preferred group of compounds are those wherein $R^1$ represents a trifluoromethyl, t-butyl or more especially an isopropyl group, $R^2$ represents a phenyl, 3-chlorophenyl, 4-chlorophenyl, 4-fluorophenyl, 4-fluoro-2-methylphenyl, 3,5-diethyl-4-fluorophenyl or 3,5-dimethyl-4-fluorophenyl group and $R^3$ represents a phenyl, 3-chlorophenyl, 3-bromophenyl, 4-fluorophenyl, 4-chlorophenyl, 3,5-dibromophenyl, 3,5-dichlorophenyl, 5-chloro-2-methylphenyl, 4-fluoro-2-methylphenyl, 3,5-dimethyl-4-fluorophenyl, 4-chloro-3,5-dimethyl, 4-methylphenyl, 3,5-dimethylphenyl, 3-hydroxyphenyl, 4-hydroxyphenyl, 3-methoxyphenyl, 4-methoxyphenyl, 3-trifluoromethylphenyl, 3-pyridinyl or 4-pyridinyl group and $R^5$ represents hydrogen.

Within this particularly preferred group of compounds those in which $R^2$ represents a 4-fluorophenyl group are especially preferred.

Particularly preferred compounds of the invention are (±)-erythro-(E)-7-[4,5-bis(4-fluorophenyl)-2-(1-methylethyl)-1H-imidazol-1-yl]-3,5-dihydroxy-6-heptenoic acid more especially the 3R,5S enantiomer, and physiologically acceptable salts and esters and solvates, more especially the sodium salt thereof and (±)-trans-(E)-6-[2-[4,5-bis(4-fluorophenyl)-2-(1-methylethyl)-1H-imidazol-1-yl]ethenyl]-4-hydroxytetrahydro-2H-pyran-2-one, more especially the 4R,6S enantiomer, and physiologically acceptable acid addition salts and solvates thereof.

Further preferred compounds of the invention are (±)-erythro-(E)-7-[4-(3-chlorophenyl)-5-(4-fluorophenyl)-2-(1-methylethyl-1H-imidazol-1-yl]-3,5-dihydroxy-6-heptenoic acid;

(±)-erythro-(E)-7-[4-(3-bromophenyl)-5-(4-fluorophenyl-2)-(1-methylethyl)-1H-imidazol-1-yl]-3,5-dihydroxy-6-heptenoic acid;

(±)-erythro-(E)-7-[4-(3,5-dibromophenyl)-5-(4-fluorophenyl)-2-(1-methylethyl)-1H-imidazol-1-yl]-3,5-dihydroxy-6-heptenoic acid;

(±)-erythro-(E)-3,5-dihydroxy-7-[4-(3,5-dimethylphenyl)-5-(4-fluorophenyl)-2-(1-methylethyl)-1H-imidazol-1-yl]-6-heptenoic acid;

(±)-erythro-(E)-3,5-dihydroxy-7-[4-(3,5-dimethyl-4-fluorophenyl)-5-(4-fluorophenyl)-2-(1-methylethyl)-1H-imidazol-1-yl]-6-heptenoic acid;

(±)-erythro-(E)-3,5-dihydroxy-7-[5-(4-fluorophenyl)-4-(3-methoxyphenyl)-2-(1-methylethyl)-1H-imidazol-1-yl]-6-heptenoic acid;

(±)-erythro-(E)-3,5-dihydroxy-7-[5-(4-fluorophenyl)-2-(1-methylethyl)-4-(3-pyridinyl)-1H-imidazol-1-yl]-6-heptenoic acid;

(±)-erythro-(E)-7-[4-(3,5-dichlorophenyl)-5-(4-fluorophenyl)-2-(1-methylethyl)-1H-imidazol-1-yl]-3,5-dihydroxy-6-heptenoic acids;

(±)-erythro-(E)-3,5-dihydroxy-7-[5-(4-fluorophenyl)-2-(1-methylethyl)-4-(4-methylphenyl)-1H-imidazol-1-yl]-6-heptenoic acid;

(±)-erythro-(E)-3,5-dihydroxy-7-[5-(4-fluorophenyl)-4-(3-hydroxyphenyl)-2-(1-methylethyl)-1H-imidazol-1-yl]-6-heptenoic acid;

(±)-erythro-(E)-7-[4-(4-chloro-3,5-dimethylphenyl)-5-(4-fluorophenyl)-2-(1-methylethyl)-1H-imidazol-1-yl]-3,5-dihydroxy-6-heptenoic acid;

(±)-erythro-(E)-3,5-dihydroxy-7-[5-(4-fluorophenyl)-2-(1-methylethyl)-4-(4-pyridinyl)-1H-imidazol-1-yl]-6-heptenoic acid;

(±)-erythro-(E)-7-[4-(3,5-diethyl-4-fluorophenyl)-5-(4-fluorophenyl)-2-(1-methylethyl)-1H-imidazol-1-yl]-3,5-dihydroxy-6-heptenoic acid;

(±)-erythro-(E)-7-[4-(5-chloro-2-methylphenyl)-5-(4-fluorophenyl)-2-(1-methylethyl)-1H-imidazol-1-yl]-3,5-dihydroxy-6-heptenoic acid;

(±)-erythro-(E)-3,5-dihydroxy-7-[5-(4-fluorophenyl)-4-(4-hydroxyphenyl)-2-(1-methylethyl)-1H-imidazol-1-yl]-6-heptenoic acid;

(±)-erythro-(E)-3,5-dihydroxy-7-[4-(4-fluoro-2-methylphenyl)-5-(4-fluorophenyl)-2-(1-methylethyl)-1H-imidazol-1-yl]-6-heptenoic acid;

(±)-erythro-(E)-3,5-dihydroxy-7-[4-(4-chlorophenyl)-5-(4-fluorophenyl)-2-(1-methylethyl)-1H-imidazol-1-yl]-6-heptenoic acid;

(±)-erythro-(E)-3,5-dihydroxy-7-[5-(4-fluorophenyl)-4-(4-methoxyphenyl)-2-(1-methylethyl)-1H-imidazol-1-yl]-6-heptenoic acid;

(±)-erythro-(E)-3,5-dihydroxy-7-[5-(4-fluoro-2-methylphenyl)-4-(4-fluorophenyl)-2-(1-methylethyl)-1H-imidazol-1-yl]-6-heptenoic acid;

(±)-erythro-(E)-7-[4-(3-bromophenyl)-5-(3,5-dimethyl-4-fluorophenyl)-2-(1-methylethyl)-1H-imidazol-1-yl]-3,5-dihydroxy-6-heptenoic acid;

(±)-erythro-(E)-3,5-dihydroxy-7-[4-(3,5-dimethyl-4-fluorophenyl)-5-phenyl-2-(1-methylethyl)-1H-imidazol-1-yl]-6-heptenoic acid;

(±)-erythro-(E)-7-[5-(4-chlorophenyl)-4-(4-fluorophenyl)-2-(1-methylethyl)-1H-imidazol-1-yl]-3,5-dihydroxy-6-heptenoic acid;

(±)-erythro-(E)-7-[5-(4-fluorophenyl)-4-phenyl-2-(trifluoromethyl)-1H-imidazol-1-yl]-3,5-dihydroxy-6-heptenoic acid;

(±)-erythro-(E)-3,5-dihydroxy-7-[5-(4-fluorophenyl)-2-(1-methylethyl)-4-(3-trifluoromethylphenyl)-1H-imidazol-1-yl]-6-heptenoic acid;

(±)-erythro-(E)-7-[5-(3-chlorophenyl-4-(4-fluorophenyl)-2-(1-methylethyl)-1H-imidazol-1-yl]-3,5-dihydroxy-6-heptenoic acid;

(±)-erythro-(E)-7-[4,5-bis(4-fluorophenyl)-2-(1,1-dimethylethyl)-1H-imidazol-1-yl]-3,5-dihydroxy-6-heptenoic acid;

(±)-erythro-(E)-3,5-dihydroxy-7-[5-(4-fluorophenyl)-2-(1-methylethyl)-4-phenyl-1H-imidazol-1-yl]-6-heptenoic acid and the corresponding lactones and physiologically acceptable salts and esters and solvates, more especially the sodium salts thereof.

Besides having the utility set forth hereinbefore and hereinafter, every compound of formula (I) is useful as an intermediate in the synthesis of one or more other compounds of formula (I) utilising process (D) described hereinafter.

The compounds of formula (I) and physiologically acceptable solvates thereof are inhibitors of the enzyme HMG-CoA reductase as demonstrated by their performance in standard in vitro assays known in the art.

Thus, the compounds of formula (I) and their physiologically acceptable solvates inhibit cholesterol biosynthesis and are useful for lowering the level of blood plasma cholesterol in animals, e.g. mammals, especially larger primates, in particular humans, and, therefore the compounds of formula (I) are useful for the treatment and/or prevention of diseases associated with hypercholesterolemia and hyperlipoproteinemia especially atherosclerosis and coronary heart disease.

Many N-vinyl compounds are well known to be of low chemical stability and it is surprising that the compounds of the invention have proved to have high chemical stability.

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in a conventional manner with the aid of one or more suitable carriers or excipients. The compositions of the invention include those in a form especially formulated for oral, buccal, parenteral, implant, or rectal administration or in a form suitable for administration by inhalation or insufflation. Oral administration is preferred.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example. sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid. The compositions may also be formulated as suppositories, e.g. containing conventional suppository bases such as cocoa butter or other glycerides.

For buccal administration the composition may take the form of tablets or lonzenges formulated in conventional manner.

The composition according to the invention may be formulated for parenteral administration by injection or continuous infusion. Formulations for injection may be presented in unit dose form in ampoules, or in multidose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compositions according to the invention are conveniently delivered in the form an aerosol spray presentation from pressurized packs with the use of a suitable propellant, e.g. dichlorodifluoromethane, trichlorofluoromethane, dichlorotetrafluoroethane, carbon dioxide or other suitable gas, or from a nebuliser. In the case of a pressurized aerosol the dosage unit may be determined by providing a valve to deliver a metered amount.

Alternatively, for administration by inhalation the compositions according to the invention may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insufflator.

The composition according to the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

When the compositions comprise dosage units, each unit will preferably contain 0.1 mg to 500 mg, advantageously where the compounds are to be administered orally 1 mg to 400 mg of the active compound. The daily dosage as employed for adult human treatment will preferably range from 0.1 mg to 2000 mg most preferably from 1 mg to 200 mg which may be administered in 1 to 4 daily doses, for example, depending on the route of administration and on the condition of the patient.

The pharmaceutical composition according to the invention may be administered in combination with other therapeutic agents.

Compounds of general formula (I) and salts and solvates thereof may be prepared by the general methods outlined hereinafter. In the following description, the groups $R^1$-$R^5$ and X and Z are as defined for the compounds of general formula (I) unless otherwise stated.

According to a first general process (A) compounds of general formula (I) where Z is a group of formula (a) and $R^5$ is a hydrogen atom may be prepared by reduction of compounds of formula (II)

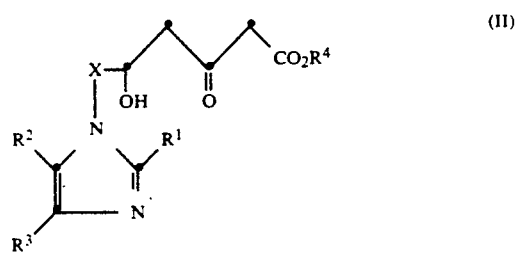

where $R^4$ is as defined in formula (I) above (e.g. a lower alkyl group) with a suitable reducing agent, followed by deprotection where appropriate if a compound of formula (I) in which $R^4$ is a hydrogen atom or a cation is required. Suitable reducing agents include for example metal hydrides such as sodium borohydride.

Reduction with sodium borohydride may optionally be carried out after prior in situ complexation of the compounds of formula (II) with a trialkylborane (e.g. triethylborane or tributylborane) or an alkoxydialkylborane (e.g. methoxydiethylborane).

The reduction conveniently takes place in a protic solvent such as an alcohol (e.g. methanol or ethanol) preferably in the presence of a cosolvent such as an ether (e.g. tetrahydrofuran) at a temperature in the range of $-80°$ to $30°$ C. (preferably $-80°$ to $-40°$ C.).

Compounds of formula (II) may be prepared by reaction of the aldehydes of formula (III)

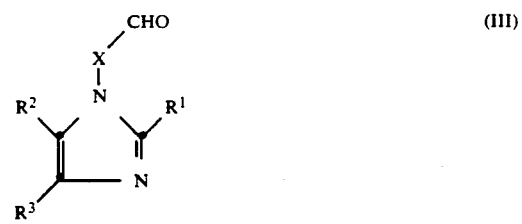

with diketene or a compound of formula (IV)

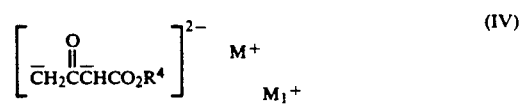

where $M^+$ and $M_1^+$ are metal cations, (e.g. sodium and lithium cations) conveniently prepared in situ from the reaction of

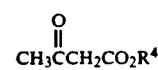

with a base such as a hydride (e.g. sodium hydride) followed by treatment with a strong base such as n-butyllithium or lithium diisopropylamide or alternatively by treatment with two equivalents of a strong base, conveniently in a suitable solvent such as an ether (e.g. tetrahydrofuran) or a hydrocarbon (e.g. hexane) or a mixture thereof at a temperature in the range of $-78°$ C. to room temperature (e.g. $-10°$ to $+20°$ C.).

The reaction with diketene may take place in the presence of a Lewis acid (e.g. titanium tetrachloride) conveniently in a suitable solvent such as a halogenated hydrocarbon (e.g. dichloromethane) at a temperature in the range of $-80°$ to $-50°$ C. followed by subsequent addition of an alcohol $R^4OH$ at a temperature in the range of $-30°$ to $-10°$ C.

Compounds of formula (III) may be prepared by the reduction of a compound of formula (V)

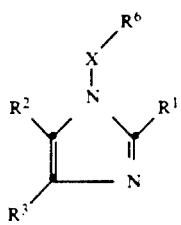 (V)

where $R^6$ represents a group $C\equiv N$ or a carboxylic ester group.

The reduction may be effected for example using a metal hydride reducing agent such as a dialkylaluminium hydride e.g. diisobutyl aluminium hydride, conveniently in the presence of a solvent such as a halogenated hydrocarbon (e.g. dichloromethane) or an ether (e.g. tetrahydrofuran) at a temperature in the range of $-80°$ to $+30°$ C.

When the group $R^6$ represents a carboxylic ester in the compounds of formula (V), reduction under the above conditions can produce the corresponding alcohols which may be oxidised to the aldehydes of formula (III) using a suitable oxidising agent, for example activated manganese dioxide, pyridinium chlorochromate or pyridinium dichromate in a suitable solvent (e.g. dichloromethane) at ambient temperature.

Compounds of formula (V) may be prepared by reacting the corresponding imidazole of formula (VI) with a compound of formula (VII)

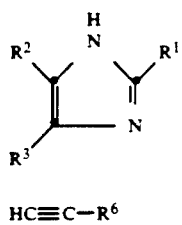 (VI)

$HC\equiv C-R^6$ (VII)

where $R^6$ as defined in formula (V) above.

The reaction may take place optionally in the presence of a base such as a tertiary amine (e.g. triethylamine) or potassium bis(trimethylsilyl)amide and with or without the presence of a suitable solvent such as an ether (e.g. tetrahydrofuran) at a temperature in the range of $0°$ to reflux.

Compounds of formula (V) may also be prepared by reacting the corresponding imidazole of formula (VI) with a compound of formula (VIIIa) or (VIIIb)

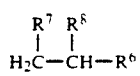 (VIIIa)

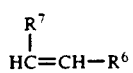 (VIIIb)

wherein $R^6$ is as defined in formula (V) above and $R'$ and $R^8$, which may be the same or different, may each represent suitable leaving groups for example halogen atoms (e.g. chlorine, bromine or iodine), acyloxy groups for example sulphonyloxy groups (e.g. trifluoromethanesulphonyloxy, p-toluenesulphonyloxy or methanesulphonyloxy).

The reaction may take place in the presence of a base (e.g. sodium hydride or triethylamine and/or potassium carbonate) conveniently in a suitable solvent such as an amide (e.g. dimethylformamide).

Compounds of formula (III) may also be prepared by reacting the imidazoles of formula (VI) with propiolaldehyde. The reaction may be effected in a suitable solvent such as an ether (e.g. tetrahydrofuran) at an elevated temperature.

When aldehydes of formula (III) are required where X is in the (E) configuration these compounds may conveniently be prepared photochemically from compounds of formula (III) where X is in the (Z) configuration or mixtures of geometric isomers. Thus for example compounds of formula (III) having a mixture of (E) and (Z) isomers or containing the (Z) isomer alone may be converted into compounds having the (E) configuration by irradiation with, for example, a tungsten lamp. The reaction may be effected in the presence of a suitable solvent such as a halohydrocarbon (e.g. carbontetrachloride) and in the presence of iodine at an elevated temperature.

Compounds of formulae (VII) and (VIII) are either known compounds or may be prepared from known compounds using conventional procedures.

It will be appreciated that the imidazoles of formula (VI) are tautomeric with corresponding compounds in which the $=N-$ and $-NH-$ groupings are reversed and that as a consequence, reaction of a compound of formula (VI) with a compound of formula (VII), (VIII) or propiolaldehyde can give a mixture of products in which the groups $R^2$ and $R^3$ are reversed. Such mixtures, however, may be separated readily for example by chromatography e.g. preparative HPLC at any convenient stage in the reaction scheme.

When preparing compounds of the invention wherein one of the imidazole substituents $R^1$, $R^2$ or $R^3$ represents a pyridyl ring, it may be desirable for some reaction steps to convert the pyridyl group into its corresponding N-oxide.

For example when reacting an imidazole of formula (VI) with a compound of formula (VII) or (VIII) or propiolaldehyde it may be desirable to have any pyridyl groups present in the N-oxide form.

The pyridyl N-oxides may be prepared by oxidising the appropriate pyridyl compound using a suitable oxidising agent such as m-chloroperbenzoic acid. Oxidation conveniently takes places in a suitable solvent such as a halogenated hydrocarbon (e.g. chloroform) at ambient temperature.

Reduction of the N-oxides may be effected using a suitable reducing agent such as a metal hydride (e.g. diisobutylaluminium hydride). Thus the N-oxides may be reduced under the conditions described above for the conversion of compounds of formula (V) into compounds of formula (III).

The imidazoles of formula (VI) may be prepared for example by the reaction of an α-diketone of formula (IX)

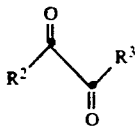
(IX)

with an aldehyde of formula (X)

R¹—CHO     (X)

or a protected derivative thereof (e.g. a hemiacetal) in the presence of ammonium acetate. conveniently in a suitable solvent such as acetic acid or acetic acid/acetic anhydride conveniently at a temperature in the range of 20°-150° C.

The imidazoles of formula (VI) may also be prepared by the reaction of an α-halocarbonyl compound of formula (XI)

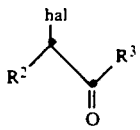
(XI)

where hal represents a halogen (e.g. bromine) atom with a compound of formula (XII)

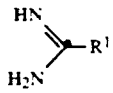
(XII)

optionally in the presence of a solvent such as a halogenated hydrocarbon or an alcohol or a mixture thereof at a temperature in the range of 20°-150° C. (e.g. 60° C.).

The imidazole intermediates of formula (VI) are novel compounds and thus form a further aspect of the present invention.

When a specific stereoisomer of a compound of formula (I) is required this may be prepared, for example, by resolution of the appropriate enantiomeric mixture of the compounds of formula (I) using conventional methods (see for example "Stereochemistry of Carbon Compounds" by E. L. Eliel (McGraw Hill 1962)).

Thus, where individual enantiomers of the compounds of formula (I) are required, these may be obtained from the enantiomeric mixtures of compounds of formula (I) by chromatography using a chiral column. Alternatively, enantiomeric mixtures of compounds of formula (I) where R⁴ is an optically active group may be separated for example using fractional crystallisation or chromatography. Enantiomeric mixtures of compounds of formula (I) where R⁴ is a hydrogen atom or a carboxyl protecting group may be separated by forming an acid addition salt with a suitable chiral acid (e.g. (1R)-7,7-dimethyl-2-oxabicyclo[2.2.1]-heptane-1-methane sulphonic acid).

Individual enantiomers of the compounds of formula (I) may also be obtained from the enantiomeric mixtures by selective enzymic hydrolysis.

Thus, a compound where the group —CO₂R⁴ is a group susceptible to enzymic hydrolysis may be used to obtain one enantiomer of the compound of formula (I) as the free acid and the other enantiomer as the non-hydrolysed compound.

Individual enantiomers of the compounds of formula (I) may also be obtained from intermediates having the required chirality. Such intermediates may be obtained on resolution of their enantiomeric mixtures where the intermediates concerned contain an appropriate chiral centre. For example the intermediates may contain a chiral protecting group. Alternatively, individual enantiomers may be obtained by stereoselective synthesis.

Thus, using general process (A) compounds of general formula (I) where Z is a group of formula (a) and R⁵ is a hydrogen atom may be prepared having a specific configuration about the 3- and 5-positions for example 3R,5S. in which case the final reduction step would be carried out on a chiral intermediate (IIa):

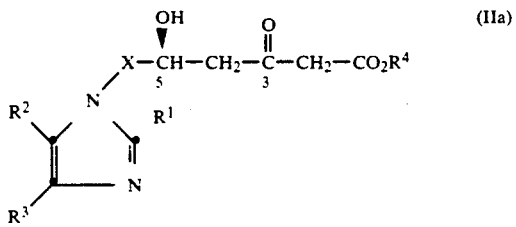
(IIa)

wherein R⁴ is as defined in formula (I) above (e.g. a lower alkyl group) using a stereoselective reducing agent. Suitable stereoselective reducing agents include for example metal hydrides such as sodium borohydride.

Reduction with sodium borohydride may optionally be carried out after prior in situ complexation of the compounds of formula (II) with a trialkylborane (e.g. triethylborane or tributylborane) or an alkoxydialkylborane (e.g. methoxydiethylborane).

The reduction conveniently takes place in a protic solvent such as an alcohol (e.g. methanol or ethanol) preferably in the presence of a cosolvent such as an ether (e.g. tetrahydrofuran) at a temperature in the range of −80° to 30° C. (preferably −80° to −40° C.).

Intermediate enantiomers of formula (IIa) where R⁴ represents a carboxyl protecting group (e.g. a lower alkyl group) may be prepared by deprotection of a compound of formula (XIII):

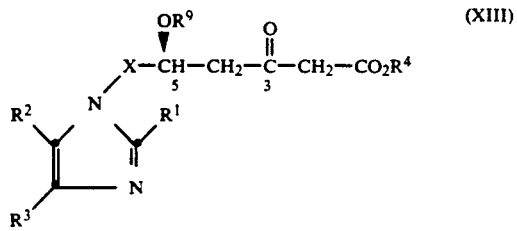
(XIII)

wherein R⁴ represents a carboxyl protecting group (e.g. a lower alkyl group) and R⁹ represents a chiral hydroxyl protecting group for example a chiral optionally substituted alkyl group such as a chiral alkanol (e.g. (R)-3-methylpropan-1-ol).

Deprotection of the hydroxyl group may be effected according to methods known in the art however it will be appreciated that such conditions will be chosen so as not to produce racemization at the C-5 carbon. Thus, for example, when $R^9$ represents a chiral alkanol such as the group

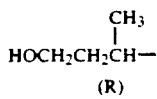

deprotection may be affected by oxidation to the corresponding aldehyde followed by selective $\beta$-elimination.

Suitable oxidising agents for the aforementioned step include periodinanes such as Dess-Martin periodinane (1,1,1-tri(acetyloxy)-1,1-dihydro-1,2-benziodoxol-3(1H)one). Selective $\beta$-elimination may take place in the presence of a suitable base for example dibenzylamine or a salt thereof such as the trifluoroacetate salt, conveniently in the presence of a suitable solvent such as a halohydrocarbon (e.g. dichloromethane).

Compounds of formula (XIII) where $R^9$ represents a group of formula

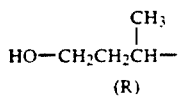

may be prepared by reacting an acetal of formula

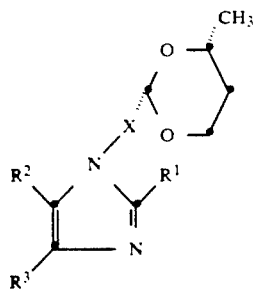

with diketene or a compound of formula (XV)

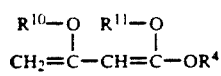

where $R^{10}$ and $R^{11}$, which may be the same or different, represent suitable enol stabilising groups and $R^4$ represents a carboxyl protecting group (e.g. a lower alkyl group), followed by removal of the enol stabilising groups.

The aforementioned reaction is highly diastereoselective and conveniently takes place in the presence of a pyridine (e.g. 2,6-di-t-butylpyridine) and a Lewis acid (e.g. titanium tetrachloride) as catalysts in a suitable solvent such as a halogenated hydrocarbon (e.g. dichloromethane) at a temperature in the range of $-70°$ to $-80°$ C. When diketene is employed as a reactant the reaction is followed by subsequent addition of an alcohol $R^4OH$ at a temperature in the range of $-30°$ to $-10°$ C.

Suitable enol stabilising groups represented by $R^{10}$ and $R^{11}$ include alkylsilyl groups such as trimethylsilyl groups. Such groups may be removed under conditions of acidic hydrolysis for example using tetrabutylammonium fluoride and acetic acid in a suitable solvent such as an ether (e.g. tetrahydrofuran) conveniently at room temperature.

Compounds of formula (XIV) may be prepared by reacting a compound of formula (III) with (R)-(−)-butane-1,3-diol in the presence of an acid catalyst such as p-toluenesulphonic acid. The reaction conveniently takes place in the presence of a suitable hydrocarbon solvent (e.g. toluene) at an elevated temperature such as the boiling point of the solvent.

Alternatively the chiral intermediates of formula (IIa) may be prepared by a Claisen condensation of a compound of formula (XVI)

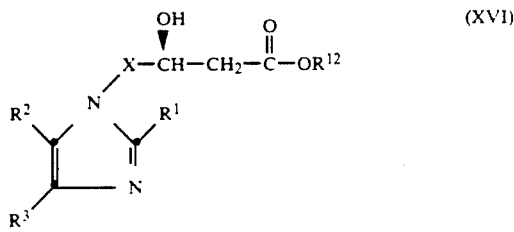

(where $R^{12}$ represents lower alkyl e.g. methyl) with a compound of formula (XVII)

where $R^4$ is a carboxyl protecting group such as a lower alkyl (e.g. t-butyl) group.

The reaction takes place in the presence of a strong base such as an amide (e.g. lithium diisopropylamide) conveniently in the presence of a suitable solvent such as an ether (e.g. tetrahydrofuran) or a cycloalkane (e.g. cyclohexane) or mixtures thereof at a temperature in the range of $-40°$ to $5°$ C.

Compounds of formula (XVI) where $R^{12}$ represents a lower alkyl (e.g. methyl) group may be prepared from compounds of formula (XVI) where $R^{12}$ represents a chiral carboxyl protecting group by transesterification.

Thus compounds of formula (XVI) where $R^{12}$ represents the chiral group

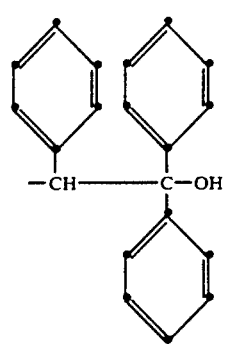

may be reacted with an alkoxide such as an alkali metal alkoxide (e.g. sodium methoxide) in the presence of the appropriate alcohol (e.g. methanol) as solvent.

Compounds of formula (XVI) where $R^{12}$ represents a chiral carboxyl protecting group may be prepared by reacting a compound of formula (III) with an enolate of formula (XVIII)

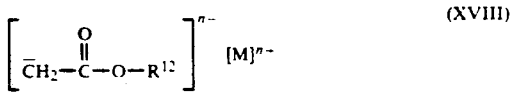

where $R^{12}$ represents a chiral carboxyl protecting group (for example the group

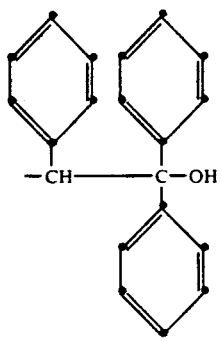

which will thus be in anionic form), M represents a metal (e.g. lithium or magnesium) cation (or cations) and n represents an integer (e.g. 1 or 2) depending on the nature of $R^{12}$ and M, conveniently in a suitable solvent such as an ether (e.g. tetrahydrofuran) at a temperature in the range of $-110°$ to $5°$ C. The enolate may conveniently be prepared in situ by the treatment of a compound $CH_3C(O)OR^{12}$ with a strong base such as lithium diisopropylamide or lithium dicyclohexylamide (in which case M represents lithium) conveniently in the presence of a suitable solvent such as an ether (e.g. tetrahydrofuran) at a temperature in the range of $-80°$ to $0°$ C. The enolate thus formed may optionally undergo transmetallation to replace M. Thus for example replacement of M (e.g. by a magnesium cation) may be effected by treatment of a compound of formula (XVIII) where M represents for example two lithium cations with a metal halide (e.g. magnesium bromide) in the presence of a suitable solvent such as an ether (e.g. tetrahydrofuran) at a temperature in the range of $-70°$ to $-80°$ C.

Compounds of formulae (XV), (XVII) and (XVIII) are either known compounds or may be prepared according to methods used for the preparation of known compounds.

According to a further general process (B) compounds wherein Z represents a group of formula (a) or (b) and $R^5$ represents a $C_{1-3}$ alkyl group may be prepared by nucleophilic addition of an alkyl acetate anion to a compound of formula (XIX)

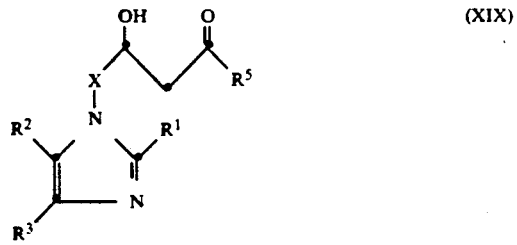

The alkyl acetate anion is conveniently prepared in situ from the action of a base such as a metal amide (e.g. lithium bis(trimethylsilyl)amide) on the corresponding alkyl acetate (e.g. methyl acetate).

The reaction conveniently takes place in a suitable solvent such as an ether (e.g. tetrahydrofuran) at a temperature in the range of $-80°$ to $-30°$ C. (e.g. $-78°$ C.).

Compounds of formula (XIX) may be prepared by reacting the aldehydes of formula (III) with a methyl ketone (e.g. acetone) in the presence of a base such as a metal amide (e.g. lithium bis(trimethylsilyl)amide). The reaction conveniently takes place in the presence of a suitable solvent such as an ether (e.g. tetrahydrofuran) at a temperature in the range of $-80°$ to $-30°$ C. (e.g. $-78°$ C.).

According to a further general process (C) compounds of formula (I) wherein Z represents a group of formula (a) and $R^5$ is a hydrogen atom may be prepared by reductive cleavage of compounds of formula (XX) followed by hydrolysis of the resulting imino compound

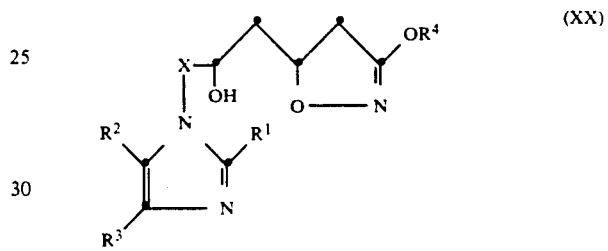

Reductive cleavage may take place under conventional conditions for example using hydrogen in the presence of a transition metal catalyst (e.g. Raney nickel). Hydrolysis may take place under acidic conditions for example using mineral (e.g. hydrochloric), organic (e.g. acetic) or inorganic (e.g. boric) acids or a mixture thereof.

The reaction conveniently takes place in the presence of a suitable solvent such as an aqueous alcohol (e.g. aqueous methanol) at ambient temperature.

When compounds of formula (XX) where $R^4$ represents hydrogen are used in the above reaction compounds of formula (I) may be obtained as amides. These may be converted into the corresponding acids according to conventional procedures.

Compounds of formula (XX) wherein $R^4$ represents a carboxyl protecting group such as a lower alkyl (e.g. methyl) group may be prepared by reacting a compound of formula (XXI)

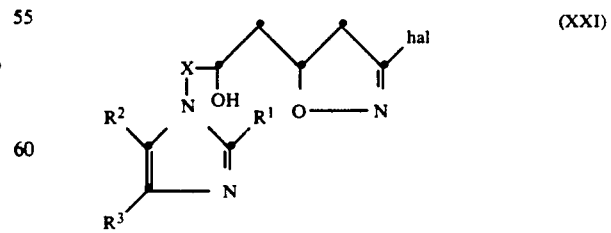

wherein hal represents a halogen (e.g. bromine) atom with an alkoxide. Suitable alkoxides include alkali metal alkoxides such as lithium alkoxides (e.g. lithium methoxide).

The reaction conveniently takes place in the presence of a solvent such as an alcohol (e.g. methanol) at an elevated temperature such as the reflux temperature of the solvent.

Compounds of formula (XX) wherein $R^4$ represents hydrogen or a cation may be prepared from compounds of formula (XX) where $R^4$ represents a carboxyl protecting group, according to conventional procedures, for example, in the case where $R^4$ is hydrogen, by treatment with trimethylsilyl iodide in a suitable solvent such as a halogenated hydrocarbon (e.g. dichloromethane) at a temperature in the range of $-78°$ C. to ambient.

Compounds of formula (XXI) may be prepared by reacting a compound of formula (XXII) with a dihaloformaldoxime (e.g. dibromoformaldoxime)

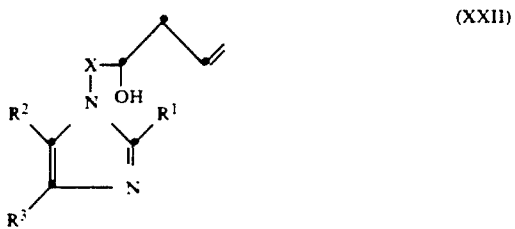

(XXII)

The reaction conveniently takes place in the presence of a base (e.g. sodium bicarbonate) in the presence of a suitable solvent such as an ester (e.g. ethyl acetate) in admixture with water, at ambient temperature.

Compounds of formula (XXII) may be prepared by allylation of aldehydes of formula (III). Allylation may be effected using an allyl metal e.g. an allyl Grignard reagent such as allylmagnesium chloride. The reaction conveniently takes place in the presence of a suitable solvent such as an ether (e.g. tetrahydrofuran) at a temperature ranging from 0° C. to ambient.

Intermediates of formulae (II), (IIa), (III), (V), (XIII), (XIV), (XVI), (XIX), (XX), (XXI) and (XXII) are novel compounds and form a further feature of the invention.

According to a further general process (D), a compound of formula (I) may be converted into another compound of formula (I) using conventional techniques. Such conventional techniques include protection and deprotection, lactonisation or base-catalysed cleavage, oxidation and hydrolysis as well as resolution of optical isomers as discussed above.

Lactonisation according to general process (D) may be used to convert a compound of general formula (I) where Z is a group of formula (a) into a compound of general formula (I) where Z is a group of formula (b) (where (a) and (b) are as defined in formula (I) above).

Thus, compounds of general formula (I) wherein Z is a group of formula (b) may be prepared by lactonization of a compound of formula (I) where Z is a group of formula (a) and $R^4$ is hydrogen or a cation, optionally in the presence of an acid (e.g. p-toluenesulphonic acid) conveniently in a suitable inert solvent such as a hydrocarbon (e.g. toluene) or a halohydrocarbon (e.g. dichloromethane) either at room temperature in the presence of a carbodiimide (e.g. 1-cyclohexyl-3-(2-morpholinoethyl)carbodiimide metho-p-toluenesulphonate) or at an elevated temperature e.g. from 50° C. to the reflux temperature of the solvent.

It will be understood that where racemic compounds of formula (I) where Z is a group (a) are used in the above mentioned lactonization step racemic compounds of formula (I) where Z is a group (b) will be produced. Likewise, where a single enantiomer of a compound of formula (I) is employed in the lactonization step a single enantiomer of formula (I) where Z is a group (b) will be produced. Thus, a racemic erythro compound of formula (I) where Z is a group (a) will give a racemic trans lactone, conversely, a racemic threo compound of formula (I) where Z is a group (a) will give a racemic cis lactone. As a further example a single erythro enantiomer e.g. a 3R,5S enantiomer of a compound of formula (I) where Z represents a group (a) will give a single trans lactone enantiomer e.g. a 4R,6S enantiomer.

Base-catalysed cleavage according to general process (D) may be used to convert a compound of general formula (I) where Z is a group of formula (b) into a compound of general formula (I) where Z is a group of formula (a).

Thus, compounds of general formula (I) wherein Z is a group of formula (a) and $R^4$ is a cation may be prepared by base-catalysed cleavage of compounds of formula (I) where Z is a group of formula (b). Suitable bases include hydroxides such as sodium hydroxide, potassium hydroxide or ammonium hydroxide. Alternatively, compounds of formula (I) wherein Z is a group of formula (a) and $R^4$ represents a carboxyl protecting group such as an ester group, may be prepared by base-catalysed cleavage of compounds of formula (I) where Z is a group of formula (b) in the presence of an alkoxide (e.g. sodium methoxide). The reaction may optionally take place in a solvent such as an ether (e.g. tetrahydrofuran) or an alcohol $R^4OH$ or a mixture thereof, at room temperature.

As mentioned above for the lactonization step, base catalysed cleavage of racemic starting materials will produce racemic products and base catalysed cleavage of single enantiomers will produce products as single enantiomers. Thus, by way of example, base catalysed cleavage of a 4R,6S trans lactone enantiomer will give a compound of formula (I) where Z is a group of formula (a) as a single enantiomer in the 3R,5S erythro configuration.

Deprotection according to general process (D) may be used to convert compounds of formula (I) where the group $R^4$ is a protecting group to compounds of formula (I) where the group $R^4$ is in a deprotected form (i.e. $R^4$ represents a hydrogen atom or a cation).

Deprotection may be effected using conventional techniques such as those described in 'Protective Groups in Organic Synthesis' by Theodora W. Green (John Wiley and Sons, 1981).

Thus, for example, compounds of formula (I) where $R^4$ represents a cation may be prepared by base catalysed hydrolysis of compounds of formula (I) where $R^4$ represents a carboxyl protecting group such as an alkyl group using a metal hydroxide (e.g. aqueous sodium hydroxide). The reaction optionally takes place in the presence of a co-solvent such as an ether (e.g. tetrahydrofuran) conveniently at room temperature.

The corresponding free acids of the salts thus formed may be prepared by treatment of the salt with dilute aqueous mineral acid (e.g. hydrochloric acid) at a suitable pH value.

Physiologically acceptable acid addition salts of the compounds of formula (I) may be prepared by treating the corresponding free base with a suitable acid using conventional methods. Thus, for example, a generally convenient method of forming the acid addition salts is to mix appropriate quantities of the free base and the acid in an appropriate solvent e.g. a nitrile such as acetonitrile.

Oxidation according to general process (D) may be used to convert a compound of general formula (I) where $R^1$, $R^2$ or $R^3$ represents a pyridyl ring into the corresponding N-oxide compound.

Thus, compounds of formula (I) wherein $R^1$, $R^2$ or $R^3$ represents a pyridyl N-oxide group may be prepared by oxidising the corresponding pyridyl compounds according to the methods described hereinbefore.

Hydrolysis according to general process (D) may be used to convert compounds of formula (I) where $R^1$, $R^2$ or $R^3$ represents an alkoxy substituted phenyl ring into a hydroxy substituted phenyl ring.

Hydrolysis may be carried out according to conventional procedures for example in the presence of a Lewis acid such as a boron trihalide (e.g. boron tribromide) in the presence of a suitable solvent such as a halogenated hydrocarbon (e.g. dichloromethane) at a temperature in the range of $-78°$ C. to ambient followed by cleavage of the derived complex by the addition of alcohol (e.g. methanol) optionally in the presence of a base (e.g. sodium bicarbonate).

The foregoing series of reactions involve a number of alternative pathways starting from the imidazole of formula (VI) as defined above. According to a further feature of the invention, therefore we provide a general process (E) for the preparation of compounds of formula (VI) as defined above in one or more stages with reagents serving to replace the N-attached hydrogen by a group —X—Z.

The following examples illustrate the invention. Temperatures are in ° C. 'Dried' refers to drying using magnesium sulphate. Thin layer chromatography (t.l.c.) was carried out on silica plates. Column chromatography (CC) was carried out on silica (Merck 7734) and flash column chromatography (FCC) was carried out on silica (Merck 9385). High pressure liquid chromatography (h.p.l.c.) was carried out on a Zorbax $NH_2$ column unless otherwise stated. The following solvent systems were used as elutants: System A-ethyl acetate:cyclohexane; System B-ethyl acetate:hexane. The following abbreviations are used: THF-tetrahydrofuran; DMSO-dimethylsulphoxide; ether-diethyl ether; DMF-dimethylformamide.

INTERMEDIATE 1

5-(4-Fluorophenyl)-4-phenyl-2-trifluoromethyl-1H-imidazole

A mixture containing impure 2-bromo-2-(4-fluorophenyl)-1-phenyl-ethanone (13.07 g) and trifluoroacetamidine (5.00 g) was heated at 60° under nitrogen and with stirring for 19 h. More trifluoroacetamidine (2.00 g) was added and after a further 3 h the mixture was allowed to cool to room temperature and dissolved in chloroform/methanol before purifying by FCC eluting with System A (1:9) to give the title compound (4.60 g) as a pale yellow solid. δ ($DMSO-d_6$) 7.16 and 7.2–7.6 (t, J 9 Hz and m, aromatic protons), 13.90 (bs, NH).

INTERMEDIATE 2

4,5-Bis(4-fluorophenyl)-2-trifluoromethyl-1H-imidazole

A mixture of 1,2-bis(4-fluorophenyl)ethan-1,2-dione (10.13 g) trifluoroacetaldehyde ethyl acetal (17.5 g) and anhydrous ammonium acetate (32 g) in glacial acetic acid (200 ml) was heated under reflux for 70 hours. The cooled solution was evaporated and the residue was partitioned between ethyl acetate (1 L) and saturated aqueous sodium hydrogen carbonate carefully to avoid excessive foaming. The organic solution was washed with saturated aqueous hydrogen carbonate until the aqueous solution was neutral to basic, then dried and filtered. Rotary evaporation gave a light orange solid (15.91 g) which was purified by CC eluting with cyclohexane→System B (3:7) to give the title compound (10.78 g) as a white solid. $\lambda_{max}$ (EtOH) 252.4 (12,830), 256.6 (13,120) and 264.4 nm (ε12,085).

INTERMEDIATE 3

(a)

(E)-3-[5(4)-(4-Fluorophenyl)-4(5)-phenyl-2-trifluoromethyl-1H-imidazol-1-yl]-2-propenenitrile Triethylamine (dried, 0.58 ml) was added to a mixture of 5-(4-fluorophenyl)-4-phenyl-2-trifluoromethyl-1H-imidazole (576 mg), 2,3-dibromopropionitrile (524 mg) and anhydrous potassium carbonate (260 mg) in DMF (4 ml) at room temperature under nitrogen. The resulting solution was stirred for 4 days at room temperature. The reaction was quenched with saturated aqueous sodium chloride (50 ml), extracted with dichloromethane (×5) and dried. Removal of the solvent gave a brown liquid (2.228 g) which was purified by FCC eluting with System A (1:9) to give the title compounds (287 mg) as a white solid. $\nu_{max}$ ($CHBr_3$) 2230 cm$^{-1}$ (C≡N).

(b)

(E)-3-[4,5-Bis(4-fluorophenyl)-2-trifluoromethyl-1H-imidazol-1-yl]-2-propenenitrile From 4,5-bis(4-fluorophenyl)-2-trifluoromethyl-1H-imidazole (3.045 g), 2,3-dibromopropionitrile (5.33 g), anhydrous potassium carbonate (3.1 g) and triethylamine (5.2 ml) in dry DMF (19 ml) by the process as described for the preparation of Intermediate (3a) to afford a dark brown residue which was purified by FCC using gradient elution with System A (5–15% with 5% incremental increase of ethyl acetate per 500 ml eluant) to afford the title compound (1.449 g) as a white solid. $\nu_{max}$ ($CHBr_3$) 2229 cm$^{-1}$ (C≡N).

INTERMEDIATE 4

(a)

(E)-3-[5(4)-(4-Fluorophenyl)-4(5)-phenyl-2-trifluoromethyl-1H-imidazol-1-yl]-2-propenal Diisobutylaluminium hydride (1M in dichloromethane, 0.7 ml) was added to a solution of (E)-3-[5(4)-(4-fluorophenyl)-4(5)-phenyl-2-trifluoromethyl-1H-imidazol-1-yl]-2-propenenitrile (201 mg) in dichloromethane (5 ml) at −78° under nitrogen. The resulting mixture was stirred at −78° for 1.5 h. The reaction was quenched with saturated aqueous ammonium chloride, extracted with dichloromethane (×4) and dried. Rotary-evaporation gave a yellow residue (207 mg) which was purified by FCC eluting with System A (1:9) to give the title compounds (185 mg) as a light brown solid. $\nu_{max}$ ($CHBr_3$) 2740 and 2850 (C—H of aldehyde) and 1700 cm$^{-1}$ (C=O);

(b)
(E)-3-[4,5-Bis(4-fluorophenyl)-2-trifluoromethyl-1H-imidazol-1-yl]-2-propenal From (E)-3-[4,5-bis(4-fluorophenyl)-2-trifluoromethyl-1H-imidazol-1-yl]-2-propenenitrile (484 mg) and diisobutylaluminum hydride (2.2 ml) in dry THF (15 ml) by the process as described for the preparation of Intermediate (4a) to afford a brown gum (0.53 g) which was purified by FCC eluting with System A (1:4) to afford the title compound (263 mg) as a yellow solid. $\nu_{max}$ (Nujol) 1692 cm$^{-1}$ (C=O).

INTERMEDIATE 5

5-(4-Fluorophenyl)-2-(1-methylethyl)-4-phenyl-1H-imidazole

To a stirred solution of 1-(4-fluorophenyl)-2-phenylethan-1,2-dione (1.0 g) in acetic acid (25 ml) and acetic anhydride (3 ml) containing ammonium acetate (5.0 g) was added isobutyraldehyde (0.5 g) and the reaction mixture was warmed to 110° for 2 h. The mixture was poured into aqueous ammonium hydroxide at 0° and the deposited solid was collected by filtration, then washed sequentially with ether and water then dried in vacuo to afford the title compound (1.09 g), $\lambda_{max}$ (EtOH) 252 (9550) and 287.8 nm (ε11,870).

INTERMEDIATE 6

4,5-Bis(4-fluorophenyl)-2-(1-methylethyl)-1H-imidazole

To a stirred solution of 1,2-bis(4-fluorophenyl)ethan-1,2-dione (10.99 g) in acetic acid (200 ml) containing ammonium acetate (24.08 g) was added isobutyraldehyde (4.22 g). The reaction mixture was stirred at 100° for 2 h, room temperature for 60 h and 100° for a further 3 h. The mixture was evaporated to dryness, and the resulting solid was dissolved in ethyl acetate (400 ml). The solution was washed with saturated aqueous sodium bicarbonate solution (2×400 ml), with water (300 ml); then dried and evaporated to give the title compound (10.64 g), $\lambda_{max}$ (EtOH) 250.0 (9397) and 284.4 nm (ε11,516).

INTERMEDIATE 7

(a) Methyl (E)-3-[5(4)-(4-fluorophenyl)-2-(1-methylethyl)-4(5)-phenyl-1H-imidazol-1-yl]-2-propenoate To a solution of impure 5-(4-fluorophenyl)-2-(1-methylethyl)-4-phenyl-1H-imidazole (1.31 g) in dry THF (25 ml) was added methyl propiolate (2.00 ml) and the resultant mixture was heated at reflux, under nitrogen and with stirring for 65 h. The reaction mixture was allowed to cool to room temperature and then purified by CC eluting with System A (1:6) to give the title compound (0.95 g), $\nu_{max}$ (CHBr$_3$) 1714 cm$^{-1}$ (C=O).

(b) Methyl (E)-3-[4,5-bis(4-fluorophenyl)-2-(1-methylethyl)-1H-imidazol-1-yl]-2-propenoate From 4,5-bis(4-fluorophenyl)-2-(1-methylethyl)-1H-imidazole (2.00 g) and methyl propiolate (2.55 g) by the process as described for the preparation of Intermediate (7a) to afford an orange solid which was purified by FCC eluting with System A (3:17) to afford the title compound (1.194 g) as a white solid. $\lambda_{max}$ (MeOH) 248.4 (22,180) and 300 (inf) nm (ε9410).

INTERMEDIATE 8

(a) (E)-3-[5(4)-(4-Fluorophenyl)-2-(1-methylethyl)-4(5)-phenyl-1H-imidazol-1-yl]-2-propenol To a solution of methyl (E)-3-[5(4)-(4-fluorophenyl)-2-(1-methylethyl)-4(5)-phenyl-1H-imidazol-1-yl]-2-propenoate (0.93 g) in dry dichloromethane (25 ml) at −78° under nitrogen was added diisobutyl aluminium hydride (1M solution in dichloromethane, 3.18 ml). The mixture was stirred at −78° for 2 h and then allowed to warm to room temperature. The reaction mixture was recooled to −78° and more diisobutyl aluminum hydride (3.18 ml) was added with stirring. After 0.75 h the reaction mixture was allowed to warm to room temperature, quenched with saturated aqueous ammonium chloride and extracted with dichloromethane. The extracts were combined, dried and evaporated to give a yellow solid which was purified by CC eluting with System A (2:3) to give the title compound (0.78 g) as an off white crystalline solid, $\nu_{max}$ (CHBr$_3$) 3600 and 3670 cm$^{-1}$ (O-H stretch).

(b) (E)-3-[4,5-Bis(4-fluorophenyl)-2-(1-methylethyl)-1H-imidazol-1-yl]-2-propenol From methyl (E)-3-[4,5-bis(4-fluorophenyl)-2-(1-methylethyl)-1H-imidazol-yl]-2-propenoate (1.150 g) and diisobutylaluminium hydride (1M in dichloromethane, 6.62 ml) by the process as described for the preparation of Intermediate (8a) to afford a white solid which was purified by FCC eluting with System A (2:3) to afford the title compound (0.866 g) as a white solid, $\lambda_{max}$ (EtOH) 255.2 (12,050) and 243.2 (inf) nm (ε10,915).

INTERMEDIATE 9

(a) (E)-3-[5(4)-(4-Fluorophenyl)-2-(1-methylethyl)-4(5)-phenyl-1H-imidazol-1-yl]-2-propenal To a stirred solution of (E)-3-[5(4)-(4-fluorophenyl)-2-(1-methylethyl)-4(5)-phenyl-1H-imidazol-1-yl]-2-propenol (0.77 g) in dichloromethane (80 ml) was added manganese (IV) oxide (11.38 g). After 1 h, the reaction mixture was filtered and the spent manganese (IV) oxide was washed sequentially with System A (1:1) and ethyl acetate. The filtrate was evaporated to give the title compound (0.55 g) as an off white crystalline solid, $\nu_{max}$ (CHBr$_3$) 1682cm$^{-1}$ (C=O).

(b) (E)-3-[4,5-Bis(4-fluorophenyl)-2-(1-methylethyl)-1H-imidazol-1-yl]-2-propenal From (E)-3-[4,5-bis(4-fluorophenyl)-2-(1-methylethyl)-1H-imidazol-1-yl]-2-propenol (0.301 g) and manganese (IV) oxide (2.101 g) by the process as described for the preparation of Intermediate (9a) to afford a yellow solid which was purified by FCC eluting with System A (2:3) to afford the title compound (0.225 g) as a white solid, $\lambda_{max}$ (EtOH) 260.0 (20,050) and 289.2 (inf) nm (ε10,890).

INTERMEDIATE 10

(a) Methyl (±)-(E)-7-[5(4)-(4-fluorophenyl)-2-(1-methylethyl)-4(5)-phenyl-1H-imidazol-1-yl]-5-hydroxy-3-oxo-6-heptenoate To a slurry of sodium hydride (60% dispersion in oil, 0.18 g, washed with dry THF (2×10 ml)), in THF (2 ml) at −3° under nitrogen was added methyl acetoacetate (0.21 ml). After 5 min, n-butyl lithium (1.6M in hexanes; 1.31 ml) was added and the resultant solution was stirred at −3° for 10 min. (E)-3-[5(4)-(4-fluorophenyl)-2-(1-methylethyl)-4(5)-phenyl-1H-imidazol-1-yl]-2-propenal (0.54 g) in THF (9 ml) was cannulated into the methyl acetoacetate dianion solution at −3°. After 0.5 h at −3° the cooling bath was removed and after a further 10 min the mixture was recooled to 0° and then quenched with saturated aqueous ammonium chloride (50 ml). The solution was extracted with dichloromethane (50 ml×4) and, the extracts were combined, dried, and evaporated to give a brown oil. This material was purified by CC eluting with System A (2:3) to give the title compound (0.47 g) as a pale yellow crystalline solid. $\lambda_{max}$ (EtOH) 245 (inf) (15,270), 257 (inf) (13,470), 265 (inf) nm ($\epsilon$12,704).

(b) Methyl (±)-(E)-7-[4,5-bis(4-fluorophenyl)-2-(1-methylethyl)-1H-imidazol-1-yl]-5-hydroxy-3-oxo-6-heptenoate From (E)-3-[4,5-bis(4-fluorophenyl)-2-(1-methylethyl)-1H-imidazol-1-yl]-2-propenal (0.100 g), methyl acetoacetate (0.028 ml), sodium hydride (0.031 g, washed with dry THF(3×3 ml)) and n-butyl lithium (1.4M in, hexanes, 0.26 ml) by the process as described for the preparation of Intermediate (10a) to afford a dark orange oil which was purified by FCC eluting with System A (2:3, 1:1) to afford the title compound (0.054 g) as an orange solid, Rf (System A 2:3) 0.18;

(c) Methyl(±)-(E)-7-[5(4)-(4-fluorophenyl)-4(5)-phenyl-2-trifluoromethyl-1H-imidazol-1-yl]-5-hydroxy-3-oxo-6-heptenoate From (E)-3-[5(4)-(4-fluorophenyl)-4(5)-phenyl-2-trifluoromethyl-1H-imidazol-1-yl]-2-propenal (0.17 g) by the process as described for the preparation of Intermediate (10a) to give a brown residue (237 mg) which was purified by FCC using gradient elution (30-35% System A with 1% incremental increase of ethyl acetate per 500 ml eluant) to give methyl (±)-(E)-7-[5-(4-fluorophenyl)-4-phenyl-2-trifluoromethyl-1H-imidazol-1-yl]-5-hydroxy-3-oxo-6-heptenoate (81.7 mg) as a pale yellow gum, $\nu_{max}$(CHBr$_3$) 3586 (OH), 1742 (ester C=O) and 1713 cm$^{-1}$ (ketone C=O); Later fractions gave methyl (±)-(E)-7-[4-(4-fluorophenyl)-5-phenyl-2-trifluoromethyl-1H-imidazol-1-yl]-5-hydroxy-3-oxo-6-heptenoate (87.7 mg) as a light brown solid, $\nu_{max}$(CHBr$_3$) 3568 (OH), 1742 (ester C=O) and 1713 cm$^{-1}$ (ketone C=O).

(d) Methyl (±)-(E)-7-[4,5-bis(4-fluorophenyl)-2-trifluoromethyl-1H-imidazol-1-yl]-5-hydroxy-3-oxo-6-heptenoate From (E)-3-[4,5-bis(4-fluorophenyl)-2-trifluoromethyl-1H-imidazol-1-yl]-2-propenal (0.253 g) by the process as described for the preparation of Intermediate (10a) to afford a brown residue (0.363 g) which was purified by FCC eluting with System A (30→40%) to afford the title compound (212.4 mg) as a straw coloured solid. $\nu_{max}$(CHBr$_3$) 3585 (OH), 1742 (C=O of ester) and 1713 cm$^{-1}$ (C=O of ketone).

INTERMEDIATE 11

(a) 3-[4,5-Bis(4-fluorophenyl)-2-(1-methylethyl)-1H-imidazol-1-yl]-2-propenal

To a solution of 4,5-bis(4-fluorophenyl)-2-(1-methylethyl)-1H-imidazole (492 mg) in dry THF under nitrogen was added propiolaldehyde (0.97 ml) and the reaction mixture heated to reflux. Further quantities of propiolaldehyde were added in portions (3×1.1 g) during successive 2 h periods. The reaction mixture was concentrated and the deep red residue was purified by FCC eluting with system A (1:4) to give the title product (398 mg) as an off-white solid and as a 1:1 mixture of geometric isomers. δ(CDCl$_3$) 9.48 (d, 1H, J 7.5 Hz, cis CHO), 9.40 (d, 1H, J 7.5 Hz, trans CHO), 7.5 (d, 1H, J 15 Hz, trans CH=CHCHO), 7.45–6.85 (m, 17H, aromatic protons and cis CH=CHCHO), 5.98 (t,1H,J 7.5 Hz, cis CH=CHCHO), 5.63 (dd, 1H, J 15 and 7.5 Hz, trans CH=CH CHO), 3.25 (septet, 1H, J 7 Hz, CH(CH$_3$)$_2$ of trans isomer), 3.05 (septet, 1H, J 7 Hz, CH(CH$_3$)$_2$ of cis isomer).

(b) (E)-3-[4,5-Bis(4-fluorophenyl)-2-(1-methylethyl)-1H-imidazol-1-yl]-2-propenal A solution of 4,5-bis(4-fluorophenyl)-2-(1-methylethyl)-1H-imidazole (200 mg) and propiolaldehyde (75% solution in toluene, 0.15 ml) in dry THF (15 ml) were heated under reflux, under nitrogen for 24 h. The residue was dissolved in acetone and absorbed onto silica gel before purifying by CC eluting with petroleum ether (b.p. 40°–60°)/ethyl acetate (2:1) to give the title compound (84 mg) as a pale yellow solid, δ(CDCl$_3$), 1.49 (d,J=7 Hz, Me$_2$CH), 3.25 (septet, J=7 Hz, Me$_2$CH), 5.67 (dd,J=15 Hz, 7 Hz,CH=CH.CHO), 6.95 and 7.10–7.60 (t,J=9 Hz and m, CH=CH.CHO and aromatic protons), 9.40 (d, J=7 Hz, CH=CH.CHO).

INTERMEDIATE 12

(E)-3-[4,5-Bis(4-fluorophenyl)-2-(1-methylethyl)-1H-imidazol-1-yl]-2-propenal

To a solution of 3-[4,5-bis(4-fluorophenyl)-2-(1-methylethyl)-1H-imidazol-1-yl]-2-propenal (390 mg) as an E:Z (1:1) mixture in carbon tetrachloride (150 ml) was added iodine (0.1 g) and the reaction mixture was heated under reflux for 18 h using a 200W-tungsten lamp. After this period, activated charcoal (6 g) was added and heating was continued for a further 1 h. The mixture was filtered and the resulting pale yellow solution was evaporated to yield the title compound (384 mg) as a dull-white solid whose spectroscopic properties were in accord with those described above for Intermediate 11a.

INTERMEDIATE 13

(a) (S)-1-Hydroxy-1,1,2-triphenyleth-2-yl (3S,E)-5-[4,5-bis(4-fluorophenyl)-2-(1-methylethyl)-1H-imidazol-1-yl]-3-hydroxy-4-pentenoate A solution of magnesium bromide was prepared by treating a suspension of magnesium turnings (58 mg) in dry THF (8 ml) under nitrogen at room temperature with 1,2-dibromoethane (0.21 ml). The reaction flask was then placed in an ultrasonic bath until the magnesium had dissolved. Dry ether (16 ml) was then added and the mixture cooled to −75°. A solution of dry diisopropylamine (0.42 ml) in dry THF (1.05 ml) under nitrogen at 3° was treated with a solution of n-butyl lithium (1.5M in hexanes, 2.0 ml). After 10 mins the solution was cannulated into a suspension of (S)-1-hydroxy-1,1,2-triphenyleth-2-yl acetate (400 mg) in dry THF (4 ml) under nitrogen at −75°. The mixture was then allowed to warm to 3° giving an orange solution. The solution was cooled to −75° and cannulated into the magnesium bromide mixture described above. After a further 1.5 h the mixture was cooled to −110° and a solution of (E)-3-[4,5-bis(4-fluorophenyl)-2-(1-methylethyl)-1H-imidazol-1-yl]-2-propenal (423 mg) in dry THF (6 ml) was added dropwise. After a further 2 h saturated aqueous ammonium chloride solution (1 ml) was added and the mixture allowed to warm to −75° when more ammonium chloride solution (5 ml) was added. When the temperature reached 15° the mixture was diluted with more ammonium chloride solution (30 ml) and then extracted with ethyl acetate (3×30 ml). The combined extracts were washed with water (30 ml), dried and evaporated to give a straw coloured foam (898 mg). Purification by FCC eluting with System A (1:2) gave the title compound (725 mg) as a white solid $v_{max}$ (CHBr$_3$) 2972 (OH), 1727 cm$^{-1}$ (C=O) (SS:SR=93:7, as determined by proton nmr and HPLC analysis).

(b) (S)-1-Hydroxy-1,1,2-triphenyleth-2-yl (3S,E)-5-[4,5-bis(4-fluorophenyl)-2-(1-methylethyl)-1H-imidazol-1-yl]-3-hydroxy-4-pentenoate A solution of dry dicyclohexylamine (2.49 ml) in dry THF (30 ml) under nitrogen at 3° was treated dropwise with a solution of n-butyl lithium (1.55M in hexanes, 8.06 ml). After 25 min the solution was cannulated dropwise into a stirred suspension of (S)-1-hydroxy-1,1,2-triphenyleth-2-yl acetate (1.828 g) in dry THF (60 ml) under nitrogen at −40°, plus washings (10 ml). When the addition was complete the mixture was allowed to warm to 3°. After 20 min the solution was cooled to −40° and treated with a solution of (E)-3-[4,5-bis(4-fluorophenyl)-2-(1-methylethyl)-1H-imidazol-1-yl]-2-propenal (1.762 g) in dry THF (35 ml) and washings (5 ml) at 3° dropwise. After 4 h the reaction mixture was treated with saturated aqueous ammonium chloride solution (20 ml) and allowed to warm. Water (200 ml) was then added and the mixture extracted with ethyl acetate (3×100 ml). The combined extracts were dried and evaporated and purified by FCC eluting with System A (7:3) to give the title compound (3.234 g) as a light brown foam, $v_{max}$(CHBr$_3$) 2971 (OH), 1729 cm$^{-1}$ (C=O) (SS:SR=93:7 as determined by pmr).

INTERMEDIATE 14

Methyl (3S,E)-5-[4,5-bis(4-fluorophenyl)-2-(1-methylethyl)-1H-imidazol-1-yl]-3-hydroxy-4-pentenoate A stirred suspension of (S)-1-hydroxy-1,1,2-triphenyleth-2-yl (3S,E)-5-[4,5-bis(4-fluorophenyl)-2-(1-methylethyl)-1H-imidazol-1-yl]-3-hydroxy-4-pentenoate (3.11 g) in methanol (30 ml) was treated with a solution of sodium (110 mg) in methanol (20 ml) plus methanol washings (2×5 ml). The resulting orange solution was stirred at room temperature for 2.5 h then the reaction mixture was concentrate. This was dissolved in dichloromethane (150 ml) and the solution was washed with water (50 ml) and brine (2×50 ml). The combined washings were extracted with dichloromethane (50 ml) and the combined organic phases were dried and evaporated to a pale buff solid (3.13 g). This was purified by CC eluting with System A 1:1 to give the title compound (1.588 g) as a white crystalline solid, $v_{max}$ (nujol) 1738 cm$^{-1}$ (C=O).

INTERMEDIATE 15

1,1-Dimethyleth-1-yl (5S,E)-7-[4,5-bis-(4-fluorophenyl)-2-(1-methylethyl)-1H-imidazol-1-yl]-5-hydroxy-3-oxo-6-heptenoate A solution of dry diisopropylamine (0.77 ml) in dry cyclohexane (15.6 ml) at 3° under nitrogen was treated dropwise with n-butyl lithium solution (1.55M in hexanes, 3.54 ml). After 15 min t-butyl acetate (0.74 ml) was added dropwise. After 30 min the mixture was cannulated into a solution of methyl (3S,E)-5-[4,5-bis(4-fluorophenyl)-2-(1-methylethyl)-1H-imidazol-1-yl]-3-hydroxy-4-pentenoate (334 mg) in dry THF (7.8 ml) at 3° under nitrogen over 15 min. After 1 h the mixture was quenched with saturated aqueous ammonium chloride solution (3.5 ml) and then diluted with water. The mixture was then and extracted with ethyl acetate (3×20 ml). The combined extracts were dried and evaporated to a gummy solid (518 mg) which was treated with ether (4 ml) and then cyclohexane (4 ml) and cooled in an ice bath. The solid was collected, washed and dried to give the title compound (239 mg) as a white powder; δ(CDCl$_3$) 1.41 (d, J7.5 Hz, 6H, CH(C$\underline{H}_3$)$_2$), 1.46 (s, 9H, C(C$\underline{H}_3$)$_3$), 2.59 (d, J7.5 Hz, 2H, C(O$\underline{H}$)CH$_2$CO), 3.02 (bs, 1H, OH), 3.14 (septet, J7.5 Hz, 1H, —C$\underline{H}$(CH$_3$)$_2$), 3.35 (s, 2H, C$\underline{H}_2$CO$_2$R), 4.63 (m, 1H, CHO$\underline{H}$), 5.39 (dd, J14 and 7 Hz, 1H, N—CH= CH—C), 6.70 (d, J14 Hz, 1H, N—C$\underline{H}$=CH—C), 6.90 and 7.10 (2t, J9 Hz, each 2H, C-3 and C-5 protons of 4-fluorophenyls), 7.17-7.47 (m, 4H, C-2 and C-6 protons of 4-fluorophenyls). Also present was a trace of the enol form, δ values include 1.52 (s, —C(C$\underline{H}_3$)$_3$), 4.51 (m, CHOH), 4.89 (s, C(OH)=CHCO$_2$), 5.38 (dd, J14 and 7 Hz, —N—C$\underline{H}$=CH), 6.64 (d, J14 Hz, NCH=C$\underline{H}$). Chiral hplc detected none of the other enantiomer. A second crop of title compound (56 mg) was also obtained.

INTERMEDIATE 16

(2S,4R,E) 4,5-Bis(4-fluorophenyl)-1-[(4-methyl-1,3-dioxan-2-yl)ethenyl]-2-(1-methylethyl)-1H-imidazole A mixture of (E)-3-[4,5-bis(4-fluorophenyl)-2-(1-methylethyl)-1H-imidazol-1-yl]-2-propenal (2.01 g), p-toluenesulphonic acid monohydrate (0.316 g) and (R)-(−)-butane-1,3-diol (98%, 1.37 g) in toluene (130 ml) was heated under reflux with a Dean-Stark trap for 20 h. The mixture was concentrated to ca. 30 ml and purified by FCC eluting with System A (1:4) to give the title product (1.78 g,) as a white solid. δ(CDCl$_3$) 1.23 (d, J 6 Hz, 3H, C$\underline{H}_3$CH—O), 1.42 (d, J 7 Hz, 6H, (C$\underline{H}_3$)$_2$CH), 1.55-1.8 (m, 2H, OCH(CH$_3$)CH$_2$CH$_2$O), 3.20 (septet, J 7 Hz, 1H, (CH$_3$)$_2$C$\underline{H}$), 3.7-3.9 (m, 2H, CH$_2$O), 4.05-4.16 (m, 1H, O—C$\underline{H}$(CH$_3$)), 4.95 (d, J 5 Hz, 1H, CH=CHC$\underline{H}$(O)$_2$), 5.32 (dd, J 15 and 5 Hz, 1H, NCH=C$\underline{H}$), 6.76 (dd, J 15 and 1 Hz, 1H, NC$\underline{H}$=CH), 6.89 (t, J 9 Hz, 2H, C-3 and C-5 protons of 4-(4-fluorophenyl)), 7.11 (t, J 9 Hz, 2H, C-3 and C-5 protons of 5-(4-fluorophenyl)), 7.39 and 7.27 (2 dd, J 9 and 6 Hz, 4H, C-2 and C-6 protons of both 4-fluorophenyls).

INTERMEDIATE 17

Methyl [5S,1'R, (E)] 7-[4,5-bis(4-fluorophenyl)-2-(1-methylethyl)-1H-imidazol-1-yl]-5-(3-hydroxy-1-methylpropoxy)-3-oxo-6-heptenoate To a mixture of (2S,4R,E) 4,5-bis(4-fluorophenyl)-1-[(4-methyl-1,3-dioxan-2-yl)ethenyl]-2-(1-methylethyl)-1H-imidazole (1.841 g), 2,6-di-t-butylpyridine (97%, 1.03 g) and 1,3-bis(trimethylsiloxy)-1-methoxybuta-1,3-diene (6.77 g) in dry dichloromethane (70 ml) at −78° under nitrogen, titanium tetrachloride (1M in dichloromethane, 17.8 ml) was added dropwise rapidly. After stirring for 1h, methanol (10 ml) was added and the reaction was quenched with saturated aqueous ammonium chloride at −78°. After warming to room temperature the organic solution was separated and washed with saturated aqueous sodium hydrogen carbonate. The combined aqueous solution was basified with saturated aqueous sodium hydrogen carbonate and extracted with dichloromethane (4×). Combined dichloromethane solutions were dried and evaporated to give a brown liquid (3.367 g). Purification by FCC eluting with System A (1:1) gave the title product (413.3 mg), t.l.c. (System A 1:1) Rf 0.17, and an oil (2.546 g) t.l.c. (System A 1:1) Rf 0.66 which was dissolved in THF (20 ml). A mixture of tetrabutylammonium fluoride (1M in THF 16.6 ml) and acetic acid (998 mg) in THF (10 ml) was added at room temperature. After 30 mins. the reaction mixture was basified with saturated aqueous sodium hydrogen carbonate. Extraction with ethyl acetate (4×) gave, after drying, a brown gum (2.43 g). Purification by FCC eluting with System A (1:1) gave the title compound (1.396 g) as a brown solid. $[\alpha]_D^{20}$ (c 1.22, EtOAc) −18°. $\nu$max (CHBr$_3$) 3620 and 3530 (OH), 1742 (ester carbonyl) and 1712 cm$^{-1}$ (keto carbonyl). $\lambda$max (MeOH) 244.4 nm ($\epsilon$14,526).

INTERMEDIATE 18

Methyl (5S,E)-7-[4,5-bis(4-fluorophenyl)-2-(1-methylethyl)-1H-imidazol-1-yl]-5-hydroxy-3-oxo-6-heptenoate To a mixture of methyl [5S,1'R, (E)] 7-[4,5-bis(4-fluorophenyl)-2-(1-methylethyl)-1H-imidazol-1-yl]-5-(3-hydroxy-1-methylpropoxy)-3-oxo-6-heptenoate (50.6 mg) and sodium hydrogen carbonate (anhydrous, 381 mg) in dry dichloromethane (1.5 ml) under nitrogen at room temperature, powdered 1,1,1-tri(acetyloxy)-1,1-dihydro-1,2-benziodoxol-3(1H)-one (87 mg) was added. After stirring for 2 h, the mixture was diluted with ether (20 ml) and quenched with saturated aqueous sodium thiosulphate. The organic solution was separated and the aqueous solution was extracted with ether (3×). The combined ethereal solution was dried and evaporated to give a gum (54.3 mg). Filtration through silica gel using System A (1:1) as eluant afforded a yellow gum (37.6 mg). This crude product was dissolved in dry dichloromethane (1.5 ml) and cooled to 0° under nitrogen. Powdered dibenzylammonium trifluoroacetate (22 mg) was added and stirred for 90 mins. The mixture was diluted with water (20 ml) and ether (30 ml), the organic solution was separated, washed with water (3×30 ml) and then dried. Removal of solvent gave a light brown gum (43.6 mg).

Preparative t.l.c. (Whatman PK6F) eluting with System A (1:1) gave the title product (11.5 mg) as a light brown gum, t.l.c. (System A 1:1) Rf 0.22; $[\alpha]_D^{20}$ (c 1.13, EtOAc) −5.3°; (S:R=95:5 by chiral HPLC).

INTERMEDIATE 19

(a) 5-(4-Fluorophenyl)-2-(1-methylethyl)-4-(4-pyridinyl)-1H-imidazole, 1'-oxide To a stirred solution of 5-(4-fluorophenyl)-2-(1-methylethyl)-4-(4-pyridinyl)-1H-imidazole (0.28 g) in chloroform (2 ml) at 20°, m-chloroperbenzoic acid (50%;0.17 g) was added portionwise over 15 min. Stirring was continued at 20° for 3 h. The mixture was diluted with ether, washed with saturated aqueous sodium bicarbonate, dried and evaporated to dryness. The residue was purified by CC eluting with a mixture of chloroform and methanol (10:1) to give the title compound, (0.12 g)$\delta$(CDCl$_3$) 10.30(s,1H,NH), 7.92(d,2H, J8 Hz, C-2 and C-6 protons of pyridine), 7.46(d,2H,J8 Hz,C-3 and C-5 protons of pyridine), 7.40(dd,2H,J9 and 6 Hz,C-2 and C-6 protons of p-fluorophenyl), 7.10(t,2H,J9 Hz, C-3 and C-5 protons of p-fluorophenyl), 3.11(septet,1H,J7 Hz,C$\underline{H}$(CH$_3$)$_2$), 1.41(d,6H,J7 Hz, CH(C$\underline{H}_3$)$_2$).

(b) 5-(4-Fluorophenyl)-2-(1-methylethyl)-4-(3-pyridinyl)-1H-imidazole, 1'-oxide From 5-(4-fluorophenyl)-2-(1-methylethyl)-4-(3-pyridinyl)-1H-imidazole (2.8 g) by the process as described for the preparation of Intermediate 19a to give the title compound (1.2 g), $\delta$(CDCl$_3$) 10.51(s,1H,N$\underline{H}$), 8.22(s,1H,C-2 proton of pyridine), 7.95(m,1H,C-6 proton of pyridine), 7.50(m,1H,C-3 proton of pyridine), 7.12(m,2H,C-2 and C-6 protons of p-fluorophenyl), 6.98(t,2H,J9 Hz,C-3 and C-5 protons of p-fluorophenyl), 3.10(septet,1H,J7 Hz,C$\underline{H}$(CH$_3$)$_2$), 1.39(d,6H,J7 Hz,CH(C$\underline{H}_3$)$_2$).

INTERMEDIATE 20

(a) Methyl (E)-3-[5-(4-fluorophenyl)-2-(1methylethyl)-4-(4-pyridinyl) -1H-imidazol-1-yl]-2-propenoate, 1'-oxide, (A) and methyl (E)-3-[4-(4-fluorophenyl)-2-(1-methylethyl)-5-(4-pyridinyl)-1H-imidazol-1yl]-2-propenoate, 1'-oxide, (B)

To a suspension in dry THF (20 ml) of 5-(4-fluorophenyl)-2-(1-methylethyl)-4-(4-pyridinyl)-1H-imidazole, 1'-oxide (0.68 g) at −20° under nitrogen was added potassium bis(trimethylsilyl)amide (0.5M in toluene; 5.8 ml). After stirring at −20° for 0.5 h the solution was warmed to 0° before addition of methyl propiolate (2 ml). The mixture was allowed to warm to 20° and was kept for 2 h at this temperature before purifying by CC eluting with a mixture of ethyl acetate, petroleum ether (bp. 40°–60°) and methanol (5:5:1). From early fractions was obtained title compound (B) (0.12 g),$\delta$(CDCl$_3$), 8.25(d,2H,J6 Hz,C-2 and C-6 protons of pyridine), 7.81(d,1H,J15 Hz,NCH=CH), 7.00(t,2H,J9 Hz,C-3 and C-5 protons of p-fluorophenyl), 5.48(d,1H,J15 Hz,NCH=C$\underline{H}$), 3.75(s,3H,CO$_2$CH$_3$), 3.22(septet,1H,J7 Hz,C$\underline{H}$(CH$_3$)$_2$), 1.45(d,6H,J7 Hz,CH(C$\underline{H}_3$)$_2$, and from later fractions was obtained title compound (A) (0.30 g),$\delta$(CDCl$_3$), 8.02(d,2H,J6 Hz,C-2 and C-6 protons of pyridine), 7.74(d,1H,J15 Hz,NCH=CH), 5.32(d,1H,J15 Hz,NCH=C$\underline{H}$), 3.71(s,3$\underline{H}$,CO$_2$CH$_3$), 3.23(septet,1H,J7 Hz,C$\underline{H}$(CH$_3$)$_2$), 1.45(d,6H,J7 Hz,CH(C$\underline{H}_3$)$_2$).

(b) Methyl
(E)-3-[5-(4-fluorophenyl)-2-(1-methylethyl)-4-(3-pyridinyl)-1H-imidazol-1-yl]-2-propenoate, 1'-oxide. (A) and methyl (E)-3-[4-(4-fluorophenyl)-2-(1-methylethyl)-5-(3-pyridinyl)-1H-imidazol-1-yl]-2-propenoate, 1'-oxide, (B)

From 5-(4-fluorophenyl)-2-(1-methylethyl)-4-(3-pyridinyl)-1H-imidazole, 1'-oxide (0.8 g) by the process as described for the preparation of Intermediate 20a to give from early fractions the title compound (B) (0.2 g),$\delta(CDCl_3)$ 8.27(m,1H,C-6 proton of pyridine), 8.15(m,1H,C-2 proton of pyridine), 7.79(d,1H,J15 Hz,NC$\underline{H}$=CH), 6.98(t,2H,J9 Hz,C-3 and C-5 protons of 4-fluorophenyl), 5.42(d,1H,J15 Hz,NCH=C$\underline{H}$), 3.75(s,3H,CO$_2$CH$_3$), 3.22(septet,1H,J7 Hz,C$\underline{H}$(CH$_3$)$_2$), 1.46(d,6H,J7 Hz,CH(C$\underline{H}_3$)$_2$). Later fractions afforded title compound A (0.22 g),$\delta(CDCl_3)$ 8.45(m,1H,C-2 proton of pyridine), 8.02(m,1H,C-6 proton of pyridine), 7.73(d,1H,J15 Hz,NC$\underline{H}$=CH), 5.31(d,1H,J15 Hz,NCH=C$\underline{H}$), 3.73(s,3H, CO$_2$CH$_3$), 3.22(septet,1H,J7 Hz,C$\underline{H}$(CH$_3$)$_2$), 1.44(d,6H,J7 Hz,CH(C$\underline{H}_3$)$_2$).

INTERMEDIATE 21

(E)-3-[5-(4-Fluorophenyl)-2-(1-methylethyl)-4-(4-pyridinyl)-1H-imidazol-1-yl]-2-propenol A stirred suspension in toluene of methyl (E)-3-[5-(4-fluorophenyl)-2-(1-methylethyl)-4-(4-pyridinyl)-1H-imidazol-1-yl]-2-propenoate, 1'-oxide, (0.22 g), at $-78°$ under nitrogen was treated with diisobutylaluminium hydride (1.5M in toluene; 0.8 ml). The mixture was stirred at $-40°$ for 1 h and then allowed to warm to 0° before addition of water (1 ml) and ethyl acetate (20 ml). After stirring for 0.5 h the organic layer was separated, washed with brine, dried and evaporated to dryness. The residue was purified by CC eluting with a mixture of ethyl acetate, petroleum ether (bp. 40°-60°) and methanol (5:5:2) to give the title compound (0.05 g), $\delta(CDCl_3)$ 8.39(m,2H,C-2 and C-6 protons of pyridine), 6.60(d,1H,J15 Hz,NC$\underline{H}$=CH), 5.58(dd,1H,J15 and 6 Hz,NCH=C$\underline{H}$), 4.18(m,2H,CH$_2$OH), 3.17(septet,1H,J7 Hz,C$\underline{H}$(CH$_3$)$_2$), 1.42(d,6H,J7 Hz,CH(C$\underline{H}_3$)$_2$).

INTERMEDIATE 22

(E)-3-[5-(4-Fluorophenyl)-2-(1-methylethyl)-4-(3-pyridinyl)-1H-imidazol-1-yl]-2-propenol Methyl (E)-3-[5-(4-fluorophenyl)-2-(1-methylethyl)-4-(3-pyridinyl)-1H-imidazol-1-yl]-2-propenoate, 1'-oxide (0.18 g) in dichloromethane (3 ml) at 3° under nitrogen was treated with diisobutylaluminium hydride (1.5M in toluene; 0.94 ml). The mixture was stirred at 0° for 1 h and then quenched with water (1 ml) and extracted with ethyl acetate. The extracts were washed with brine, dried and evaporated. The residue was purified by CC eluting with a mixture of ethyl acetate, petroleum ether (bp. 40°-60°) and methanol (10:10:3) to give the title compound (0.05 g), $\delta(CDCl_3)$ 8.60(m,1H,C-2 proton of pyridine), 8.48(m,1H,C-6 proton of pyridine), 7.81(m,1H, C-3 proton of pyridine), 6.63(d,1H,J15 Hz,NC$\underline{H}$=CH), 5.56(dd,1H, J15 and 6 Hz,NCH=C$\underline{H}$), 4.18(m,2H,CH$_2$OH), 3.17(septet,1H,J7 Hz, C$\underline{H}$(CH$_3$)$_2$), 1.42(d,6H,J7 Hz,CH(C$\underline{H}_3$)$_2$).

INTERMEDIATE 23

(E) and (Z)-3-[4,5-Bis(3-chlorophenyl)-2-trifluoromethyl-1H-imidazol-1-yl]-2-propenoic acid, methyl ester To a slurry of sodium hydride (60% dispersion in oil, 0.145 g, washed with dry cyclohexane (3 × 5 ml)), in dry DMF (5 ml) at 3° under nitrogen was added 4,5-bis(3-chlorophenyl)-2-trifluoromethyl-1H-imidazole (0.998 g). After 10 min, 3-chloro-2-propenoic acid, methyl ester (80% in toluene, 2.044 g) in dry DMF (4 ml) was added and the resultant solution heated to 100° for 20 h. The reaction was allowed to cool to room temperature, quenched with saturated aqueous ammonium chloride solution (10 ml) and extracted with ether (3 × 30 ml). The combined extracts were dried and evaporated to yield a light brown solid (1.43 g) which was purified by CC eluting with System A (3:17) to give (E)-3-[4,5-bis(3-chlorophenyl)-2-trifluoromethyl-1H-imidazol-1-yl]-2-propenoic acid, methyl ester, Rf 0.38 (System A 3:17); $\delta(CDCl_3)$ values include 3.75 (s, CO$_2$Me), 5.66 (d, J 15 Hz, NCH=C$\underline{H}$), 7.73 (d, J 15 Hz, NC$\underline{H}$=CH), and (Z)-3-[4,5-bis(3-chlorophenyl)-2-trifluoromethyl-1H-imidazol-1-yl]-2-propenoic acid, methyl ester, Rf 0.32 (System A 3:17); $\delta(CDCl_3)$ values include 3.61 (s, CO$_2$Me), 6.13 (d, J 7 Hz, NCH=C$\underline{H}$), 6.89 (d, J 7 Hz, NC$\underline{H}$=CH), as a 2:1 mixture (1.041 g) as a pale yellow solid.

INTERMEDIATE 24

(±)-(E)-1-[4,5-Bis(4-fluorophenyl)-2-(1-methylethyl)-1H-imidazol-1-yl]-1,5-hexadien-3-ol To a solution of (E)-3-[4,5-bis(4-fluorophenyl)-2-(1-methylethyl)-1H-imidazol-1-yl]-2-propenal (430 mg) in dry THF (7 ml) at 0° under nitrogen, allylmagnesium chloride (2M in THF, 0.86 ml) was added. The mixture was stirred for 2.5 h at 0° and then quenched with saturated aqueous ammonium chloride. Extraction with ether (4×) gave, after drying and rotary-evaporation, the crude product (466 mg). FCC eluting with 20% then 30% System A afforded the title product (331.9 mg) as a white solid. Rf 0.41 (System A 1:1); $\nu_{max}$ (CHBr$_3$) 3587cm$^{-1}$(OH).

INTERMEDIATE 25

(±)-Erythro/Threo-(E)-1-(3-Bromo-4,5-dihydro-5-isoxazolyl)-4-[4,5-bis-(4-fluorophenyl)-2-(1-methylethyl)-1H-imidazol-1-yl]-3-buten-2-ol To a mixture of (±)-(E)-1-[4,5-bis(4-fluorophenyl)-2-(1-methylethyl)-1H-imidazol-1-yl]-1,5-hexadien-3-ol (187.3 mg) and sodium hydrogen carbonate (440 mg) in ethyl acetate (10 ml) containing water (0.5 ml) under nitrogen at room temperature, dibromoformaldoxime (145 mg) was added. The reaction was stirred at room temperature for 23 h. The organic solution was seperated and rotary-evaporated to give a yellow foam (308 mg). FCC eluting sequentially with 30%, 40% and then 60% System A afforded the title compounds (208 mg), as a yellow solid in a diastereomeric ratio of 1:1. Rf 0.25 (System A 1:1); $\nu_{max}$ (CHBr$_3$) 3587(OH), 1667cm$^{-1}$ (imidazole I band).

INTERMEDIATE 26

(±)-Erythro/threo-(E)-1-[4,5-bis(4-fluorophenyl)-2-(methylethyl)-1H-imidazol-1-yl]-4-(4,5-dihydro-3-methoxy-5-isoxazolyl)-1-buten-3-ol A mixture of (±)-erythro/threo-(E)-1-(3-bromo-4,5-dihydro-5-isoxazolyl)-4-[4,5-bis(4-fluorophenyl)-2-(1-methylethyl)-1H-imidazol-1-yl]-3-buten-2-ol (51.6 mg) and lithium methoxide (24 mg) in methanol (2 ml) was heated under reflux for 2.5 h. The reaction was quenched with water (20 ml), extracted with ether (4×), and dried before removal of solvent to give a white solid (44.3 mg). Preparative t.l.c. eluting with System A (1:1) afforded a 1:1 diastereomeric mixture of the title compounds (41.2 mg) as a clear gum which became a white solid on standing at room temperature, Rf 0.16 (System A 1:1).

INTERMEDIATE 27

(±)-(E)-1-[4,5-Bis(4-fluorophenyl)-2-(1-methylethyl)-1H-imidazol-1-yl]-3-hydroxy-1-hexen-5-one To a solution of lithium bis(trimethylsilyl)amide (4.1 ml, 1M solution in THF) in dry THF (20 ml) at $-78°$ under nitrogen was added dry acetone (275 μl). After 25 min, a solution of (E)-3-[4,5-bis(4-fluorophenyl)-2-(1-methylethyl)-1H-imidazol-1-yl]-2-propenal (881 mg) in dry THF (15 ml) was added dropwise over 10 min. Stirring was continued for 25 min at $-78°$ then the reaction was quenched with saturated aqueous ammonium chloride solution (25 ml) and allowed to warm to room temperature. The layers were separated and the aqueous phase extracted with ethyl acetate (2×50 ml). The combined extracts were dried and evaporated to a white solid (1.09 g). FCC eluting with System A (1:1) gave the title compounds as a white solid (709.6 mg). (CDCl$_3$) 7.35–7.45 and 7.20–7.29(2m,4H,C-2 and C-6 protons of 4-fluorophenyl), 7.10 and 6.90(2t,4H,C-3 and C-5 protons of 4-fluorophenyl,J=9 Hz), 6.70(d,1H,NCH=CHCH,J=13.7 Hz), 5.26(dd,1H,NCH=CHCH,J=13.7 Hz,6.3 Hz), 4.58(m,1H,NCH=CHCH), 3.15(m,2H,CH(CH$_3$)$_2$ and OH), 2.50(m,2H,CH(OH)CH$_2$C(O)), 2.15(s,3H,CH$_2$C(O)CH$_3$), 1.40(d,6H,CH(CH$_3$)$_2$,J=7.5 Hz).

EXAMPLE 1

Methyl (±)-erythro-(E)-3,5-dihydroxy-7-[5-(4-fluorophenyl)-2-(1-methylethyl)-4-phenyl-1H-imidazol-1-yl]-6-heptenoate and methyl (±)-erythro-(E)-3,5-dihydroxy-7-[4-(4-fluorophenyl)-2-(1-methylethyl)-5-phenyl-1H-imidazol-1-yl]-6-heptenoate To a solution of triethylborane (1M in THF, 0.14 ml) in THF (0.7 ml) at room temperature under nitrogen was added dry methanol (0.26 ml), and the resulting mixture was stirred for 1 h at room temperature and then cooled to $-78°$. Methyl(±)-(E)-7-[5(4)-(4-fluorophenyl)-2-(1-methylethyl)-4(5)-phenyl-1H-imidazol-1-yl]-5-hydroxy-3-oxo-6-heptenoate (0.050 g) in THF (6 ml) was added and the mixture was stirred for 1 h. Sodium borohydride (0.005 g) was added and after 5 h of stirring at $-78°$ the reaction was quenched with saturated aqueous ammonium chloride (5 ml) and the resultant mixture was allowed to warm to room temperature overnight. The mixture was diluted with water (20 ml) and extracted with ethyl acetate (5×20 ml). The extracts were dried and evaporated to give a colourless film which was azeotroped four times from methanol (30 ml), to give the title compounds (0.058 g) as a colourless film, Rf (System A 2:1) 0.32; δ(CDCl$_3$), 1.3–1.6 (m, CH(OH)CH$_2$CH(OH)), 1.38 (d, J=7 Hz, (CH$_3$)$_2$CH), 2.37–2.47 (m, CH$_2$CO$_2$CH$_3$), 3.13 (septet, J=7 Hz, (CH$_3$)$_2$CH), 3.71 (s, CH$_2$CO$_2$CH$_3$), 4.03–4.20 (m, CH$_2$CH(OH)CH$_2$CO$_2$CH$_3$), 4.30–4.43 (m, CH=CHCH), 5.23–5.36 (m, CH=CHCH), 6.62 (d, J=14 Hz, CH=CHCH), 6.88, 7.06 and 7.11–7.46 (2t, J=9 Hz, and m, aromatic protons).

EXAMPLE 2

Sodium (±)-erythro-(E)-3,5-dihydroxy-7-[5-(4-fluorophenyl)-2-(1-methylethyl)-4-phenyl-1H-imidazol-1-yl]-6-heptenoate and sodium (±)-erythro-(E)-3,5-dihydroxy-7-[4-(4-fluorophenyl)-2-(1-methylethyl)-5-phenyl-1H-imidazol-1-yl]-6-heptenoate To a stirred solution of methyl (±)-erythro-(E)-3,5-dihydroxy-7-[5(4)-(4-fluorophenyl)-2-(1-methylethyl)-4(5)-phenyl-1H-imidazol-1-yl]-6-heptenoate (0.0137 g) in THF (1 ml) under nitrogen was added aqueous sodium hydroxide (0.1M, 0.29 ml). After 0.5 h the mixture was diluted with water (20 ml) and the resultant solution was extracted with ether (20 ml×2). The aqueous phase was filtered and then freeze dried to give the title compounds (0.014 g) as a brown solid, δ(D$_2$O) 1.2–1.8 (m, CH(OH)CH$_2$CH(OH)), 1.35 (d, J=7 Hz, (CH$_3$)$_2$CH), 2.17–2.30 (m, CH$_2$CO$_2$Na), 3.27 (septet, J=7 Hz, (CH$_3$)$_2$CH), 3.49–3.75 (m, CHCH$_2$CO$_2$Na), 4.26–4.41 (m, CH=CHCH), 5.43–5.58 (m, CH=CHCH), 6.74 (d, J=14 Hz, CH=CHCH), 6.98, 7.14 and 7.16–7.47 (2t, J=9 Hz, and m, aromatic protons).

EXAMPLE 3

Methyl (±)-erythro-(E)-7-[4,5-bis(4-fluorophenyl)-2-(1-methylethyl)-1H-imidazol-1-yl]-3,5-dihydroxy-6-heptenoate.

To a solution of triethylborane (1M in THF, 0.36 ml) in THF (1.7 ml) at room temperature under nitrogen, methanol (dried, 0.35 ml) was added and stirred for 1 h. The solution was then cooled to $-78°$ and methyl (±)-(E)-7-[4,5-bis(4-fluorophenyl)-2-(1-methylethyl)-1H-imidazol-1-yl]-5-hydroxy-3-oxo-6-heptenoate (0.052 g) in THF (4 ml) was added. The mixture was stirred for 1 h after which time sodium borohydride (0.005 g) was added. After 6 h of stirring at $-78°$, the reaction was diluted with ethyl acetate (10 ml) and quenched with saturated aqueous ammonium chloride solution (10 ml) at $-78°$. The mixture was allowed to warm to room temperature overnight, then extracted with ethyl acetate (5×20 ml) and dried. Rotary-evaporation gave a residue which was azeotroped with methanol (4×30 ml) to give the crude product as an orange film. Purification by FCC eluting with System A (2:1) gave the title compound (0.046 g) as a clear colourless film, Rf (System A 2:1) 0.20; δ(CDCl$_3$) 1.3–1.8 (m, CH(OH)CH$_2$CH(OH)), 1.40 (d, J=7 Hz, (CH$_3$)$_2$CH), 2.44 (d, J=5 Hz, CH$_2$CO$_2$Me), 3.13 (septet, J=7 Hz, (CH$_3$)$_2$CH), 3.73 (s, CO$_2$Me), 3.8–4.0 (bs, CH(OH)CH$_2$CH(OH)), 4.10–4.21 (m, CH(OH)CH$_2$CO$_2$Me), 4.37–4.46 (m, CH=CHCH(OH)), 5.31 (dd, J=15 and 5 Hz, NCH=CHCH(OH)), 6.66 (dd, J=15 and 2 Hz, NCH=CHCH(OH)), 6.90 and 7.09 (2t, J=9 Hz, C-3 and C-5 protons of 4-fluorophenyls), 7.03-7.12 and 7.35-7.44 (2 m, C-2 and C-6 protons of 4-fluorophenyls).

EXAMPLE 4

Sodium (±)-erythro-(E)-7-[4,5-bis(4-fluorophenyl)-2-(1-methylethyl)-1H-imidazol-1-yl]-3,5-dihydroxy-6-heptenoate To a stirred solution of methyl (±)-erythro-(E)-3,5-dihydroxy-7-[4,5-bis(4-fluorophenyl)-2-(1-methylethyl)-1H-imidazol-1-yl]-6-heptenoate (0.044 g) in THF (0.5 ml) under nitrogen was added aqueous sodium hydroxide (0.1M, 0.84 ml). After 0.6 h the solution was rotary-evaporated to remove all organic solvent. The residual aqueous solution was diluted with water (10 ml) and extracted with ether (4×20 ml). The aqueous phase was filtered, concentrated (ca. 5 ml) and subjected to freeze-drying overnight to give the title compound as a beige solid (0.037 g), $\lambda_{max}$ (pH6 buffer) 249.8 nm ($\epsilon$11,950); $\delta$(DMSO-d$_6$) 1.0-1.50 (m, CH(OH)CH$_2$CH(OH)), 1.30 (d, J=7 Hz, (CH$_3$)$_2$CH), 1.70-1.82 and 1.94-2.03 (2m, CH$_2$CO$_2$Na), 3.16 (septet, J=7 Hz, (CH$_3$)$_2$CH), 3.47-3.60 (m, CH(OH)CH$_2$CO$_2$Na), 4.13-4.23 (m, CH=CHCH(OH)), 5.15-5.28 (bs, OH), 5.48 (dd, J=15 and 5 Hz, NCH=CHCH(OH)), 6.55 (d, J=15 Hz, NCH=CH(OH)), 7.06 and 7.22-7.42 (t, J=9 Hz and m, aromatic protons).

EXAMPLE 5

1,1-Dimethyleth-1-yl (3R,5S,E)-7-[4,5-bis(4-fluorophenyl)-2-(1-methylethyl)-1H-imidazol-1-yl]-3,5-dihydroxy-6-heptenoate A solution of dry THF (16 ml) and dry methanol (4 ml) under nitrogen at room temperature was treated with a solution of triethyl borane (1.0M in THF, 2.32 ml). After 1 h the mixture was cooled to −78° and treated with a solution of 1,1-dimethyleth-1-yl (5S,E)-7-[4,5-bis-(4-fluorophenyl)-2-(1-methylethyl)-1H-imidazol-1-yl]-5-hydroxy-3-oxo-6-heptenoate (1.075 g) in THF (4:1) (15 ml) plus washings (5 ml). After a further 1 h at −75° the mixture was treated with sodium borohydride (88 mg). After 2½ h the mixture was quenched with saturated aqueous ammonium chloride solution (2 ml) and allowed to warm. The mixture was then diluted with water (100 ml) and extracted with ethyl acetate (3×70 ml). The combined extracts were dried and evaporated and the residue was azeotroped with methanol (3×30 ml). This gave a pale yellow solid (1.076 g) which was crystallised from ether-cyclohexane to give the title compound (739 mg) as white fluffy crystals, $\delta$(CDCl$_3$) 1.3-1.65 (m, 2H, CH(OH)CH$_2$CH(OH)), 1.40 (d, J7 Hz, 6H, —CH(CH$_3$)$_2$), 1.46 (s, 9H, —C(CH$_3$)$_3$), 2.35 (d, J7 Hz, 2H, CH$_2$CO$_2$R), 3.15 (septet, J7 Hz, 1H, —CH(CH$_3$)$_2$), 3.77, 3.81 (2s, 2H, CH(OH)CH$_2$CH(OH), 4.12 (m, 1H, CH(OH)CH$_2$CO$_2$), 4.42 (m, 1H, =CHCH(OH)CH$_2$—), 5.30 (dd, J14 and 7 Hz, 1H, N—CH=CH—), 6.67 (d, J14 Hz, 1H, N—CH=CH—), 6.90 and 7.09 (2t, J9 Hz each 2H, C-3 and C-5 protons of 4-fluorophenyls), 7.2-7.43 (m, 4H, C-2 and C-6 protons of 4-fluorophenyls).

EXAMPLE 6

Sodium (3R,5S,E)-7-[4,5-bis(4-fluorophenyl)-2-(1-methylethyl)-1H-imidazol-1-yl]-3,5-dihydroxy-6-heptenoate A solution of 1,1-dimethyleth-1-yl (3R,5S,E)-7-[4,5-bis(4-fluorophenyl)-2-(1-methylethyl)-1H-imidazol-1-yl]-3,5-dihydroxy-6-heptenoate (51 mg) in ethanol (5 ml) was treated with aqueous sodium hydroxide solution (0.1M, 1 ml) and the clear solution was stirred at room temperature. After 18 h the solution was concentrated to ca 1 ml and then diluted with water (20 ml) and the solution washed with ether (2×7 ml). The solution was briefly evaporated and then freeze dried to give the title compound (52 mg), as a white fluffy solid, $[\alpha]_D^{20}$+19.5° (c 0.41, H$_2$O); $\delta$(D$_2$O) 1.20-1.55, 1.55-1.82 (m, 2H, CH(OH)CH$_2$CH(OH)), 1.34 (d, J 7 Hz, 6H, CH(CH$_3$)$_2$), 2.26 (d, J 7 Hz, 2H, CH$_2$CO$_2$Na), 3.28 (septet, J 7 Hz, 1H, —CH(CH$_3$)$_2$), 3.67 (m, 1H, =CHCH(OH)CH$_2$CH(OH)), 4.35 (m, 1H, CH=CHCH(OH)), 5.61 (dd, J 14 and 7 Hz, 1H, NCH=CH), 6.75 (d, J 14 Hz, 1H, NCH=CH), 7.01 (t, J 9 Hz, 2H, C-3 and C-5 protons of 4-fluorophenyl), 6.91-7.41 (m, 6H, aromatics).

(RS:SR=93:7 as determined by chiral HPLC).

EXAMPLE 7

Methyl (3R,5S,E)-7-[4,5-bis(4-fluorophenyl)-2-(1-methylethyl)-1H-imidazol-1-yl]-3,5-dihydroxy-6-heptenoate A mixture of dry THF (4 ml) and dry methanol (1 ml) under nitrogen at room temperature was treated with a solution of triethylborane (1.0M in THF, 0.6 ml). After 1 h, the mixture was cooled to −78°, and a portion of this diethyl methoxyborane solution (1.93 ml) was added to methyl (5S,E)-7-[4,5-bis(4-fluorophenyl)-2-(1-methylethyl)-1H-imidazol-1-yl]-5-hydroxy-3-oxo-6-heptenoate (73.8 mg) under magnetic stirring. The homogeneous solution was stirred for 1 h, then treated with powdered sodium borohydride (98%, 6.4 mg) at −78°. After 4.5 h, the reaction mixture was diluted with ethyl acetate, quenched with saturated aqueous ammonium chloride solution and allowed to warm to room temperature overnight. The organic solution was separated and the aqueous solution washed with ether (3×). The combined organic solutions were dried and evaporated. The residue was azeotroped with methanol (3×) to give a brown gum. This gum was subjected to preparative t.l.c. eluting with System A (3:2), to give the title compound (36.1 mg) as a brown gum, $[\alpha]_D^{20}$+5.38° (c 1.86, ethyl acetate), $\delta$(CDCl$_3$) 1.40 (d, J 7 Hz, 6H, —CH(CH$_3$)$_2$), 1.4-1.8 (m, 2H, CH(OH)CH$_2$CH(OH)), 2.44 (d, J 5 Hz, 2H, CH$_2$CO$_2$CH$_3$), 3.13 (septet, J 7 Hz, 1H, —CH(CH$_3$)$_2$), 3.73 (s, 3H, OCH$_3$), 3.85 (broad s, 2H, CH(OH)CH$_2$CH(OH)), 4.15 (m, 1H, CH(OH)CH$_2$CO$_2$CH$_3$), 4.42 (m, 1H, =CHCH(OH)CH$_2$), 5.31 (dd, J 15 and 5 Hz, 1H, NCH=CH—), 6.66 (dd, J 15 and 2 Hz, 1H, NCH=CH—), 6.90 (t, J 9 Hz, 2H, C-3 and C-5 protons of 4-(4-fluorophenyl)), 7.09 (t, J 9 Hz, 2H, C-3 and C-5 protons of 5-(4-fluorophenyl)), 7.23 and 7.39 (2 dd, J 9 and 6 Hz, 4H, C-2 and C-6 protons of 4-fluorophenyls).

EXAMPLE 8

Sodium (3R,5S,E)-7-[4,5-bis(4-fluorophenyl)-2-(1-methylethyl)-1H-imidazol-1-yl]-3,5-dihydroxy-6-heptenoate A solution of methyl (3R,5S,E)-7-[4,5-bis(4-fluorophenyl)-2-(1-methylethyl)-1H-imidazol-1-yl]-3,5-dihydroxy-6-heptenoate (34.4 mg) in dry THF (2 ml) was treated with aqueous sodium hydroxide solution (0.1M 0.660 ml). After 5 minutes, the solution was concentrated and the aqueous residue was diluted with water (9 ml) and the solution washed with ethyl acetate (4×). The solution was briefly evaporated and then freeze-dried to give the title compound (29.2 mg) as a white fluffy solid, $[\alpha]^{20} + 16.7°$ (c 0.4, $H_2O$); $\delta(D_2O)$ 1.20–1.55, 1.55–1.85 (m, 2H, $CH(OH)CH_2CH(OH)$), 1.34 (d, J 7 Hz, 6H, $CH(CH_3)_2$), 2.26 (d, J 7 Hz, 2H, $CH_2CO_2Na$), 3.30 (septet, J 7 Hz, 1H, $CH(CH_3)_2$), 3.67 (m, 1H, =CHCH(OH)CH$_2$CH(OH)), 4.35 (m, 1H, CH=CHCH(OH)), 5.61 (dd, J 14 and 7 Hz, 1H, NCH=CH), 6.75 (d, J 14 Hz, 1H, NCH=CH), 7.01 (t, J 9 Hz, 2H, C-3 and C-5 protons of 4-(4-fluorophenyl)), 7.1–7.4 (m, 6H, aromatics).

EXAMPLE 9

(±)-erythro-(E)-7-[4,5-bis(4-fluorophenyl)-2-(1-methylethyl)-1H-imidazol-1-yl]-3,5-dihydroxy-6-heptenoic acid To a stirred solution of impure methyl (±)-erythro-(E)-7-[4,5-bis(4-fluorophenyl)-2-(1-methylethyl)-1H-imidazol-1-yl]-3,5-dihydroxy-6-heptenoate (3.10 g) in dry THF (180 ml) was added aqueous sodium hydroxide (0.1M, 66 ml). The resultant solution was stirred for 0.5 h at room temperature and then concentrated to ca ⅓ volume. This solution was diluted with water (300 ml) and then adjusted to pH4 with hydrochloric acid (2M). Ammonium sulphate was added and the resultant murky solution was extracted with ethyl acetate (7×100 ml). The extracts were combined, dried and evaporated to give the title product (3.13 g) as a yellow solid. $\lambda_{max}$ ($CH_3CN$) 273.0 nm ($\epsilon$11,595); $\delta(CDCl_3)$ 1.42(d,J7 Hz, 6H,$(CH_3)_2CH$), 2.51(d,J6 Hz,2H,$CH_2CO_2H$), 3.16(septet,J7 Hz,1H,$(CH_3)_2CH$), 4.05–4.26(m,1H,$CH(OH)CH_2CO_2Me$), 4.40–4.51(m,1H,CH=CHCH(OH)), 5.32(dd,J15 and 5 Hz,1H,NCH=CHCH(OH)), 6.68(dd,J15 and 2 Hz,1H,NCH=CHCH(OH)), 6.90 and 7.09(2t,J9 Hz, each 2H, C-3 and C-5 protons of 4-fluorophenyls), 7.18–7.32 and 7.32–7.45(2m, each 2H, C-2 and C-6 protons of 4-fluorophenyls).

EXAMPLE 10

Trans-(E)-6-[2-[4,5-bis(4-fluorophenyl)-2-(1-methylethyl)-1H-imidazol-1-yl]-ethenyl]-4-hydroxy-tetrahydro-2H-pyran-2-one A stirred suspension of impure (±)-erythro-(E)-7-[4,5-bis(4-fluorophenyl)-2-(1-methylethyl)-1H-imidazol-1-yl]-3,5-dihydroxy-6-heptenoic acid (3.13 g) in dry dichloromethane (130 ml) was treated with 1-cyclohexyl-3-(2-morpholinoethyl)carbodiimide metho-p-toluenesulphonate (5.59 g). After 20 h the reaction mixture was poured onto saturated brine (200 ml) and the aqueous phase was separated off and extracted with dichloromethane (2×100 ml). The organic phases were combined, dried and evaporated to give crude product as a brown foam. Purification by FCC eluting with System A (2:1) gave the title product (1.49 g) as an off white crystalline solid; $\lambda_{max}$ ($CH_3CN$) 274.4 nm ($\epsilon$13, 373); $\delta(CDCl_3)$ 1.59(m,2H,$CHCH_2CH(OH)$), 1.41(d,J7 Hz,2H,$CH(CH_3)_2$), 2.08(bs,1H,OH), 2.56–2.78(m,2H,$CH_2C(=O)$), 3.13(septet,J7 Hz,1H,$CH(CH_3)_2$), 4.33(m,1H,$CH_2CH(OH)$), 5.13–5.28(m,1H,$OCHCH_2$), 5.27(dd,J14 and 7 Hz,1H,CH=CHN), 6.75(d,J14 Hz,1H,CH=CHN), 6.90 and 7.11(2t,J9 Hz, each 2H, C-3 and C-5 protons of 4-fluorophenyls), 7.18–7.45(m,4H, C-2 and C-6 protons of 4-fluorophenyls).

EXAMPLE 11

(4R,6S,E)-6-[2-[4,5-Bis(4-fluorophenyl)-2-(1-methylethyl)-1H-imidazol-1-yl]-ethenyl]-4-hydroxy-tetrahydro-2H-pyran-2-one A solution of 1,1-dimethyleth-1-yl (3R,5S,E)-7-[4,5-bis(4-fluorophenyl)-2-(1-methylethyl)-1H-imidazol-1-yl]-3,5-dihydroxy-6-heptenoate (25.6 mg) in redistilled THF (1.4 ml) was treated with aqueous sodium hydroxide solution (0.1M, 0.5 ml) and the clear colourless solution was stirred at room temperature. After 3.5 h the reaction mixture was concentrated to ca 0.5 ml. The residue was diluted with water (3 ml), acidified to pH4 with hydrochloric acid (2M), ammonium sulphate added and then extracted with ethyl acetate (4×3 ml). The combined extracts were dried and evaporated to a white gummy solid (25 mg). This was dissolved in dry dichloromethane (1.4 ml) and then treated with 1-cyclohexyl-3-(2-morpholinoethyl)carbodiimide metho-p-toluenesulphonate (42.4 mg). The resulting solution was stirred at room temperature. After 18.5 h the reaction mixture was diluted with water (5 ml) and then extracted with dichloromethane (3×5 ml). The combined extracts were washed with brine (5 ml), dried and evaporated to a cream solid (23 mg). The solid was filtered through a short colum of 70–230 mesh silica developing and eluting with System A (3:1) to give the title compound as a cream solid (18 mg), $\nu_{max}$ (CHBr$_3$) 1735cm$^{-1}$ (lactone), $\delta(CDCl_3)$ values as for those described for the racemate obtained in Example 10.

EXAMPLE 12

Methyl (±)-erythro-(E)-3,5-dihydroxy-7-[5-(4-fluorophenyl)-2-(1-methylethyl)-4-(3-pyridinyl)-1H-imidazol-1-yl]-6-heptenoate,1'-oxide Methyl (±)-erythro-(E)-3,5-dihydroxy-7-[5-(4-fluorophenyl)-2-(1-methylethyl)-4-(3-pyridinyl)-1H-imidazol-1-yl]-6-heptenoate (4 mg) in chloroform (0.1 ml) was treated at 3° with m-chloroperbenzoic acid (50%; 3 mg). The mixture was allowed to warm to 20° and was stirred for 2 h at this temperature. It was then subjected to CC eluting with a mixture of ethyl acetate, petroleum ether (b.p. 40°–60° ) and methanol (5:5:2) to give the title compound (2.5 mg). $\delta(CDCl_3)$ 8.40 (s,1H,C-2 proton of pyridine), 7.99 (d, 1H, J 6 Hz, C-6 proton of pyridine), 6.64 (d, 1H, J 15 Hz, NCH=CH), 5.35 (dd, 1H, J 15 and 6 Hz, NCH=CH), 4.53 (m, 1H, =CHCHOH), 4.16 (m, 1H, $CH$ $OHCH_2CO_2Me$), 3.12 (septet, 1H, $CH(CH_3)_2$), 2.45 (m, 2H, $CH_2CO_2Me$), 1.38 (d, 6H, J 7 Hz, $CH(CH_3)_2$).

EXAMPLE 13

(3R,5S,E)-7-[4,5-Bis(4-fluorophenyl)-2-(1-methylethyl)-1H-imidazol-1-yl]-3,5-dihydroxy-6-heptenoic acid A solution of 1,1-dimethyleth-1-yl (3R,5S,E)-7-[4,5-bis(4-fluorophenyl)-2-(1-methylethyl)-1H-imidazol-1-yl]-3,5-dihydroxy-6-heptenoate (726 mg) in redistilled THF (40 ml) was treated with 0.1M aqueous sodium hydroxide solution (14.5 ml). After ½ h the mixture was concentrated to ca. 10 ml and then diluted with water (50 ml). The mixture was acidified to pH2 with 2N-hydrochloric acid, brought back to pH4 with aqueous sodium hydrogen carbonate solution, ammonium sulphate added and then the mixture was extracted with ethyl acetate (3×50 ml). The combined extracts were dried and concentrated to ca. 4 ml when a solid crystallised. The crystals were collected and dried to give the title compound (500 mg), m.p. 172°–3° C., $[\alpha]_D$ +15.7° (c 1.02, DMSO), (RS:SR=99.5:0.5).

EXAMPLE 14

Sodium (3R,5S,E)-7-[4,5-bis-(4-fluorophenyl)-2-(1-methylethyl)-1H-imidazol-1-yl]-3,5-dihydroxy-6-heptenoate A suspension of (3R,5S,E)-7-[4,5-bis-(4-fluorophenyl)-2-(1-methylethyl)-1H-imidazol-1-yl]-3,5-dihydroxy-6-heptenoic acid (200 mg) in sodium hydrogen carbonate (36.8 mg) and water (80 ml) was stirred at room temperature. After 19 h ethanol (20 ml) was added and the resulting clear solution stirred at room temperature. After 15 min the mixture was evaporated to dryness, the residue was dissolved in water (50 ml), filtered and then freeze dried to give the title compound (219 mg) as a white fluffy solid. $[\alpha]_D$ +22.6° (C 0.53, H$_2$O), δ(D$_2$O) 1.20–1.55, 1.55–1.78 (m, 2H, CH(OH)CH$_2$CH(OH)), 1.33 (d, J 7 Hz, 6H, CH(CH$_3$)$_2$), 2.26 (d, J $\overline{7}$ Hz, 2H, CH$_2$CO$_2$Na), 3.28 (septet, J $\overline{7}$ Hz, 1H, —C$\underline{H}$(CH$_3$)$_2$), 3.67 (m, 1H, =CHCH(OH)CH$_2$C-H(OH)), 4.35 (m, 1H, CH=CHCH(OH)), 5.49 (dd, J 14 $\overline{H}$z and 7 Hz, 1H, NCH=C$\underline{H}$), 6.72 (d, J 14 Hz, 1H, NC$\underline{H}$=CH), 6.97 (t, 9 Hz, 2$\overline{H}$, C-3 and C-5 protons of 4-fluorophenyl), 6.90–7.40 (m, 6H, aromatics).

EXAMPLE 15

Methyl (±)-erythro/threo-(E)-7-[4,5-bis(4-fluorophenyl)-2-(1-methylethyl)-1H-imidazol-1-yl]-3,5-dihydroxy-6-heptenoate (±)-Erythro/threo-(E)-1-[4,5-bis(4-fluorophenyl)-2-(1-methyethyl)-1H-imidazol-1-yl]-4-(4,5-dihydro-3-methoxy-5-isoxazolyl)-1-buten-3-ol (37.7 mg) in methanol-water (5:1, 2 ml) was added to a mixture containing Raney nickel (50% slurry in water, 304 mg) acetic acid (1 drop) and boric acid (25 mg) in methanol-water (5:1, 2 ml). The mixture was stirred at room temperature under hydrogen atmosphere for 2 h, then diluted with water (20 ml), extracted with ether (4×10 ml), dried and filtered. Removal of solvent gave a residue (36 mg). Preparative t.l.c. eluting twice with System A (60%) afforded the title compounds (12.6 mg) as a clear gum in the diastereomeric ratio of 3:2. Rf 0.25 (System A 70%); $v_{max}$ (CHBr$_3$) 3587 and 3490(OH), 1719 (CO$_2$CH$_3$), 1224 cm$^{-1}$ (C-F).

EXAMPLE 16

(3R,5S,(E))-7-[4,5-Bis(4-fluorophenyl)-2-(1-methylethyl)-1H-imidazol-1-yl]-3,5-dihydroxy-6-heptenoic acid, (1R)-7,7-dimethyl-2-oxobicyclo[2.2.1]heptane-1-methane sulphonic acid salt To a solution of (±)-erythro-(E)-7-[4,5-bis(4-fluorophenyl)-2-(1-methylethyl)-1H-imidazol-1-yl]-3,5-dihydroxy-6-heptenoic acid (2.5 g) in hot acetontrile (500 ml) was added (1R)-7,7-dimethyl-2-oxobicyclo[2.2.1-]heptane-1-methane sulphonic acid (636 mg). The solution was filtered and the filtrate was allowed to stand at 21° in the presence of a few crystals of the title salt for three days. After a further day at 2° the brown crystals were filtered off and ground in a pestle and mortar prior to drying to give the title salt (1.11 g) as a light brown solid containing ca 17% of the corresponding salt of the (3S,5R)-acid by chiral hplc analysis. $v_{max}$ (Nujol) 1750 and 1725 (C=O), 845 cm$^{-1}$ (aromatic CH); δ(d$_6$-DMSO) values include 0.76 (s,CH$_3$), 1.08 (s,CH$_3$), 1.46 (d,J 8 Hz, (CH$_3$)$_2$CH), 3.48 (septet, J 6 Hz, (CH$_3$)$_2$CH), 3.80 (m,C$\underline{H}$(OH)CH$_2$CO$_2$H), 4.20 (m,C$\underline{H}$=CHCH(OH)), 6.10 (dd,J 6 and 14 Hz, NCH=C$\underline{H}$), 6.66 (d,J 14 Hz, NC$\underline{H}$=CH), 7.2–7.6 (m,aromatic protons).

EXAMPLE 17

(±)-Cis & trans-(E)-6-[2-[4,5-bis(4-fluorophenyl)-2-(1-methylethyl)-1H-imidazol-1-yl]ethenyl]-4-hydroxy-tetrahydro-2H-pyran-2-one To a stirred solution of (±)-erythro-(E)-7-[4,5-bis(4-fluorophenyl)-2-(1-methylethyl)-1H-imidazol-1-yl]-3,5-dihydroxy-6-heptenoic acid, methyl ester containing ca 10% of (±)-threo-(E)-7-[4,5-bis(4-fluorophenyl)-2-(1-methylethyl)-1H-imidazol-1-yl]-3,5-dihydroxy-6-heptenoic acid, methyl ester (0.50 g) in distilled THF (90 ml) was added 0.1N aqueous sodium hydroxide (10.60 ml). After 0.5 h the mixture was evaporated to dryness and the residue was dissolved in water (100 ml). The resultant solution was adjusted to pH4 with 2N-hydrochloric acid when a pale yellow precipitate formed which was extracted into ethyl acetate (4×100 ml). The extracts were combined, dried and evaporated to give a pale yellow foam. Dichloromethane (100 ml) followed by 1-cyclohexyl-3-(2-morpholinoethyl)carbodiimide metho-p-toluenesulphonate (0.63 g) was added with stirring. After 3.5 h the mixture was poured onto saturated brine (100 ml) and the layers were shaken. The aqueous phase was separated off and extracted with dichloromethane (100 ml). The organic phases were combined, dried and evaporated to give a yellow foam which was purified by CC eluting with System A (2:1). Early fractions were combined and evaporated to give (±)-trans-(E)-6-[2-[4,5-bis(4-fluorophenyl)-2-(1-methylethyl)-1H-imidazol-1-yl]ethenyl]-4-hydroxy-tetrahydro-2H-pyran-2-one (0.27 g) as an off white crystalline solid (spectroscopic details as for Example 10).

Later fractions were combined and evaporated to give an off white crystalline solid (0.060 g) which was purified by preparative t.l.c. eluting three times with System A (3:1). The lower of the two bands was removed from the plate and the silica gel was washed with chloroform and the solvent was evaporated to give a 1:1 mixture (0.020 g) of (±)-cis-(E)-6-[2-[4,5-bis(4-fluorophenyl)-2-(1-methylethyl-1H-imidazol-1-yl]e- thenyl]-4-hydroxy-tetrahydro-2H-pyran-2-one, $R_F$ 0.32 (System A 3:1) and (±)-threo-(E)-7-[4,5-bis(4-fluorophenyl)-2-(1-methylethyl)-1H-imidazol-1-yl]-3,5-dihydroxy-6-heptenoic acid, ethyl ester, $R_F$ 0.54 (System A 3:1), δ(CDCl$_3$) values include, 1.29 (t,J 8 Hz, CO$_2$CH$_2$CH$_3$), 1.41 (d,J 6 Hz,(CH$_3$)$_2$CH), 2.30-2.56 (m,CH$_2$CO$_2$Et and CH$_2$CO$_2$CH), 3.14 and 3.15 (septets, J 6 Hz,(CH$_3$)$_2$CH), 3.96-4.10, 4.12-4.32, 4.41-4.54 and 4.63-4.73 (4m, CH=CHCH(OH), CH(OH)CH$_2$CO$_2$Et, CHOCO and CH(OH)CH$_2$CO$_2$CH), 4.21 (q,J 8 Hz,CO$_2$CH$_2$CH$_3$), 5.33 and 5.39 (2dd,J 14 Hz & 7 Hz, NCH=CH), 6.71 and 6.74 (2 d, J 14 Hz, NCH=CH), 6.89, 6.90, 7.10, 7.18-7.31 and 7.32-7.44 (t,J 9 Hz,t,J 9 Hz, q,J 9 Hz,m,m,aromatic protons).

EXAMPLE 18

(±)-Threo-(E)-7-[4,5-bis(4-fluorophenyl)-2-(1-methylethyl)-1H-imidazol-1-yl]-3,5-dihydroxy-6-heptenoic acid, sodium salt To a stirred solution of a 1:1 mixture of (±)-cis-(E)-6-[2-[4,5-bis(4-fluorophenyl)-2-(1-methylethyl)-1H-imidazol-1-yl]ethenyl]-4-hydroxy-tetrahydro-2H-pyran-2-one and (±)-threo-(E)-7-[4,5-bis(4-fluorophenyl)-2-(1-methylethyl)-1H-imidazol-1-yl]-3,5-dihydroxy-6-heptenoic acid, ethyl ester (0.008 g) was added 0.1N aqueous sodium hydroxide (0.16 ml). After 0.5 h the mixture was evaporated to dryness and the residue was partitioned between water (10 ml) and ether (10 ml). The aqueous phase was separated off, filtered and finally freeze dried to give the title product (0.006 g) as a pale yellow solid, δ(D$_2$O) values include 1.28 (d,J 7 Hz,CH$_3$CH), 2.24 (d,J 6 Hz, CH$_2$CO$_2$Na), 3.21 (septet,J 7 Hz,(CH$_3$)$_2$CH), 3.86-4.00 (m,CH(OH)CH$_2$CO$_2$Na), 4.42-4.38 (m,NCH=CHCH), 6.69 (d,J 14 Hz,NCH=CH), 6.96, 7.11 and 7.16-7.36 (t,J 9 Hz,t,J 9 Hz,m,aromatic protons).

EXAMPLE 19

(±)-Cis and trans-(E)-6-[2-[4,5-bis(4-fluorophenyl)-2-(1-methylethyl)-1H-imidazol-1-yl]ethenyl]-4-hydroxy-4-methyl-tetrahydro-2H-pyran-2-one and methyl (±)-erythro/theo-(E)-7-[4,5-bis(4-fluorophenyl)-2-(1-methylethyl)-1H-imidazol-1-yl]-3,5-dihydroxy-3-methyl-6-heptenoate To a solution of lithium bis(trimethylsilyl) amide (5.6 ml, 1M solution in THF) in dry THF (20 ml) at −78° under nitrogen was added, dropwise over 5 min, dry methyl acetate (410 μl). After 20 min, a solution of (±)-(E)-[4,5-bis(4-fluorophenyl)-2-(1-methylethyl)-1H-imidazol-1-yl]-3-hydroxy-1-hexen-5-one (706 mg) in dry THF (25 ml) was added dropwise over 20 min. Stirring was continued for 50 min at −78°. The reaction was quenched with saturated aqueous ammonium chloride solution (25 ml), allowed to warm to room temperature then diluted with ethyl acetate (50 ml) and 50% saturated aqueous ammonium chloride solution (50 ml). The layers were separated and the aqueous phase extracted with ethylacetate (2×50 ml). The combined extracts were dried and evaporated to a yellow gum (803 mg). FCC eluting with System A (1:1) gave methyl (±)-erythro/threo-(E)-7-[4,5-bis(4-fluorophenyl)-2-(1-methylethyl)-1H-imidazol-1-yl]-3,5-dihydroxy-3-methyl-6-heptenoate (0.298 g) as a yellow solid δ(CDCl$_3$) values include 6.90 and 7.0-7.4(t,J 9 Hz, and m, aromatic protons), 6.68 (d, J 14 Hz, NCH=CH), 5.20-5.32 (m, NCH=CH), 4.4-4.62 (m, NCH=CH.CH), 3.72 (s,CO$_2$CH$_3$), 3.0-3.2(m, CH(CH$_3$)$_2$), 1.39(d,J 6 Hz, CH(CH$_3$)$_2$), 1.28 (s,CH$_3$). Later fractions gave (±) trans-(E)-6-[2-[4,5-bis(4-fluorophenyl)-2-(1-methylethyl)-1H-imidazol-1-yl]-ethenyl]-4-hydroxy-4-methyl-tetrahydro-2H-pyran-2-one as a yellow glass (59 mg). δ(CDCl$_3$) 7.30-7.45 and 7.2-7.3(2m,4H,C-2 and C-6 protons of 4-fluorophenyl), 6.90 and 7.11(2t,4H, C-3 and C-5 protons of 4-fluorophenyl,J=9 Hz), 6.75(d,1H, NCH=CH,J=14.3 Hz), 5.29(dd,1H,NCH=CH,J=14.3 Hz,6.8 Hz), 5.15(m,1H,C-6 proton of pyranone), 3.14(septet,1H,CH(CH$_3$)$_2$,J=6.3 Hz), 2.66(dd,1H equatorial C-3 proton of pyranone,J=17.5 Hz,2.5 Hz), 2.45(d,1H,axial C-3 proton of pyranone,J=17.5 Hz), 1.78(2m,1H,C-5 proton of pyranone), 1.50(2m,1H,C-5 proton of pyranone), 1.41(d,6H,CH(CH$_3$)$_2$,J=6.3 Hz), 1.40(s,3H,protons of C-4 methyl of pyranone). Later fractions gave (±) cis-(E)-6-[2-[4,5-bis(4-fluorophenyl)-2-(1-methylethyl)-1H-imidazol-1-yl]ethenyl]-4-hydroxy-4-methyl-tetrahydro-2H-pyran-2-one as a yellow glass (33 mg) δ(CDCl$_3$), values include 7.30-7.45 and 7.2-7.30(2m,4H,C-2 and C-6 protons of 4-fluorophenyl), 6.90 and 7.11(2t,4H,C-3 and C-5 protons of 4-fluorophenyl, J=9 Hz), 6.72(d, 1H, NCH=CH, J=14 Hz), 5.40(dd,1H,NCH=CH,J=14 Hz,7.5 Hz), 4.74(m,1H,C-6 proton of pyranone), 3.14(septet,1H,CH(CH$_3$)$_2$,J=6.3 Hz), 2.59(s,2H,C-3 protons of pyranone), 1.93(dd,1H, one C-5 proton of pyranone,J=14.7 Hz,5 Hz), 1.52(dd,1H, one C-5 proton of pyranone,J=14.7 Hz,10 Hz).

EXAMPLE 20

Sodium (±)-erythro-(E)-7-[4,5-bis(4-fluorophenyl)-2-(1-methylethyl)-1H-imidazol-1-yl]-3,5-dihydroxy-3-methyl-6-heptenoate To a solution of (±)-trans-(E)-6-[2-[4,5-bis(4-fluorophenyl)-2-(1-methylethyl)-1H-imidazol-1-yl]ethenyl]-4-hydroxy-4-methyl-1-tetrahydro-2H-pyran-2-one (57.4 mg) in ethanol (5 ml) was added 1N aqueous sodium hydroxide solution (121 μl). After 2.5 h, the reaction was evaporated to dryness, redissolved in water (20 ml) and washed with ether (6×5 ml). The aqueous phase was freeze dried to give the title compound (49 mg) as a white powder. [MH]+493.7, δ(D$_2$O) 7.10-6.93 (m,8H, aromatics), 6.65 (d,2H,NCH=CHCH,J=16.3 Hz), 5.49 (dd,1H,NCH=CHCH,J=16.3 Hz,7.5 Hz), 4.38 (m,1H, NCH=CHCH), 3.21 (septet, 1H, CH(CH$_3$)$_2$,J=6.3 Hz), 2.28-2.38 (m, 2H,CH$_2$CO$_2$Na), 1.8-1.17 (m, 2H,CH(OH)CH$_2$), 1.27(d,6H,J=6.3 Hz), 1.13 (s,3H,CH$_3$).

EXAMPLE 21

Sodium (3R,5S,E)-7-[4,5-bis(4-fluorophenyl)-2-(1-methylethyl)-1H-imidazol-1-yl]-3,5-dihydroxy-6-heptenoate and sodium (3S,5R,E)-7-[4,5-bis(4-fluorophenyl)-2-(1-methylethyl)-1H-imidazol-1-yl]-3,5-dihydroxy-6-heptenoate Resolution of sodium (±)-erythro-(E)-[4,5-bis(4-fluorophenyl)-2-(1-methylethyl)-1H-imidazol-1-yl]-3,5-dihydroxy-6-heptenoate was carried out using the protocol as described below:

Column: 4.0×100 mm Enantiopac cartridge (LKB Co) containing α-Glycoprotein (AGP); Mobile Phase: 0.02M Sodium dihydrogen phosphate and 0.1M sodium chloride in deionised water, adjusted to pH4.0 with phosphoric acid, and containing 3% v/v isopropanol; Flow Rate: 0.3 ml min$^{-1}$; Column Conditioning: In addition to the conditioning process specified by the manufacturer, the column was equilibriated by passage of mobile phase (0.3 ml min$^{-1}$) for at least 12 h; Instrument: Hewlett Packard Model 1090M; Sample preparation: Sodium (±)-erythro-(E)-[4,5-bis(4-fluorophenyl)-2-(1-methylethyl)-1H-imidazol-1-yl]-3,5-dihydroxy-6-heptenoate (0.78 mg) was dissolved in mobile phase (1 ml); Sample Injection: 10 µl loop via Rheodyne valve; Detection: UV, 254 nm (Diode Array Detector); Sample Collection: Eluant emerging from the detector was diverted as required into 3.5 ml sample tubes that had been washed with mobile phase. Sodium (±)-erythro-(E)-7-[4,5-bis(4-fluorophenyl)-2-(1-methylethyl)-1H-imidazol-1-yl]-3,5-dihydroxy-6-heptenoate (3×10 µl samples of a 0.78 mg/ml solution) was subjected to the protocol as described above. Relevant pooled fractions totalling 2.51 ml and 1.01 ml were collected during elution of the two major peaks that had respective mean retention time maxima of 9.6 and 11.2 min. Aliquots (50 µl) of the pooled fractions were placed in clean glass-lined 100 µl polypropylene vials and 10 µl samples were analysed by hplc as described above. The shorter retention time fractions gave sodium (3R,5S,E)-7-[4,5-bis(4-fluorophenyl)-2-(1-methylethyl)-1H-imidazol-1-yl]-3,5-dihydroxy-6-heptenoate (5 µg, 85–90% enantiomerically pure) (as confirmed by spiking the sample with the product obtained in Example 8) and the longer retention time fractions gave sodium (3S,5R,E)-7-[4,5-bis(4-fluorophenyl)-2-(1-methylethyl)-1H-imidazol-1-yl]-3,5-dihydroxy-6-heptenoate (1.7 µg, >90% enantiomerically pure).

EXAMPLE 22

Methyl (±)-erythro-(E)-3,5-dihydroxy-7-[5-(4-fluorophenyl)-4-(4-hydroxyphenyl)-2-(1-methylethyl)-1H-imidazol-1-yl]-6-heptenoate Methyl (±)-erythro-(E)-3,5-dihydroxy-7-[5-(4-fluoropheny)-4-(4-methoxyphenyl)-2-(1-methylethyl)-1H-imidazol-1-yl]-6-heptenoate (200 mg) was dissolved in dichloromethane and cooled to −78° C. under nitrogen. Boron tribromide (2.4 ml, 1M solution in dichloromethane) was added and the reaction mixture was stirred at −78° for 20 min. The nitrogen flow was increased and the reaction mixture was allowed to warm to room temperature and evaporation to dryness occurred. Ammonia (1 ml S.G. 0.88 in 9 ml water) was added followed by methanol (15 ml). The reaction mixture was stirred at room temperature for 10 min and extracted with dichloromethane to give a crude product (108 mg). Purification by preparative t.l.c. eluting with ethyl acetate gave the title compound (38 mg), δ (CDCl$_3$) values include 1.4 (d,J=7 Hz, CH(CH$_3$)$_2$), 2.4 (m,CH$_2$CO$_2$Me), 3.11 (m,CH(CH$_3$)$_2$), 3.71 (s,CO$_2$CH$_3$), 4.2 (m,CHOH), 4.42 (m,CHOH), 5.3 (dd,NCH=CH), 6.5 (d,J=14 Hz, NCH=CH), 6.7–7.3 (m, aromatic protons).

EXAMPLE 23

Methyl (±)-erythro-(E)-3,5-dihydroxy-7-[5-(4-fluorophenyl)-4-(3-hydroxyphenyl)-2-(1-methylethyl)-1H-imidazol-1-yl]-6-heptenoate Methyl (±)-erythro-(E)-3,5-dihydroxy-7-[5-(4-fluorophenyl)-4-(3-methoxyphenyl)-2-(1-methylethyl)-1H-imidazol-1-yl]-6-heptenoate (120 mg) was dissolved in dichloromethane (10 ml, dried) and cooled to −78° under nitrogen. Boron tribromide (1 ml, 1M in dichloromethane, was added and the reaction mixture was stirred under nitrogen at −78° for 1 h. Sodium bicarbonate (420 mg) was added and the solution allowed to warm to −5°. Methanol (5 ml) was added and the reaction mixture was stirred for 5 min.

Dichloromethane (100 ml) was added and the extract was washed with water, dried and evaporated to dryness to give a crude product (90 mg). Purification by preparative t.l.c. eluting with ethyl acetate gave the title compound (12 mg). δ (CDCl$_3$) values include 1.4 (d, J=7 Hz, (CH$_3$)$_2$CH), 2.45 (m,CH$_2$CO$_2$Me), 3.16 (m, CH(CH$_3$)$_2$), 3.75 (s,CO$_2$CH$_3$), 4.15 (m,CHOH), 4.43 (m,CHOH), 5.35 (dd,NCH=CH), 6.6–7.3 (m, NCH=CH, aromatic protons).

As a further illustration of the present invention the following compounds were prepared according to the general procedures outlined below:

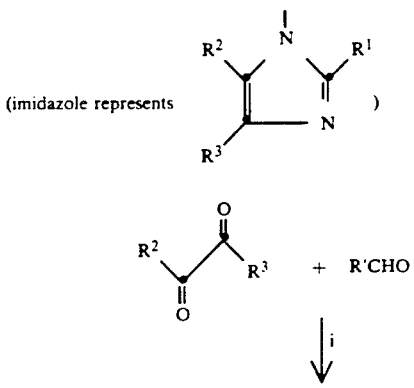

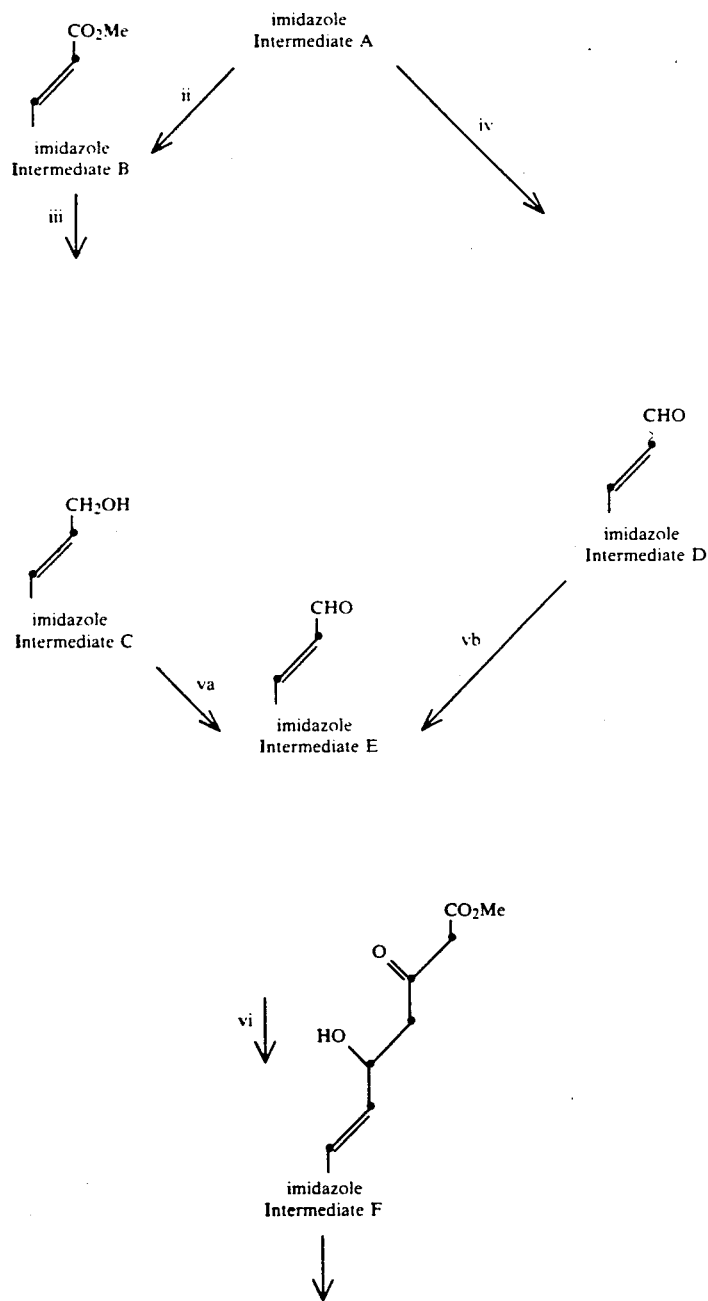

-continued

Reaction scheme

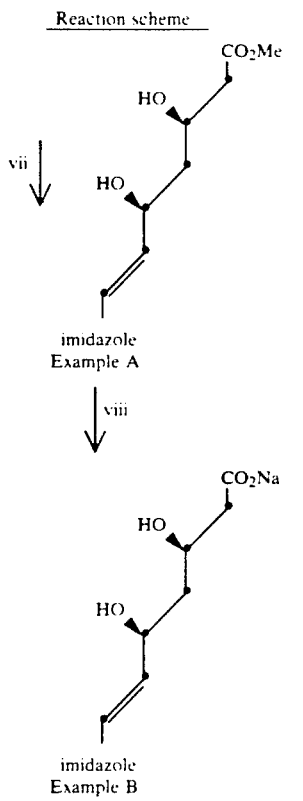

REACTION CONDITIONS i. A mixture of the appropriate dione (1 equiv.), ammonium acetate (7 equiv.) and appropriate aldehyde (1.3 equiv.) in acetic acid were heated under reflux. The reaction mixture was worked-up by for example evaporating and dissolving the residue in ethyl acetate and washing with water, sodium bicarbonate (aqueous) and brine before drying and evaporating. Further purification by column chromatography or crystallisation was sometimes necessary.

ii. A solution of Intermediate A in THF and methyl propiolate (an excess) was heated under reflux under nitrogen, with further additions of methyl propiolate where necessary. The reaction mixture was purified by CC.

iii. Diisobutylaluminium hydride (2.2 equiv, 1M solution in dichloromethane) was added to a solution of Intermediate B in dichloromethane under nitrogen at $-70°$ to $-78°$. The mixture was stirred at this temperature with addition of further diisobutylaluminium hydride where necessary. The mixture was brought to room temperature and quenched with saturated aqueous ammonium chloride solution. Water and dichloromethane were added and the mixture stirred at room temperature for 30 min before filtering and separating off the organic phase. The organic phase was washed with water, dried and evaporated to give the product.

iv. A solution of Intermediate A and propiolaldehyde (an excess of 75% w/v solution in toluene) in THF was heated under reflux with further additions of propiolaldehyde where necessary. The mixture was evaporated and purified by CC.

va. Manganese (IV) oxide (ca 30 equiv.) was added to a solution of Intermediate C in dichloromethane and the mixture stirred at room temperature before filtering. The filtrate was evaporated to give the product.

vb. A solution of Intermediate D in carbon tetrachloride was irradiated with a 200 w tungsten lamp in the presence of iodine. The mixture was filtered and evaporated. Further purification by CC was sometimes necessary.

vi. Methyl acetoacetate (1.2 equiv.) was added to sodium hydride (60% oil dispersion, 2.9 equiv.) in THF at $-3°$ under nitrogen. After 5 min n-butyl lithium (1.6M in hexanes, 1.35 equiv.) was added and the mixture stirred at $-3°$ for 10 min before adding Intermediate E (1 equiv.) in THF dropwise. The reaction was stirred at $-3°$ before quenching with saturated aqueous ammonium chloride. The aqueous solution was extracted (e.g. dichloromethane or ethyl acetate) and the residue purified by CC.

vii. Dry methanol was added to a solution of triethylborane (1.1 to 1.5 equiv. e.g. 1.27 equiv.) in dry THF and the resulting mixture stirred for 1 h at room temperature then cooled to $-70°$ to $-78°$ C. Intermediate F (1 equiv.) in dry THF was added slowly and the solution stirred under nitrogen for 1 h. Sodium borohydride (1 to 1.38 equiv. e.g. 1.2 equiv.) was added and the reaction stirred at $-70°$ to $-78°$ before quenching with aqueous saturated ammonium chloride solution. The mixture was allowed to warm to room temperature, diluted with water and extracted with ethyl acetate. The extracts were combined, dried and evaporated and azeotroped four times with methanol. The residue was purified by CC or FCC.

viii. Aqueous sodium hydroxide solution (0.1N) was added to a solution of Example A in THF at room temperature and the mixture stirred for 5 min to 1.5 h (e.g. 30 min). The solution was diluted with water and washed with ether before freeze drying the aqueous layer to give the product.

TABLE 1

INTERMEDIATE A

| Int. A | R¹ | R² | R³ | Rxn. Time/ hour | |
|---|---|---|---|---|---|
| 1[1] | isopropyl | 4-fluorophenyl | 4-pyridinyl | 4 | δ(CDCl₃) 1.42(d), 3.15(septet), 8.46(m), 9.30(s) |
| 2[1] | " | 4-fluorophenyl | 3-pyridinyl | 4 | δ(CDCl₃) 1.41(d) 3.15(septet) 7.05(t), 8.45(m), 8.70(m). |
| 3a | " | 3,5-dimethylphenyl | 4-fluorophenyl | 6 | νmax (Nujol) 1537, 838 cm⁻¹ |
| 3b | " | 4-fluorophenyl | 3,5-dimethylphenyl | | |
| 4a | " | 4-fluorophenyl | 3-chlorophenyl | 3 | νmax (Nujol) 1600, 1507, 839, 787 cm⁻¹ |
| 4b | " | 3-chlorophenyl | 4-fluorophenyl | | |
| 5a | " | 5-fluorophenyl | 3,5-dichlorophenyl | 3 | mp. 223–4° |
| 5b | " | 3,5-dichlorophenyl | 4-fluorophenyl | | |
| 6a | " | 3,5-dichlorophenyl | 3-bromophenyl | 18 | νmax (CHBr₃) 3430, 1592, 1575, 1560, 801 cm⁻¹ |
| 6b | " | 3-bromophenyl | 3,5-dichlorophenyl | | |
| 7[1] | " | 4-fluorophenyl | 3,5-dimethyl-4-fluorophenyl | 4 | m.p. 230–235° |
| 8[1] | " | 3-bromophenyl | 3,5-dimethyl-4-fluorophenyl | 4 | λmax (EtOH) 294.4 nm (ε11,620) |
| 9[1] | " | 3,5-dimethyl-4-fluorophenyl | phenyl | 4 | νmax (EtOH) 287.6 nm (ε10,917) |
| 10a | " | 4-fluorophenyl | 4-methylphenyl | 6 | νmax (Nujol) 1515, 820 cm⁻¹ |
| 10b | " | 4-methylphenyl | 4-fluorophenyl | | |
| 11a | " | 4-fluorophenyl | 3,5-diethyl-4-fluorophenyl | 6 | λmax (EtOH) 223.2(inf) (ε17,441), 235.8 (inf) |
| 11b | " | 3,5-diethyl-4-fluorophenyl | 4-fluorophenyl | | (ε12,691), 246.4(inf) (ε9642), 287.0 nm (inf) (ε11,450) |
| 12a | isopropyl | 4-fluorophenyl | 3-bromophenyl | 4.5 | δ(CDCl₃), 1.40(d), 3.12(septet), 6.90-7.87(m), 9.01(s), 9.14(s) |
| 12b | " | 3-bromophenyl | 4-fluorophenyl | | |
| 13a | " | 4-chloro-3,5-dimethylphenyl | 4-fluorophenyl | 5 | λmax (EtOH) 221 (18,514), 238 (14,365), 248 (9,943), 219 nm (ε12,274) |
| 13b | " | 4-fluorophenyl | 4-chloro-3,5-dimethylphenyl | | |
| 14a | " | 4-fluoro-2-methylphenyl | 4-fluorophenyl | 7 | λmax (EtOH) 258 (inf) (10,402), 272 nm (ε11,682) |
| 14b | " | 4-fluorophenyl | 4-fluoro-2-methylphenyl | | |
| 15a | " | 5-chloro-2-methylphenyl | 4-fluorophenyl | 5 | δ(CDCl₃) 1.38(d), 1.97(s), 3.12(m), 6.92 and 7.03-7.50(m), 9.10-9.43(m) |
| 15b | " | 4-fluorophenyl | 5-chloro-2-methylphenyl | | |
| 16[1] | " | 4-methoxyphenyl | 4-fluorophenyl | 18 | δ(CDCl₃) 1.35(d), 3.15(m), 3.8(s), 6.8-7.5(m), 7.98(s) |
| 17[1] | " | 3-methoxyphenyl | 4-fluorophenyl | 7 | δ(CDCl₃) 1.38(d), 3.12(m), 3.7(s), 6.8-7.4(m) 8.8(m) |
| 18 | " | 3-chlorophenyl | 3-chlorophenyl | 5 | νmax (DMSO-d₆) 3488, 1664, 1597 cm⁻¹ |
| 19* | CF₃ | 3-chlorophenyl | 3-chlorophenyl | 22 | νmax (CHBr₃) 3401, 789, 756 cm⁻¹ |
| 20 | isopropyl | 3,5-dimethylphenyl | 3,5-dimethylphenyl | 8 | νmax (Nujol) 1602, 847, 705 cm⁻¹ |
| 21a | " | 4-fluorophenyl | 4-chlorophenyl | 6 | m.p. 237–239° |
| 21b | " | 4-chlorophenyl | 4-fluorophenyl | | |
| 22a | " | 4-fluorophenyl | 3,5-dibromophenyl | 4 | νmax (Nujol) 1539, 854 cm⁻¹ |
| 22b | " | 3,5-dibromophenyl | 4-fluorophenyl | | |
| 23[1] | " | 4-fluorophenyl | 3-trifluoromethylphenyl | 4 | Rf 0.25 (System A 1:3) |
| 24** | Me | 4-fluorophenyl | 4-fluorophenyl | 22 | νmax (Nujol) 835, 1514 cm⁻¹ |
| 25 | t-Bu | 4-fluorophenyl | 4-fluorophenyl | 6 | νmax (CHBr₃) 838, 1512 cm⁻¹ |

[1]together with tautomeric form
*hemiacetal (3 + 1.2 equiv.) used instead of aldehyde
**5.2 equiv. aldehyde used

TABLE 2

INTERMEDIATE B

| Int. B | From Int. A | R¹ | R² | R³ | Rxn. Time/ h | |
|---|---|---|---|---|---|---|
| 4a | 4a + | isopropyl | 4-fluorophenyl | 3-chlorophenyl | 60 | νmax (CHBr₃) 1713, 1643 cm⁻¹ |
| 4b | 4b | " | 3-chlorophenyl | 4-fluorophenyl | | |
| 5a | 5a + | " | 4-fluorophenyl | 3,5-dichlorophenyl | 42 | m.p. 160–163°C. |
| 5b | 5b | " | 3,5-dichlorophenyl | 4-fluorophenyl | | |
| 7a | 7 | " | 4-fluorophenyl | 3,5-dimethyl-4-fluorophenyl | 23 | λmax (EtOH) 249 nm (ε23,725) |
| 7b | | " | 3,5-dimethyl-4-fluorophenyl | 4-fluorophenyl | | |
| 8a | 8 | " | 3-bromophenyl | 3,5-dimethyl-4-fluorophenyl | 23 | δ(CDCl₃) 1.45(d), 2.15(s), 3.22(m), 3.71(s), 5.32(d), 7.0–7.6(m), 7.8(d). |
| 8b | | | 3,5-dimethyl-4-fluorophenyl | 3-bromophenyl | 23 | δ(CDCl₃) 1.39 (d), 2.21(s), 3.15(m), 3.65(s), 5.26(d), 6.9-7.25(m), 7.7(d). |
| 9a | 9 | " | 3,5-dimethyl-4-fluorophenyl | phenyl | 7 | νmax 1720, 1645 cm⁻¹ |
| 9b | | | phenyl | 3,5-dimethyl-4-fluorophenyl | | |
| 10a | 10a + | " | 4-fluorophenyl | 4-methylphenyl | 21 | δ(CDCl₃) 1.45(d), 2.3(s), 2.5(s), 3.25 septet, 3.7(m), 5.3(m), 6.85-7.5(m), 7.8(d) |
| 10b | 10b | " | 4-methylphenyl | 4-fluorophenyl | | |
| 11a | 11a + | " | 4-fluorophenyl | 3,5-diethyl-4-fluorophenyl | 21 | λmax (EtOH) 249.6 (ε23,336), 268.8 (inf), (ε11,096), 301.8 nm (inf),(ε9.723) |
| 11b | 11b | " | 3,5-diethyl-4-fluorophenyl | 4-fluorophenyl | | |
| 12a | 12a + | isopropyl | 4-fluorophenyl | 3-bromophenyl | 66 | νmax (CHBr₃) 1713, 1642 cm⁻¹ |
| 12b | 12b | " | 3-bromophenyl | 4-fluorophenyl | | |
| 14a | 14a + 14b | " | 4-fluoro-2-methylphenyl | 4-fluorophenyl | 97.5 | δ(CDCl₃) 1.46(d), 1.48(d), 2.05(s), 3.27(septet) 3.70(s), 5.12(d), 6.90(t), 6.97-7.43(t), 7.82(d) |
| 14b | 14a + | " | 4-fluorophenyl | 4-fluoro-2-methylphenyl | 97.5 | δ(CDCl₃) 1.37(m), 1.45(d), 2.03(s), |

TABLE 2-continued

INTERMEDIATE B

| Int B | From Int A | R[1] | R[2] | R[3] | Rxn. Time/ h | |
|---|---|---|---|---|---|---|
| 14c* | 14b | | 4-fluoro-2-methylphenyl | 4-fluorophenyl | | 2.14(s), 2.97(septet), 3.27(septet), 3.62 (s) 3.74(s), 5.46(d), 5.88(d), 6.66–7.46(m), 7.87(d) |
| 15a | 15a + 15b | " | 5-chloro-2-methylphenyl | 4-fluorophenyl | 71 | δ(CDCl₃) 1.48(d), 2.03(s), 3.27(septet), 3.70(s), 5.13(d), 6.93(t), 7.27–7.45(t), 7.82(d) |
| 15b | 15a + 15b | " | 4-fluorophenyl | 5-chloro-2-methylphenyl | 71 | δ(CDCl₃) 1.45(d), 2.02(s), 3.27(septet) 3.73(s), 5.47(d), 6.99–7.17(m), 7.86(d) |
| 16a | 16 | isopropyl | 4-methoxyphenyl | 4-fluorophenyl | 7 | δ(CDCl₃) 1.45(d), 3.22(m), 3.69(s), 3.9 (s), 5.32(d), 6.9–7.5(m), 7.8(d) |
| 16b | 16 | " | 4-fluorophenyl | 4-methoxyphenyl | 7 | δ(CDCl₃) 1.45(d), 3.24(m), 3.7(s), 3.78 (s), 5.25(d), 6.75–7.4(m), 7.8(d) |
| 17a | 17 | " | 3-methoxyphenl | 4-fluorophenyl | 7 | νmax (Nujol) 1719 cm⁻¹ |
| 17b | 17 | isopropyl | 4-fluorophenyl | 3-methoxyphenyl | 7 | νmax (Nujol) 1708 cm⁻¹ |
| 18a** | 18 | " | 3-chlorophenyl | 3-chlorophenyl | 20 | Rf 0.59 (System A 3:7) |
| 18b*** | 18 | " | 3-chlorophenyl | 3-chlorophenyl | 20 | Rf 0.47 and 0.59 (System A 3:7) |
| 22a | 22a + | " | 3,5-dibromophenyl | 4-fluorophenyl | 52 | νmax (Nujol) 1723, 1713, 1647, 1590, |
| 22b | 22b | " | 4-fluorophenyl | 3,5-dibromophenyl | | 1542, 1506 cm⁻¹ |
| 24 | 24 | Me | 4-fluorophenyl | 4-fluorophenyl | 16 | δ(CDCl₃) 2.65(s), 3.7(s), 5.5(d), 6.8–7.45(m), 7.68(d) |
| 25 | 25 | t-Bu | 4-fluorophenyl | 4-fluorophenyl | 18 | δ(CDCl₃) 1.55(s), 3.7(s), 4.98(d), 6.8–7.4(m), 8.15(d) |
| 26a* | see | isopropyl | 4-fluorophenyl | 4-fluorophenyl | 8 | δ(CDCl₃) 3.57(s), 5.95(d), 6.78(d) |
| 26b* | note | " | 4-fluorophenyl | 4-fluorophenyl | 8 | δ(CDCl₃) 3.65(s), 5.24(d), 7.79(d) |

*Z-isomer
**E-isomer
***mixture of E and Z isomers
note - B26a and B26b prepared from 4,5-bis(4-fluorophenyl)-2-(1-methylethyl)-1H-imidazol-1-yl]-2-propenoate (Intermediate 6) with separation by cc

TABLE 3

INTERMEDIATE C

| Int. C | From Int. B | R[1] | R[2] | R[3] | Rxn. Time/ h | |
|---|---|---|---|---|---|---|
| 4a | 4a + | isopropyl | 4-fluorophenyl | 3-chlorophenyl | 1 | νmax (CHBr₃) 3592, 1506, 841, 788 cm⁻¹ |
| 4b | 4b | " | 3-chlorophenyl | 4-fluorophenyl | | |
| 5a | 5a + | " | 4-fluorophenyl | 3,5-dichlorophenyl | 2 | νmax (CHBr₃) 3592, 1555, 1505, 840, 801 cm⁻¹ |
| 5b | 5b | " | 3,5-dichlorophenyl | 4-fluorophenyl | | |
| 7a | 7a + | " | 4-fluorophenyl | 3,5-dimethyl-4-fluorophenyl | 1 | λmax (EtOH) 245 nm (ε12,622) |
| 7b | 7b | " | 3,5-dimethyl-4-fluorophenyl | 4-fluorophenyl | | |
| 8a | 8a | " | 3-bromophenyl | 3,5-dimethyl-4-fluorophenyl | 1 | λmax (EtOH) 239 nm (ε18,695) |
| 8b | 8b | " | 3,5-dimethyl-4-fluorophenyl | 3-bromophenyl | 1 | λmax (EtOH) 280.8 nm (ε11,085) |
| 9a | 9a + | " | 3,5-dimethyl-4-fluorophenyl | phenyl | 1 | λmax (EtOH) 247 nm (ε11,481) |
| 9b | 9b | " | phenyl | 3,5-dimethyl-4-fluorophenyl | | |
| 10a | 10a + | " | 4-fluorophenyl | 4-methylphenyl | 2.5 | δ(CDCl₃) 1.4(d), 2.3(s), 2.39(s), 3.15 (septet), 4.15(d), 5.5(m), 6.6(d), 6.8–7.5(m) |
| 10b | 10b | " | 4-methylphenyl | 4-fluorophenyl | | |
| 11a | 11a + | " | 4-fluorophenyl | 3,5-diethyl-4-fluorophenyl | 3 | δ(CDCl₃) 1.05–1.25(m), 1.4(d), 2.45–2.7(m), 3.15(septet), 4.15(m), 5.45–5.10(m), 6.6(d), 6.85–7.5(m) |
| 11b | 11b | " | 3,5-diethyl-4-fluorophenyl | 4-fluorophenyl | | |
| 12a | 12a + | " | 4-fluorophenyl | 3-bromophenyl | 1 | λmax (EtOH) 229(inf), (19,519), 293 nm, (ε9,718) |
| 12b | 12b | " | 3-bromophenyl | 4-fluorophenyl | | |
| 14a | 14a | isopropyl | 4-fluoro-2-methylphenyl | 4-fluorophenyl | 10 min | λmax (EtOH) 263 nm (ε14,516) |
| 14b | 14b + 14c | " | 4-fluorophenyl | 4-fluoro-2-methylphenyl | 10 min | νmax (CHBr₃) 3592, 3185 cm⁻¹ |
| 15a | 15a | " | 5-chloro-2-methylphenyl | 4-fluorophenyl | 1.5 | λmax (EtOH) 257 nm (ε13,471) |
| 15b | 15b | " | 4-fluorophenyl | 5-chloro-2-methylphenyl | 5 min | δ(CDCl₃) 1.40(d), 1.98(s), 3.18 (septet), 4.22(m), 5.63(d), 6.70(d), 6.95–7.22(m) |
| 16a | 16a | " | 4-methoxyphenyl | 4-fluorophenyl | 1 | νmax (Nujol) 3200 cm⁻¹ |
| 16b | 16b | " | 4-fluorophenyl | 4-methoxyphenyl | 2 | νmax (Nujol) 3162 cm⁻¹ |
| 17a | 17a | " | 3-methoxyphenyl | 4-fluorophenyl | 45 min | νmax (Nujol) 3154 cm⁻¹ |
| 17b | 17b | " | 4-fluorophenyl | 3-methoxyphenyl | 45 min | νmax (Nujol) 3245 cm⁻¹ |
| 18 | 18a | " | 3-chlorophenyl | 3-chlorophenyl | 1 | Rf 0.49 (System A 2:3) |
| 19 | see note | CF₃ | 3-chlorophenyl | 3-chlorophenyl | 1 | Rf 0.21 (System A 1:4) |
| 22a | 22a + | isopropyl | 4-fluorophenyl | 3,5-dibromophenyl | 2 | νmax (CHBr₃) 3592, 1668, 1587, 1544, 1505, 841 cm⁻¹ |
| 22b | 22b | " | 3,5-dibromophenyl | 4-fluorophenyl | | |
| 24 | 24 | Me | 4-fluorophenyl | 4-fluorophenyl | 1.5 | δ(CDCl₃) 2.5(s), 4.15–4.25(m), 5.55–5.70(m), 6.53(d), 6.8–7.4(m) |
| 25 | 25 | t-Bu | 4-fluorophenyl | 4-fluorophenyl | 3 | δ(CDCl₃) 1.5(s), 4.04–4.15(m), 5.32 (dt), 6.83(d), 6.85–7.45(m) |

TABLE 3-continued

INTERMEDIATE C

| Int. C | From Int. B | R¹ | R² | R³ | Rxn. Time/h | |
|---|---|---|---|---|---|---|
| 26a* | 26a | isopropyl | 4-fluorophenyl | 4-fluorophenyl | 1 | Rf ca 0.12 (System A 1:2) |

Note - B19 prepared from (E) and (Z)-3-[4,5-bis(3-chlorophenyl)-2-trifluoromethyl-1H-imidazol-1-yl]-2-propanoic acid, methyl ester (intermediate 23)
*Z-isomer

TABLE 4

INTERMEDIATE D

| Int. D | From Int. A | R¹ | R² | R³ | Rxn. Time/h | |
|---|---|---|---|---|---|---|
| 3a | 3a + | isopropyl | 3,5-dimethylphenyl | 4-fluorophenyl | 23 | δ(CDCl₃) 1.4–1.6(m), 2.2–2.4(m), 3.0–3.4(m), 5.6–5.7(m), 5.9–6.0(m), 6.8–7.6(m), 9.3–9.6(m) |
| 3b | 3b | " | 4-fluorophenyl | 3,5-dimethylphenyl | | |
| 6a | 6a + | " | 3-bromophenyl | 3,5-dichlorophenyl | 23 | δ(CDCl₃) 1.4(d), 1.48(d), 3.14(septet), 3.23(septet), 5.70(dd), 6.02–6.15(m), 7.04–7.83(m), 9.40–9.55(m) |
| 6b | 6b | " | 3,5-dichlorophenyl | 3-bromophenyl | | |
| 13a | 13a + | " | 4-chloro-3,5-dimethylphenyl | 4-fluorophenyl | 23 | νmax (CHBr₃) 1681, 1635 cm⁻¹ |
| 13b | 13b | " | 4-fluorophenyl | 4-chloro-3,5-dimethylphenyl | | |
| 20 | 20 | " | 3,5-dimethylphenyl | 3,5-dimethylphenyl | 18 | δ(CDCl₃) 1.41(d), 1.50(d), 2.18(s), 2.34(s), 3.26(septet), 5.69(dd), 5.97(t), 6.83(s), 6.98(s), 7.12(s), 7.50(d), 9.36(d), 9.50(d) |
| 21a | 21a + | " | 4-chlorophenyl | 4-fluorophenyl | 16 | δ(CDCl₃) 1.40(d), 1.50(d), 3.07 (septet), 3.23(septet), 5.59–5.75(m), 5.97–6.07(m), 6.88–7.59(m), 9.37–9.53 (m) |
| 21b | 21b | " | 4-fluorophenyl | 4-chlorophenyl | | |
| 23a | 23 | " | 4-fluorophenyl | 3-trifluoromethylphenyl | 28 | Rf 0.23 and 0.28 (System A 1:3) |
| 23b | | " | 3-trifluoromethylphenyl | 4-fluorophenyl | | |

*E isomer only

TABLE 5

INTERMEDIATE E - route Va

| Int. E | From Int. C | R¹ | R² | R³ | Rxn. Time/h | |
|---|---|---|---|---|---|---|
| 1 | see note | isopropyl | 4-fluorophenyl | 4-pyridinyl | 1 | δ(CDCl₃) 1.50(d), 3.25(septet), 5.69(dd), 7.50(d), 8.45(m), 9.41(d) |
| 2 | see note | isopropyl | 4-fluorophenyl | 3-pyridinyl | 2 | δ(CDCl₃) 1.50(d), 3.25(septet), 5.68(dd), 7.50(d), 7.80(m), 8.42(m), 8.61(m), 9.41(d) |
| 4a | 4a + 4b | isopropyl | 4-fluorophenyl | 3-chlorophenyl | 1.5 | νmax (CHBr₃) 1681, 1635, 841, 790 cm⁻¹ |
| 4b | | isopropyl | 3-chlorophenyl | 4-fluorophenyl | | |
| 5a | 5a + 5b | isopropyl | 4-fluorophenyl | 3,5-dichlorophenyl | 1.5 | νmax (CHBr₃) 1683, 1635, 1556, 1506, 841, 804 cm⁻¹ |
| 5b | | isopropyl | 3,5-dichlorophenyl | 4-fluorophenyl | | |
| 7a | 7a + 7b | isopropyl | 4-fluorophenyl | 3,5-dimethyl-4-fluorophenyl | 1.75 | δ(CDCl₃) 1.48(d), 2.1(s), 2.29(s), 3.25(m), 5.68(m), 6.85–7.55(m), 9.4(d) |
| 7b | | isopropyl | 3,5-dimethyl-4-fluorophenyl | 4-fluorophenyl | | |
| 8a | 8a | isopropyl | 3-bromophenyl | 3,5-dimethyl-4-fluorophenyl | 1 | λmax (EtOH) 252 nm (ε21,980) |
| 8b | 8b | isopropyl | 3,5-dimethyl-4-fluorophenyl | 3-bromophenyl | 1 | λmax (EtOH) 263 nm (ε19,420) |
| 9a | 9a + 9b | isopropyl | 3,5-dimethyl-4-fluorophenyl | phenyl | 1 | λmax (EtOH) 260 nm (ε20,297) |
| 9b | | | phenyl | 3,5-dimethyl-4-fluorophenyl | | |
| 10a | 10a + | isopropyl | 4-fluorophenyl | 4-methylphenyl | 1.5 | νmax (CHBr₃) 1679 cm⁻¹ |
| 10b | 10b | isopropyl | 4-methylphenyl | 4-fluorophenyl | | |
| 11a | 11a + | isopropyl | 4-fluorophenyl | 3,5-diethyl-4-fluorophenyl | 2 | δ(CDCl₃) 1.05–1.4(m), 1.4–1.5(m), 2.45–2.75(m), 3.2(septet), 5.6–5.8(m), 6.9–7.6(m), 9.39(m) |
| 11b | 11b | isopropyl | 3,5-diethyl-4-fluorophenyl | 4-fluorophenyl | | |
| 12a | 12a + | isopropyl | 4-fluorophenyl | 3-bromophenyl | 1 | νmax (CHBr₃) 1680, 1636 cm⁻¹ |
| 12b | 12b | isopropyl | 3-bromophenyl | 4-fluorophenyl | | |
| 14a | 14a | isopropyl | 4-fluoro-2-methylphenyl | 4-fluorophenyl | 3 | λmax (EtOH) 262 (25,209), 322 nm (ε8,134) |
| 14b | 14b | isopropyl | 4-fluorophenyl | 4-fluoro-2-methylphenyl | 3 | νmax (CHBr₃) 1681 cm⁻¹ |
| 15a | 15a | isopropyl | 5-chloro-2-methylphenyl | 4-fluorophenyl | 1 | λmax (EtOH) 256 (21,708), 314 nm (ε10,376) |
| 15b | 15b | isopropyl | 4-fluorophenyl | 5-chloro-2-methylphenyl | 1.5 | δ(CDCl₃) 1.47(d), 2.05(s), 3.27(septet), 5.83(m), 7.01–7.20(m), 7.60(d), 9.48(d) |
| 16a | 16a | isopropyl | 4-methoxyphenyl | 4-fluorophenyl | 1 | δ(CDCl₃) 1.5(d), 3.22(m), 3.9(s), 5.68(m), 6.85–7.5(m), 7.52(d), 9.4(d) |
| 16b | 16b | isopropyl | 4-fluorophenyl | 4-methoxyphenyl | 1 | νmax (CHBr₃) 1679 cm⁻¹ |
| 17a | 17a | isopropyl | 3-methoxyphenyl | 4-fluorophenyl | 1 | δ(CDCl₃) 1.5(d), 3.24(m), 3.8(s), 5.7(dd), 6.8–7.5(m), 9.4(d) |
| 17b | 17b | isopropyl | 4-fluorophenyl | 3-methoxyphenyl | 2 | δ(CDCl₃) 1.4(d), 3.25(m), 3.68(s), 5.65(dd), 6.7–7.4(m), 7.51(d), 9.4(d) |
| 18 | 18 | isopropyl | 3-chlorophenyl | 3-chlorophenyl | 1.5 | Rf 0.73 (System A 1:1) |

TABLE 5-continued

INTERMEDIATE E - route Va

| Int. E | From Int. C | R¹ | R² | R³ | Rxn. Time/h | |
|---|---|---|---|---|---|---|
| 19 | 19 | CF₃ | 3-chlorophenyl | 3-chlorophenyl | 1 | Rf 0.31 (System A 3:17) |
| 22a | 22a → 22b | isopropyl | 4-fluorophenyl | 3,5-dibromophenyl | 2.5 | υmax (CHBr₃) 1682, 1634, 1545, 1506, 841 cm⁻¹ |
| 22b | 22b | isopropyl | 3,5-dibromophenyl | 4-fluorophenyl | | |
| 24 | 24 | Me | 4-fluorophenyl | 4-fluorophenyl | 2 | δ(CDCl₃) 2.7(s), 5.88(dd), 6.9-7.45(m), 9.4(d) |
| 25 | 25 | t-Bu | 4-fluorophenyl | 4-fluorophenyl | 3 | δ(CDCl₃) 1.6(s), 5.23(dd), 6.8-7.45(m), 7.92(d), 9.4(d) |
| 26a* | 26a | isopropyl | 4-fluorophenyl | 4-fluorophenyl | 3.75 | δ(CDCl₃) 1.40(d), 2.06(septet), 6.0(t), 6.96(t), 7.09(t), 7.15-7.50(m), 7.30(d), 9.48(d) |

Note -
E1 prepared from (E)-3-[5-(4-fluorophenyl)-2-(1-methylethyl)-4-(4-pyridinyl)-1H-imidazol-1-yl]-2-propenol - Intermediate 21
E2 prepared from (E)-3-[5-(4-fluorophenyl)-2-(1-methylethyl)-4-(3-pyridinyl)-1H-imidazol-1-yl]-2-propenol - Intermediate 22
*Z isomer

TABLE 6

INTERMEDIATE E - route Vb

| Int. E | From Int. D | R¹ | R² | R³ | Rxn. Time/h | |
|---|---|---|---|---|---|---|
| 3a | 3a → 3b | isopropyl | 3,5-dimethylphenyl | 4-fluorophenyl | 16 | δ(CDCl₃) 1.5(d), 2.35(s), 3.25 (septet), 5.65(dd), 6.8-6.98(m), 7.1(s), 7.4-7.55(m), 9.4(d) |
| 3b | 3b | isopropyl | 4-fluorophenyl | 3,5-dimethylphenyl | 16 | δ(CDCl₃) 1.5(d), 2.2(s), 3.25 (septet), 5.65(dd), 6.8-7.4(m), 7.5(d), 9.4(d) |
| 6a | 6a → 6b | isopropyl | 3,5-dichlorophenyl | 3-bromophenyl | 24 | δ(CDCl₃) 1.48(d), 3.23(septet), 5.70(dd), 7.04-7.83(m), 9.45(t) |
| 6b | | isopropyl | 3-bromophenyl | 3,5-dichlorophenyl | | |
| 13a | 13a → 13b | isopropyl | 4-chloro-3,5-dimethylphenyl | 4-fluorophenyl | 24 | λmax (EtOH) 224(inf), (24,329), 251 (23,655), 262(inf) (22,861), 289(inf) (13,375), 301 nm (inf) (ε10,557) |
| 13b | 13a → 13b | isopropyl | 4-fluorophenyl | 4-chloro-3,5-dimethylphenyl | 24 | λmax (EtOH) 263 (25,679), 291(inf), (13,256), 316 nm (ε10,835) |
| 20 | 20 | isopropyl | 3,5-dimethylphenyl | 3,5-dimethylphenyl | 16 | λmax (CH₂Cl₂) 263.4 nm (ε23,281), 326.0 nm (ε8642) |
| 21a | 21a → 21b | isopropyl | 4-fluorophenyl | 4-chlorophenyl | 22 | υmax (CHBr₃) 1681, 1635, 1508, 840 cm⁻¹ |
| 21b | 21b | isopropyl | 4-chlorophenyl | 4-fluorophenyl | | |
| 23a | 23a → 23b | isopropyl | 4-fluorophenyl | 3-trifluoromethylphenyl | 20 | Rf 0.22 and 0.28 (System A 1:3) |
| 23b | 23b | isopropyl | 3-trifluoromethylphenyl | 4-fluorophenyl | | |

TABLE 7

INTERMEDIATE F

| Int. F | From Int. E | R¹ | R² | R³ | Rxn. Time/min | |
|---|---|---|---|---|---|---|
| 1 | 1 | isopropyl | 4-fluorophenyl | 4-pyridinyl | 10 | δ(CDCl₃) 1.42(d), 2.61(m), 3.13 (septet), 3.45(s), 3.76(s), 4.65 (m), 5.32(dd), 6.68(d), 8.41(m) |
| 2 | 2 | isopropyl | 4-fluorophenyl | 3-pyridinyl | 10 | δ(CDCl₃) 1.42(d), 2.61(m), 3.15 (septet), 3.45(s), 3.75(s), 4.61 (m), 5.30(dd), 6.72(d), 7.80(m), 8.38(m), 8.59(m). |
| 3a | 3a | isopropyl | 3,5-dimethylphenyl | 4-fluorophenyl | 30 | υmax (CHBr₃) 1736, 1713, 3700 cm⁻¹ |
| 3b | 3b | isopropyl | 4-fluorophenyl | 3,5-dimethylphenyl | 30 | υmax (CHBr₃) 1740, 1712 cm⁻¹ |
| 4a | 4a + 4b | isopropyl | 4-fluorophenyl | 3-chlorophenyl | 50 | λmax (MeOH) 225.6(inf) (ε19,784), 278.0 nm (ε12,947) |
| 4b | | isopropyl | 3-chlorophenyl | 4-fluorophenyl | | |
| 5a | 5a + 5b | isopropyl | 4-fluorophenyl | 3,5-dichlorophenyl | 45 | λmax (MeOH) 231.2(inf) (ε19,477), 281.0 nm (ε12,050) |
| 5b | | isopropyl | 3,5-dichlorophenyl | 4-fluorophenyl | | |
| 6a | 6a + 6b | isopropyl | 3,5-dichlorophenyl | 3-bromophenyl | 45 | υmax (CHBr₃) 3578, 1742, 1713, 1590, 1559, 802, 788 cm⁻¹ |
| 6b | | isopropyl | 3-bromophenyl | 3,5-dichlorophenyl | | |
| 7a | 7a + 7b | isopropyl | 4-fluorophenyl | 3,5-dimethyl-4-fluorophenyl | 30 | δ(CDCl₃) 1.4(d), 2.27(s), 2.6(m), 3.15(m), 3.45(s), 3.75(s), 4.6-4.7(m), 5.2-5.35(m), 6.66(m), 6.85-7.5(m) |
| 7b | | isopropyl | 3,5-dimethyl-4-fluorophenyl | 4-fluorophenyl | | |
| 8a | 8a | isopropyl | 3-bromophenyl | 3,5-dimethyl-4-fluorophenyl | 30 | δ(CDCl₃) 1.4(d), 2.15(s), 2.62(d), 3.1(m), 3.45(s), 3.75(s), 4.7(m), 5.3(dd), 6.71(d), 7.05-7.5(m) |
| 8b | 8b | isopropyl | 3,5-dimethyl-4-fluorophenyl | 3-bromophenyl | 30 | δ(CDCl₃) 1.4(d), 2.15(s), 2.6(m), 3.13(m), 3.46(s), 3.75(s), 4.6-4.7(m), 5.3(dd), 6.68(d), 6.9-7.8(m) |
| 9a | 9a + 9b | isopropyl | 3,5-dimethyl-4-fluorophenyl | phenyl | 30 | υmax (CHBr₃) 3585, 1741 cm⁻¹ |
| 9b | | isopropyl | phenyl | 3,5-dimethyl-4-fluorophenyl | | |
| 10a | 10a + | isopropyl | 4-flurophenyl | 4-methylphenyl | 40 | υmax (CHBr₃) 1738, 1714 cm⁻¹ |

TABLE 7-continued

INTERMEDIATE F

| Int. F | From Int E | R¹ | R² | R³ | Rxn Time/min | |
|---|---|---|---|---|---|---|
| 10b | 10b | isopropyl | 4-methylphenyl | 4-fluorophenyl | | |
| 11a | 11a | isopropyl | 4-fluorophenyl | 3,5-diethyl-4-fluorophenyl | 40 | δ(CDCl₃) 1.0-1.3(m), 1.4(m), |
| 11b | 11b | isopropyl | 3,5-diethyl-4-fluorophenyl | 4-fluorophenyl | | 2.5-2.7(m), 2.6(m), 3.1(septet), 3.45(m), 3.7(s), 4.62(m), 5.2-5.4(m), 6.6-6.85(m), 6.8-7.45(m) |
| 12a | 12a | isopropyl | 4-fluorophenyl | 3-bromophenyl | 30 | λmax (EtOH) 229(inf) (11,435), |
| 12b | 12b | isopropyl | 3-bromophenyl | 4-fluorophenyl | | 261 nm (inf) (ε12,282) |
| 13a | 13a | isopropyl | 4-chloro-3,5-dimethylphenyl | 4-fluorophenyl | 30 | νmax (CHBr₃) 1741, 1713 cm⁻¹ |
| 13b | 13b | isopropyl | 4-fluorophenyl | 4-chloro-3,5-dimethylphenyl | 30 | νmax (CHBr₃) 1741, 1713 cm⁻¹ |
| 14a | 14a | isopropyl | 4-fluoro-2-methylphenyl | 4-fluorophenyl | 30 | δ(CDCl₃) 1.41(m), 2.03(m), 2.49(m), 3.12(m), 3.43(s), 3.77(s), 4.55(m), 5.13(m), 6.70(m), 6.82-7.45(m) |
| 14b | 14b | isopropyl | 4-fluorophenyl | 4-fluoro-2-methylphenyl | 30 | δ(CDCl₃) 1.39(d), 2.09(s), 2.68(d), 3.15(septet), 3.46(s), 3.77(s), 4.67(m), 5.37(dd), 6.68-7.16(m) |
| 15a | 15a | isopropyl | 5-chloro-2-methylphenyl | 4-fluorophenyl | 30 | νmax (CHBr₃) 3578, 1739, 1713 cm⁻¹ |
| 15b | 15b | isopropyl | 4-fluorophenyl | 5-chloro-2-methylphenyl | 45 | δ(CDCl₃) 1.39(d), 1.96(s), 2.68(d), 3.17(septet), 3.46(s), 3.77(s), 4.67(m), 5.40(m), 6.79(d), 6.90-7.23(m) |
| 16a | 16a | isopropyl | 4-methoxyphenyl | 4-fluorophenyl | 30 | νmax (CHBr₃) 3500, 1742, 1712 cm⁻¹ |
| 16b | 16b | isopropyl | 4-fluorophenyl | 4-methoxyphenyl | 30 | νmax (CHBr₃) 3586, 1741, 1712 cm⁻¹ |
| 17a | 17a | isopropyl | 3-methoxyphenyl | 4-fluorophenyl | 30 | νmax (CHBr₃) 3600, 1741, 1712 cm⁻¹ |
| 17b | 17b | isopropyl | 4-fluorophenyl | 3-methoxyphenyl | 30 | νmax (CHBr₃) 3580, 1741, 1712 cm⁻¹ |
| 18 | 18 | isopropyl | 3-chlorophenyl | 3-chlorophenyl | 90 | Rf 0.35 (System A 1:1) |
| 19 | 19 | CF₃ | 3-chlorophenyl | 3-chlorophenyl | 30 | RF 0.22 (System A 7:13) |
| 20 | 20 | isopropyl | 3,5-dimethylphenyl | 3,5-dimethylphenyl | 45 | λmax (MeOH) 228.4(inf) (ε22,818), 251.6 nm (inf) (ε15,049) |
| 21a | 21a | isopropyl | 4-fluorophenyl | 4-chlorophenyl | 50 | λmax (MeOH) 230.6(inf) |
| 21b | 21b | isopropyl | 4-chlorophenyl | 4-fluorophenyl | | (ε18,765), 281.2 nm (ε13,335) |
| 22a | 22a | isopropyl | 4-fluorophenyl | 3,5-dibromophenyl | 45 | Rf 0.67 (petroleum ether b.p. |
| 22b | 22b | isopropyl | 3,5-dibromophenyl | 4-fluorophenyl | | 40-60° - EtOAc 2:1) |
| 23a | 23a | isopropyl | 4-fluorophenyl | 3-trifluoromethylphenyl | 45 | Rf 0.13 (System A 2:3) |
| 23b | 23b | isopropyl | 3-trifluoromethylphenyl | 4-fluorophenyl | | |
| 24 | 24 | Me | 4-fluorophenyl | 4-fluorophenyl | 60 | δ(CDCl₃) 2.5(s), 2.7(m), 3.45(s), 3.75(s), 4.65(m), 5.40(dd), 6.62(d), 6.8-7.45(m) |
| 25 | 25 | t-Bu | 4-fluorophenyl | 4-fluorophenyl | 60 | δ(CDCl₃) 1.5(s), 2.44(d), 3.4(s), 3.75(s), 4.4(m), 5.05-5.15(m), 6.8-7.5(m) |
| 26a* | 26a | isopropyl | 4-fluorophenyl | 4-fluorophenyl | 60 | δ(CDCl₃) 1.38(d), 1.65-2.50(m), 2.30(bs), 3.03(septet), 3.28(s), 3.71(s), 4.36(m), 5.68(dd), 6.51(d), 6.92(t), 7.08(t), 7.15-7.47(m) |

*Z isomer

TABLE 8

| Example A | From Intermediate F | R¹ | R² | R³ | Reaction time/ h | Mass Intermediate F/mg | Mass Product/ mg |
|---|---|---|---|---|---|---|---|
| 1 | 1 | isopropyl | 4-fluorophenyl | 4-pyridinyl | 4.5 | 12 | 10 |
| 2 | 2 | isopropyl | 4-fluorophenyl | 3-pyridinyl | 4.5 | 17 | 11 |
| 3a | 3a | isopropyl | 3,5-dimethylphenyl | 4-fluorophenyl | 6 | 490 | 270 |
| 3b | 3b | isopropyl | 4-fluorophenyl | 3,5-dimethylphenyl | 6 | 629 | 489 |
| 4a | 4a + 4b | isopropyl | 4-fluorophenyl | 3-chlorophenyl | 5 | 500 | 44[1] |
| 4b | 4a + 4b | isopropyl | 3-chlorophenyl | 4-fluorophenyl | 5 | 500 | 24[1] |
| 5a | 5a + 5b | isopropyl | 4-fluorophenyl | 3,5-dichlorophenyl | 5 | 610 | 35[2] |
| 5b | 5a + 5b | isopropyl | 3,5-dichlorophenyl | 4-fluorophenyl | 5 | 610 | 29[2] |
| 6a | 6a + 6b | isopropyl | 3,5-dichlorophenyl | 3-bromophenyl | 5 | 402 | 43 |
| 6b | 6a + 6b | isopropyl | 3-bromophenyl | 3,5-dichlorophenyl | 5 | 402 | 34 |
| 7a | 7a + 7b | isopropyl | 4-fluorophenyl | 3,5-dimethyl-4-fluorophenyl | 5 | 533 | 96 |
| 7b | 7a + 7b | isopropyl | 3,5-dimethyl-4-fluorophenyl | 4-fluorophenyl | 5 | 533 | 100 |
| 8a | 8a | isopropyl | 3-bromophenyl | 3,5-dimethyl-4-fluorophenyl | 5 | 260 | 74 |
| 8b | 8b | isopropyl | 3,5-dimethyl-4-fluorophenyl | 3-bromophenyl | 5 | 400 | 126 |

TABLE 8-continued

| Example A | From Intermediate F | R¹ | R² | R³ | Reaction time/ h | Mass Intermediate F/mg | Mass Product/ mg |
|---|---|---|---|---|---|---|---|
| 9a | 9a + 9b | isopropyl | 3,5-dimethyl-4-fluorophenyl | phenyl | 5 | 767 | 95 |
| 9b | 9a + 9b | isopropyl | phenyl | 3,5-dimethyl-4-fluorophenyl | 5 | 767 | 59 |
| 10a | 10a + 10b | isopropyl | 4-fluorophenyl | 4-methylphenyl | 5 | 1620 | 37[3] |
| 10b | 10a + 10b | isopropyl | 4-methylphenyl | 4-fluorophenyl | 5 | 1620 | 49.3[3] |
| 11a | 11a + 11b | isopropyl | 4-fluorophenyl | 3,5-diethyl-4-fluorophenyl | 5 | 250 | 14.5[4] |
| 11b | 11a + 11b | isopropyl | 3,5-diethyl-4-fluorophenyl | 4-fluorophenyl | 5 | 250 | 34[4] |
| 12a | 12a + 12b | isopropyl | 4-fluorophenyl | 3-bromophenyl | 5 | 600 | 52[5] |
| 12b | 12a + 12b | isopropyl | 3-bromophenyl | 4-fluorophenyl | 5 | 600 | 32[5] |
| 13a | 13a | isopropyl | 4-chloro-3,5-dimethylphenyl | 4-fluorophenyl | 5 | 378 | 161 |
| 13b | 13b | isopropyl | 4-fluorophenyl | 4-chloro-3,5-dimethylphenyl | 4 | 243 | 146 |
| 14a | 14a | isopropyl | 4-fluoro-2-methylphenyl | 4-fluorophenyl | 2.5 × 2[6] | 590 | 350 |
| 14b | 14b | isopropyl | 4-fluorophenyl | 4-fluoro-2-methylphenyl | 3.5 | 200 | 52 |
| 15a | 15a | isopropyl | 5-chloro-2-methylphenyl | 4-fluorophenyl | 5 × 2[6] | 220 | 180 |
| 15b | 15b | isopropyl | 4-fluorophenyl | 5-chloro-2-methylphenyl | 5 | 34 | 19 |
| 16a | 16a | isopropyl | 4-methoxyphenyl | 4-fluorophenyl | 5 | 320 | 100 |
| 16b | 16b | isopropyl | 4-fluorophenyl | 4-methoxyphenyl | 5 | 680 | 265 |
| 17a | 17a | isopropyl | 3-methoxyphenyl | 4-fluorophenyl | 5 | 1360 | 950 |
| 17b | 17b | isopropyl | 4-fluorophenyl | 3-methoxyphenyl | 5 | 635 | 428 |
| 18 | 18 | isopropyl | 3-chlorophenyl | 3-chlorophenyl | 5 | 23 | 23[7] |
| 19 | 19 | $CF_3$ | 3-chlorophenyl | 3-chlorophenyl | 5 | 7 | 7[8] |
| 20 | 20 | isopropyl | 3,5-dimethylphenyl | 3,5-dimethylphenyl | 5 | 513 | 395 |
| 21a | 21a + 21b | isopropyl | 4-fluorophenyl | 4-chlorophenyl | 5 | 823 | 32[9] |
| 21b | 21a + 21b | isopropyl | 4-chlorophenyl | 4-fluorophenyl | 5 | 823 | 26[9] |
| 22a | 22a + 22b | isopropyl | 4-fluorophenyl | 3,5-dibromophenyl | 5 | 118 | 40 |
| 22b | 22a + 22b | isopropyl | 3,5-dibromophenyl | 4-fluorophenyl | 5 | 118 | 11 |
| 23a | 23a + 23b | isopropyl | 4-fluorophenyl | 3-trifluoromethylphenyl | 4 | 501 | 112[10] |
| 23b | 23a + 23b | isopropyl | 3-trifluoromethylphenyl | 4-fluorophenyl | 4 | 501 | 112[10] |
| 24 | 24 | Me | 4-fluorophenyl | 4-fluorophenyl | 5 | 443 | 225 |
| 25 | 25 | t-Bu | 4-fluorophenyl | 4-fluorophenyl | 5 | 374 | 283 |
| 26a[11] | 26a | isopropyl | 4-fluorophenyl | 4-fluorophenyl | 3.5 | 346 | 286 |
| 27 | see note 12 | $CF_3$ | phenyl | 4-fluorophenyl | 4.25 | 99.7 | 75 |
| 28 | see note 12 | $CF_3$ | 4-fluorophenyl | phenyl | 6 | 71.4 | 61 |
| 29 | see note 13 | $CF_3$ | 4-fluorophenyl | 4-fluorophenyl | 5.5 | 190 | 172 |

Notes for Table 8

[1] Reaction mixture purified by CC to give mixture of Example A 4a + 4b (228 mg) A portion (100 mg) of this was further purified by preparative h.p.l.c. to give the separated isomers
[2] As for note 1, a portion (100 mg) of mixture of isomers (304 mg) purified by h.p.l.c.
[3] As for note 1 above, a portion (100 mg) of mixture of isomers (175 mg) purified by h.p.l.c
[4] As for note 1 above, a portion (100 mg) of mixture of isomers (240 mg) purified by h.p.l.c.
[5] As for note 1 above, a portion (100 mg) of mixture of isomers (374 mg) purified by h.p.l.c
[6] Reaction repeated since first crude product contained large proportion of unreacted starting material
[7] Mixture of erythro and threo (78:22) isomers obtained
[8] Mixture of erythro and threo (3:1) isomers obtained
[9] As for note 1 above, a portion (80 mg) of mixture of isomers (601 mg) purified by h.p.l.c.
[10] Mixture of 23a and 23b produced (112 mg) a portion of which was separated by h.p.l.c
[11] Z isomer
[12] Prepared from methyl (±)-(E)-7-[5(4)-(4-fluorophenyl)-4(5)-phenyl-2-trifluoromethyl-1H-imidazol-1-yl]-5-hydroxy-3-oxo-6-heptenoate - Intermediate 10c.
[13] Prepared from methyl (±)-(E)-7-[4,5-bis(4-fluorophenyl)-2-trifluoromethyl-1H-imidazol-1-yl]-5-hydroxy-3-oxo-6-heptenoate - Intermediate 10d.

CHARACTERISATION FOR EXAMPLES A

EXAMPLE A

δ(CDCl₃)

1. 1.42(d), 2.45(m), 3.16(septet), 3.75(s), 4.18(m), 4.45(m), 5.35(dd), 6.66(d), 8.40(m)
2. 1.42(d), 2.45(m), 3.17(septet), 4.18(m), 5.34(dd), 6.70(d), 7.32(m), 8.36(m), 8.60(m)
3b 1.3-1.65(m), 1.4(d), 2.2(s), 2.45(m), 3.15(septet), 3.7(s), 4.15(m), 4.42(m), 5.29(dd), 6.68(d), 6.8(m), 7.05-7.30(m)
4a 1.40(d), 1.45-1.60(m), 2.43(d), 3.13(septet), 3.73(s), 4.18-4.20(m), 4.40-4.43(m), 5.32(dd), 6.65(d), 7.03-7.27(m), 7.53(s)
5a 1.39(d), 1.43-1.67(m), 2.44(d), 3.12(septet), 3.72(s), 4.08-4.22(m), 4.36-4.48(m), 5.34(dd), 6.64(dd), 7.07-7.29(m), 7.32(d)
6a 1.40(2d), 1.40-1.62(m), 2.50(d), 3.14(septet), 3.74(s), 4.16-4.30(m), 4.56-4.45(m), 5.32(dd), 6.71(dd), 7.02-7.37(m), 7.76(m)
7a 1.40(d), 2.15(s), 2.45(m), 3.13(m), 3.73(s), 4.15(m), 4 45(m), 5.3(m), 6.65(m), 7.05-7.3(m)
8b 1.40(d), 2.24(s), 2.47(m), 3.13(m), 3.75(s), 4.15(m), 4.44(m), 5.30(dd), 6.65(d), 6.90-7.90(m)
9b 1.4(d), 2.1(s), 2.41(m), 3.14(m), 3.75(s), 4.11(m), 4.45(m), 5.29(dd), 6.7(d), 7.05-7.40(m)
10a 1.35-1.60(m), 1.40(d), 2.25(s), 2.45(m), 3.15(septet), 3.70(s), 4.15(m), 4.40(m), 5.30(m), 6.70(d), 7.05-7.35(m)
11a 1.05(t), 1.10-1.65(m), 1.40(d), 2.45-2.50(m), 2.55(q), 3.15(septet), 3.75(s), 4.20(m), 4.45(m), 5.30(dd), 6.68(m), 7.05-7.30(m)
12a 1.32-1.66(m), 1.42(d), 2.45(m), 3.14(septet), 3.74(s), 4.17(m), 4.43(m), 5.33(dd), 6.67(d), 6.99-7.29(m), 7.71(m)
13b 1.35-1.55(m), 1.40(d), 2.24(s), 2.47(d), 3.15(septet), 3.73(s), 4.17(m), 4.43(m), 5.30(dd), 6.68(d), 7.03-7.30(m)

δ(CDCl₃)

14b 1.05-1.58(m), 1.30(d), 1.97(s), 2.37(d), 3.09(septet), 3.65(s), 4.30(m), 5.33(dd), 6.59-7.06(m)
15b 1.13-1.64(m), 1.32(d), 1.90(s), 2.40(d), 3.08(septet), 3.67(s), 4.13(m), 4.37(m), 5.35(dd), 6.63(d), 6.84-7.15(m)
16b 1.40(d), 1.55(m), 2.45(m), 3.12(m), 3.72(s), 3.74(s), 4.15(m), 4.45(m), 5.30(dd), 6.7-7.40(m)
17b 1.30(d), 1.50(m), 2.46(m), 3.13(m), 3.70(s), 3.76(s), 5.30(m), 6.68(dd), 6.90-7.30(m)

21a 1.40(d), 1.30–1.70(m), 2.45(d), 3.15(septet), 3.73(s), 4.09–4.23(m), 4.37–4.49(m), 5.31(dd), 6.66(dd), 7.03–7.29(m), 7.36(d)

22a 1.40(d), 1.45–1.82(m), 2.47(d), 3.13(septet), 3.71(s), 4.10–4.23(m), 4.38–4.49(m), 5.35(dd), 6.65(d), 7.13(t), 7.19–7.60(m)

23a 1.41(d), 1.10–1.60(m), 2.42(d), 3.15(septet), 3.73(s), 4.15–4.25(m), 4.38–4.49(m), 5.29(dd), 6.71(dd), 6.92(t), 7.3–7.7(m)

24 1.20–1.80(m), 2.45(m), 2.50(s), 3.75(s), 4.20(m), 4.45(m), 5.42(dd), 6.60(d), 6.80–7.50(m)

25 1.20–1.80(m), 1.50(s), 2.40(m), 3.73(s), 4.10(m), 4.40(m), 5.65(dd), 6.90(d), 6.81–7.50(m)

28 1.40–1.62(m), 2.47(d), 3.8(s), 3.7(s), 4.10–4.23(m), 4.41–4.51(m), 5.66(dd), 6.7(d), 7.13(t), 7.20–7.35(m), 7.40–7.48(m).

CHARACTERISATION FOR EXAMPLES B

EXAMPLE B $\delta(D_2O)$ 1. 1.35(d), 2.26(m), 3.30(septet), 3.65(m), 4.37(m), 5.61(dd), 6.73(d), 8.32(m).
2. 1.48(d), 2.40(m), 3.41(septet), 3.79(m), 4.48(m), 5.72(dd), 6.92(d), 7.90(m), 8.48(m), 8.60(m).

3b. 1.2–1.85(m), 1.35(d), 2.05(s), 2.25(m), 3.20(septet), 3.70(m), 4.35(m), 5.48(dd), 6.66(d), 6.80–7.15(m).

4a. 1.33(d), 1.35–1.52(m), 1.58–1.84(m), 2.25(d), 3.26(septet), 3.58–3.73(m), 4.28–4.41(m), 5.54(dd), 6.74(d), 7.11–7.37(m).

5a. 1.33(d), 1.40–1.83(m), 2.26(d), 3.24(septet), 3.60–3.76(m), 4.27–4.42(m), 5.51(dd), 6.71(d), 7.08–7.33(m).

TABLE 9

| Example B | From Example A | $R^1$ | $R^2$ | $R^3$ | Volume 0.1N NaOH (aq) mls | Mass Example A/mg | Mass Product/ mg |
|---|---|---|---|---|---|---|---|
| 1 | 1 | isopropyl | 4-fluorophenyl | 4-pyridinyl | 0.21 | 9.5 | 9 |
| 2 | 2 | isopropyl | 4-fluorophenyl | 3-pyridinyl | 0.11 | 5 | 5 |
| 3a | 3a | isopropyl | 3,5-dimethylphenyl | 4-fluorophenyl | 4.84 | 245 | 184 |
| 3b | 3b | isopropyl | 4-fluorophenyl | 3,5-dimethylphenyl | 9.1 | 459 | 378 |
| 4a | 4a | isopropyl | 4-fluorophenyl | 3-chlorophenyl | 0.8 | 44 | 35 |
| 4b | 4b | isopropyl | 3-chlorophenyl | 4-fluorophenyl | 0.38 | 21 | 19 |
| 5a | 5a | isopropyl | 4-fluorophenyl | 3,5-dichlorophenyl | 0.6 | 35 | 31 |
| 5b | 5b | isopropyl | 3,5-dichlorophenyl | 4-fluorophenyl | 0.5 | 29 | 29 |
| 6a | 6a | isopropyl | 3,5-dichlorophenyl | 3-bromophenyl | * | 28 | 25 |
| 6b | 6b | isopropyl | 3-bromophenyl | 3,5-dichlorophenyl | * | 19 | 14 |
| 7a | 7a | isopropyl | 4-fluorophenyl | 3,5-dimethyl-4-fluorophenyl | 1.3 | 70 | 60 |
| 7b | 7b | isopropyl | 3,5-dimethyl-4-fluorophenyl | 4-fluorophenyl | 1.55 | 80 | 65 |
| 8a | 8a | isopropyl | 3-bromophenyl | 3,5-dimethyl-4-fluorophenyl | 1.2 | 70 | 55 |
| 8b | 8b | isopropyl | 3,5-dimethyl-4-fluorophenyl | 3-bromophenyl | 1.7 | 100 | 110 |
| 9a | 9a | isopropyl | 3,5-dimethyl-4-fluorophenyl | phenyl | 2.0 | 120 | 120 |
| 9b | 9b | isopropyl | phenyl | 3,5-dimethyl-4-fluorophenyl | 1.1 | 58 | 40 |
| 10a | 10a | isopropyl | 4-fluorophenyl | 4-methylphenyl | 0.62 | 30 | 19 |
| 10b | 10b | isopropyl | 4-methylphenyl | 4-fluorophenyl | 1.04 | 51 | 47.7 |
| 11a | 11a | isopropyl | 4-fluorophenyl | 3,5-diethyl-4-fluorophenyl | 0.28 | 15 | 11 |
| 11b | 11b | isopropyl | 3,5-diethyl-4-fluorophenyl | 4-fluorophenyl | 0.54 | 30 | 24 |
| 12a | 12a | isopropyl | 4-fluorophenyl | 3-bromophenyl | 1.31 | 46 | 43 |
| 12b | 12b | isopropyl | 3-bromophenyl | 4-fluorophenyl | 0.73 | 27 | 24 |
| 13a | 13a | isopropyl | 4-chloro-3,5-dimethylphenyl | 4-fluorophenyl | 2.62 | 142 | 120 |
| 13b | 13b | isopropyl | 4-fluorophenyl | 4-chloro-3,5-dimethylphenyl | 2.37 | 128 | 103 |
| 14a | 14a | isopropyl | 4-fluoro-2-methylphenyl | 4-fluorophenyl | 6.65 | 339 | 308 |
| 14b | 14b | isopropyl | 4-fluorophenyl | 4-fluoro-2-methylphenyl | 0.88 | 45 | 40 |
| 15a | 15a | isopropyl | 5-chloro-2-methylphenyl | 4-fluorophenyl | 2.6 | 135 | 90 |
| 15b | 15b | isopropyl | 4-fluorophenyl | 5-chloro-2-methylphenyl | 0.88 | 45 | 40 |
| 16a | 16a | isopropyl | 4-methoxyphenyl | 4-fluorophenyl | 0.45 | 22 | 20 |
| 16b | 16b | isopropyl | 4-fluorophenyl | 4-methoxyphenol | 0.72 | 35 | 33 |
| 17a | 17a | isopropyl | 3-methoxyphenol | 4-fluorophenyl | 1.24 | 60 | 55 |
| 17b | 17b | isopropyl | 4-fluorophenyl | 3-methoxyphenyl | 0.75 | 38 | 34 |
| 18 | 18 | isopropyl | 3-chlorophenyl | 3-chlorophenyl | 0.41 | 23 | 19 |
| 19 | 19 | $CF_3$ | 3-chlorophenyl | 3-chlorophenyl | 0.12 | 7 | 7 |
| 20 | 20 | isopropyl | 3,5-dimethylphenyl | 3,5-dimethylphenyl | * | 315 | 234 |
| 21a | 21a | isopropyl | 4-fluorophenyl | 4-chlorophenyl | * | 33 | 29 |
| 21b | 21b | isopropyl | 4-chlorophenyl | 4-fluorophenyl | * | 27 | 23 |
| 22a | 22a | isopropyl | 4-fluorophenyl | 3,5-dibromophenyl | * | 40 | 34 |
| 22b | 22b | isopropyl | 3,5-dibromophenyl | 4-fluorophenyl | * | 11 | 12 |
| 23a | 23a | isopropyl | 4-fluorophenyl | 3-trifluoromethylphenyl | 0.42 | 24 | 21 |
| 23b | 23b | isopropyl | 3-trifluoromethylphenyl | 4-fluorophenyl | 0.29 | 17 | 17 |
| 24 | 24 | Me | 4-fluorophenyl | 4-fluorophenyl | 4.72 | 220 | 220 |
| 25 | 25 | t-Bu | 4-fluorophenyl | 4-fluorophenyl | 5.50 | 281 | 168 |
| 26a[2] | 26a | isopropyl | 4-fluorophenyl | 4-fluorophenyl | 0.63 | 33 | 22.7 |
| 27 | 27 | $CF_3$ | phenyl | 4-fluorophenyl | 1.16 | 62 | 54 |
| 28 | 28 | $CF_3$ | 4-fluorophenyl | phenyl | 1.12 | 59 | 51 |
| 29 | 29 | $CF_3$ | 4-fluorophenyl | 4-fluorophenyl | 1.72 | 85.5 | 76.4 |
| 30 | see note 3 | isopropyl 1 | 4-fluorophenyl | 4-hydroxyphenyl | 0.7 | 35 | 26 |
| 31 | see note 4 | isopropyl 1 | 4-fluorophenyl | 3-hydroxyphenyl | 0.75 | 14 | 18 |
| 32 | see note 5 | isopropyl 1 | 4-fluorophenyl | 3-pyridinyl-1[1]-oxide | 0.05 | 2.5 | 2.5 |

*0.1N NaOH added until only a trace of starting material observed on t.l.c.
[1]Mixture of erythro and threo isomers obtained.
[2]Z-isomer.
[3]Prepared from methyl(±)-erythro-(E)-3,5-dihydroxy-7-[5-(4-fluorophenyl)-4-(4-hydroxyphenyl)-2-(1-methylethyl)-1H-imidazol-1-yl]-6-heptenoate - Example 22.
[4]Prepared from methyl(±)-erythro-(E)-3,5-dihydroxy-7-[5-(4-fluorophenyl)-4-(3-hydroxyphenyl)-2-(1-methylethyl)-1H-imidazol-1-yl]-6-heptenoate - Example 23
[5]Prepared from methyl(±)-erythro-(E)-3,5-dihydroxy-7-[5-(4-fluorophenyl)-2-(1-methylethyl)-4-(3-pyridinyl)-1H-imidazol-1-yl]-6-heptenoate, 1'-oxide - Example 12.

6a. 1.31(d), 1.58–1.85(m), 2.16–2.40(m), 3.14–3.33(m), 3.68–3.82(m), 4.29–4.43(m), 5.50(dd), 6.70(d), 6.93–7.53(m).

7a. 1.31(d), 1.92(s), 2.25(m), 3.26(m), 3.75(m), 4.31(m), 5.45(dd), 6.65(d), 6.81–7.02(m).

8b. 1.31(d), 1.6–1.85(m), 2.2(s), 2.22(m), 3.25(m), 3.55(m), 4.31(m), 5.5(dd), 6.7(d), 6.8–7.5(m).

9b. 1.31(d), 1.15–1.75(m), 2.0(s), 2.2(m), 3.25(m), 3.55(m), 4.30(m), 4.95(m), 5.45(dd), 6.75(d), 6.90–7.40(m).

10a. 1.40–1.80(m), 1.30(d), 2.20(m), 2.25(s), 3.25(septet), 3.65(m), 4.32(m), 5.60(dd), 6.75(d), 7.05–7.40(m).

11a. 1.00–1.85(m), 1.10(t), 1.35(d), 2.20–2.25(m), 2.45(q), 2.35(septet), 3.70(m), 4.30(m), 5.50(dd), 6.75(d), 7.00–7.30(m).

12a. 1.20–1.87(m), 1.34(d), 2.27(d), 3.26(septet), 3.68(m), 4.33(m), 5.49(dd), 6.71(d), 7.03–7.50(m).

13b. 1.30–1.86(m), 1.33(d), 2.05(s), 2.26(m), 3.25(septet), 3.73(m), 4.33(m), 5.48(dd), 6.68(d), 6.87–7.08(m).

δ(D₂O)

14b. 1.34(d), 1.43–1.86(m), 1.99(s), 2.29(m), 3.28(septet), 3.77(m), 4.40(m), 5.57(dd), 6.81–7.33(m).

15b. 1.43–1.87(m), 1.34(d), 1.99(s), 2.29(m), 3.28(septet), 3.77(m), 4.39(m), 5.57(dd), 6.83–7.30(m), 6.87(d).

16b. 1.35(d), 1.3–1.8(m), 2.25(m), 3.28(m), 3.65(m), 3.37(s), 4.35(m), 5.51(dd), 6.75(d), 6.85–7.30(m).

17b. 1.35(d), 1.2–1.8(m), 2.24(m), 3.25(m), 3.65(s), 3.75(m), 4.32(m), 5.50(dd), 6.72(d), 6.75–7.30(m).

21a. 1.32(d), 1.40–1.84(m), 2.25(d), 3.26(septet), 3.57–3.74(m), 4.27–4.41(m), 5.52(dd), 6.73(d), 7.08–7.35(m).

22a. 1.30(d), 1.35–1.85(m), 2.13–2.36(m), 3.19(septet), 3.70–3.85(m), 4.23–4.38(m), 5.47(dd), 6.61(d), 6.92–7.14(m), 7.24–7.54(m), 7.67(d).

23a* 0.80–1.50(m), 1.31(d), 1.72(dd), 1.94(dd), 3.16(septet), 3.40–3.60(m), 4.10–4.25(m), 5.53(dd), 6.58(d), 7.25–7.7(m).

* (DMSO-d₆)

24. 1.40–1.80(m), 2.28(m), 2.45(s), 3.73(m), 4.32(m), 5.55(dd), 6.60(d), 6.90–7.40(m).

25. 1.10–1.60(m), 1.45(s), 2.20(m), 3.45–3.55(m), 4.30–4.40(m), 5.45(dd), 6.92(d), 6.90–7.40(m).

28. 1.36–1.50(m), 1.60–1.73(m), 2.24(d), 3.58–3.70(m), 4.33(q), 5.74(dd), 6.73(d), 7.10–7.40(m).

29. 1.37–1.50(m), 1.59–1.84(m), 2.24(d), 3.56–3.69(m), 4.35(q), 5.78(dd), 6.79(d), 6.97–7.09(m), 7.15–7.40(m).

30. 1.48(d), 1.45–1.90(m), 2.41(m), 3.45(m), 3.85(m), 4.50(m), 5.68(m), 6.88(d), 7.25–7.50(m).

31. 1.32(d), 1.1–1.9(m), 2.25(m), 3.25(m), 3.65(m), 4.35(m), 5.51(dd), 6.68–7.30(m).

32. 1.35(d), 2.28(m), 3.29(septet), 3.65(m), 4.38(m), 5.63(dd), 6.75(d), 7.67(m), 8.13(m), 8.26(s).

PHARMACY EXAMPLES

EXAMPLE 1—TABLETS

| a) | | |
|---|---|---|
| | Compound of Example 6 | 5.0 mg |
| | Lactose | 95.0 mg |
| | Microcrystalline Cellulose | 90.0 mg |
| | Cross-linked Polyvinylpyrrolidone | 8.0 mg |
| | Magnesium Stearate | 2.0 mg |
| | Compression weight | 200.0 mg |

The compound of Example 6, microcrystalline cellulose, lactose and cross linked polyvinylpyrrolidone are sieved through a 500 micron sieve and blended in a suitable mixer. The magnesium stearate is sieved through a 250 micron sieve and blended with the active blend. The blend is compressed into tablets using suitable punches.

| b) | | |
|---|---|---|
| | Compound of Example 6 | 5.0 mg |
| | Lactose | 165.0 mg |
| | Pregelatinised Starch | 20.0 mg |
| | Cross-linked Polyvinylpyrrolidone | 8.0 mg |
| | Magnesium Stearate | 2.0 mg |
| | Compression weight | 200.0 mg |

The compound of Example 6, lactose and pregelatinised starch are blended together and granulated with water. The wet mass is dried and milled. The magnesium stearate and cross-linked polyvinylpyrrolidone are screened through a 250 micron sieve and blended with the granule. The resultant blend is compressed using suitable tablet punches.

EXAMPLE 2—CAPSULES

| (a) | | |
|---|---|---|
| | Compound of Example 6 | 5.0 mg |
| | Pregelatinised Starch | 193.0 mg |
| | Magnesium Stearate | 2.0 mg |
| | Fill weight | 200.0 mg |

The compound of Example 6, and pregelatinised starch are screened through a 500 micron mesh sieve, blended together and lubricated with magnesium stearate, (meshed through a 250 micron sieve). The blend is filled into hard gelatin capsules of a suitable size.

| (b) | | |
|---|---|---|
| | Compound of Example 6 | 5.0 mg |
| | Lactose | 177.0 mg |
| | Polyvinylpyrrolidone | 8.0 mg |
| | Cross-linked Polyvinylpyrrolidone | 8.0 mg |
| | Magnesium Stearate | 2.0 mg |
| | Fill weight | 200.0 mg |

The compound of Example 6 and lactose are blended together and granulated with a solution of polyvinylpyrrolidone. The wet mass is dried and milled. The magnesium stearate and cross-linked polyvinylpyrrolidone are screened through a 250 micron sieve and blended with the granule. The resultant blend is filled into hard gelatin capsules of a suitable size.

EXAMPLE 3—SYRUP

| (a) | | |
|---|---|---|
| | Compound of Example 6 | 5.0 mg |
| | Hydroxypropyl Methylcellulose | 45.0 mg |
| | Propyl Hydroxybenzoate | 1.5 mg |
| | Butyl Hydroxybenzoate | 0.75 mg |
| | Saccharin Sodium | 5.0 mg |
| | Sorbitol Solution | 1.0 ml |
| | Suitable Buffers | qs |
| | Suitable Flavours | qs |
| | Purified Water to | 10. ml |

The hydroxpropyl methylcellulose is dispersed in a portion of hot purified water together with the hydroxybenzoates and the solution is allowed to cool to room temperature. The saccharin sodium, flavours and sorbitol solution are added to the bulk solution. The compound of Example 6 is dissolved in a portion of the remaining water and added to the bulk solution. Suitable buffers may be added to control the pH in the region of maximum stability. The solution is made up to volume, filtered and filled into suitable containers.

We claim:

1. Compounds of formula

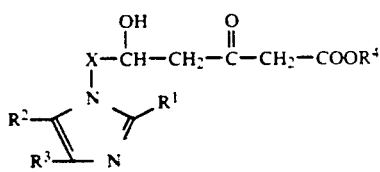

wherein one of $R^1$ and $R^2$ represents a $C_{1-6}$ alkyl group optionally substituted by one to three halogen atoms and the other represents a ring selected from the group consisting of phenyl, pyridyl and pyridyl N-oxide, said ring optionally being substituted by one or more substituents selected from the group consisting of halogen atoms, hydroxyl, $C_{1-3}$ alkyl, $C_{1-3}$ alkoxy and trifluoromethyl groups;

wherein $R^3$ represents a ring selected from the group consisting of phenyl, pyridyl and pyridyl N-oxide, said ring optionally being substituted by one or more substituents selected from the group consisting of halogen atoms, hydroxyl, $C_{1-3}$ alkyl, $C_{1-3}$ alkoxy and trifluoromethyl groups, with the proviso that not more than one of the groups $R^1$, $R^2$ and $R^3$ represents an optionally substituted pyridyl or pyridyl N-oxide ring;

wherein $R^4$ represents a hydrogen atom, a carboxyl protecting group or a cation; and wherein X represents —CH=CH—.

2. Compounds of formula

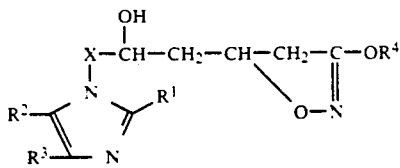 (XX)

wherein one of $R^1$ and $R^2$ represents a $C_{1-6}$ alkyl group optionally substituted by one to three halogen atoms and the other represents a ring selected from the group consisting of phenyl, pyridyl and pyridyl N-oxide, said ring optionally being substituted by one or more substituents selected from the group consisting of halogen atoms, hydroxyl, $C_{1-3}$ alkyl, $C_{1-3}$ alkoxy and trifluoromethyl groups;

wherein $R^3$ represents a ring selected from the group consisting of phenyl, pyridyl and pyridyl N-oxide, said ring optionally being substituted by one or more substituents selected from the group consisting of halogen atoms, hydroxyl, $C_{1-3}$ alkyl, $C_{1-3}$ alkoxy and trifluoromethyl groups, with the proviso that not more than one of the groups $R^1$, $R^2$ and $R^3$ represents an optionally substituted pyridyl or pyridyl N-oxide ring;

wherein $R^4$ represents a hydrogen atom, a carboxyl protecting group or a cation; and wherein X represents —CH=CH—.

* * * * *